United States Patent
Herekar et al.

(10) Patent No.: US 11,957,621 B2
(45) Date of Patent: Apr. 16, 2024

(54) ANGLE-OPENING GLAUCOMA TREATMENT METHODS AND APPARATUS

(71) Applicant: ALeyeGN Technologies LLC, Saratoga, CA (US)

(72) Inventors: Rajeev Herekar, Palo Alto, CA (US); Satish V. Herekar, Palo Alto, CA (US); John Randall Samples, Olympia, WA (US)

(73) Assignee: ALeyeGN Technologies LLC, Saratoga, CA (US)

( * ) Notice: Subject to any disclaimer, the term of this patent is extended or adjusted under 35 U.S.C. 154(b) by 580 days.

(21) Appl. No.: 16/649,795

(22) PCT Filed: Sep. 21, 2018

(86) PCT No.: PCT/US2018/052261
§ 371 (c)(1),
(2) Date: Mar. 23, 2020

(87) PCT Pub. No.: WO2019/060756
PCT Pub. Date: Mar. 28, 2019

(65) Prior Publication Data
US 2020/0306080 A1  Oct. 1, 2020

Related U.S. Application Data

(60) Provisional application No. 62/561,642, filed on Sep. 21, 2017.

(51) Int. Cl.
*A61F 9/008* (2006.01)
*A61B 3/14* (2006.01)
(Continued)

(52) U.S. Cl.
CPC .......... *A61F 9/008* (2013.01); *A61F 9/00802* (2013.01); *A61F 9/00821* (2013.01);
(Continued)

(58) Field of Classification Search
CPC .. A61F 9/008; A61F 9/00802; A61F 9/00821; A61F 9/00745; A61F 9/00817;
(Continued)

(56) References Cited

U.S. PATENT DOCUMENTS 6,146,375 A * 11/2000 Juhasz ................ A61F 9/00825
606/5
8,995,618 B2 * 3/2015 Gertner ................ A61B 6/506
378/68
(Continued)

FOREIGN PATENT DOCUMENTS

WO   WO 2014/150601      9/2014

OTHER PUBLICATIONS

International Search Report and Written Opinion for related International Application No. PCT/US2018/052261, dated Nov. 20, 2018, 11 pages.
(Continued)

*Primary Examiner* — Gary Jackson
*Assistant Examiner* — Sebastian X Lukjan
(74) *Attorney, Agent, or Firm* — Klarquist Sparkman, LLP

(57) ABSTRACT

An iridocorneal angle of the eye can be opened with a plurality of treatment locations at least about 2 mm radially outward from a limbus of the eye. The opening on the angle can be beneficial for treating both narrow angle glaucoma and open angle glaucoma. The plurality of treatment locations located away from the limbus can decrease invasiveness and complexity of the procedure. The plurality of treatment locations at least about 2 mm away from the limbus can provide tensioning to zonules coupled to the lens of the eye to flatten the lens of the eye, which can allow the iris to move posteriorly so as to open the iridocorneal angle. The plurality of treatment locations may comprise scleral
(Continued)

locations, in which shrinkage of scleral tissue at the plurality of treatment locations provides tensioning to the zonules.

19 Claims, 53 Drawing Sheets

(51) Int. Cl.
  *A61B 17/00*       (2006.01)
  *A61F 9/007*       (2006.01)
(52) U.S. Cl.
  CPC ....... *A61B 3/14* (2013.01); *A61B 2017/00141* (2013.01); *A61B 2017/00154* (2013.01); *A61F 9/00745* (2013.01); *A61F 9/00817* (2013.01); *A61F 2009/00868* (2013.01); *A61F 2009/00891* (2013.01); *A61F 2009/00897* (2013.01)
(58) Field of Classification Search
  CPC .. A61F 2009/00868; A61F 2009/00891; A61F 2009/00897; A61B 3/14; A61B 2017/00141; A61B 2017/00154
  See application file for complete search history.

(56) References Cited

U.S. PATENT DOCUMENTS

| | | | |
|---|---|---|---|
| 2003/0028228 A1* | 2/2003 | Sand | A61F 9/008 606/4 |
| 2006/0224146 A1* | 10/2006 | Lin | A61F 9/00821 606/4 |
| 2006/0241750 A1* | 10/2006 | Zdenek | A61F 2/147 623/4.1 |
| 2015/0164692 A1* | 6/2015 | Lin | A61B 1/042 606/5 |
| 2015/0366706 A1 | 12/2015 | Belkin et al. | |
| 2015/0374539 A1 | 12/2015 | Buzawa et al. | |
| 2016/0256324 A1* | 9/2016 | Suzuki | A61F 9/00825 |

OTHER PUBLICATIONS

Extended European Search Report for related EP Application No. 18857583.1, 8 pages, dated May 18, 2021.

\* cited by examiner

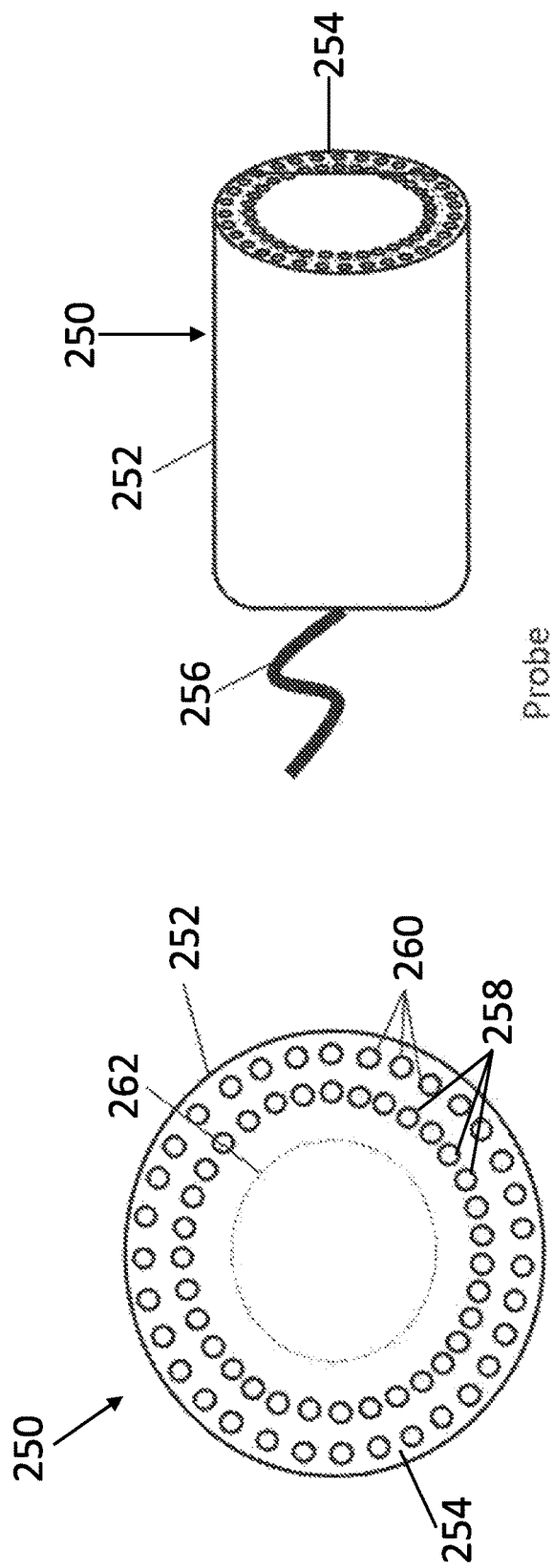
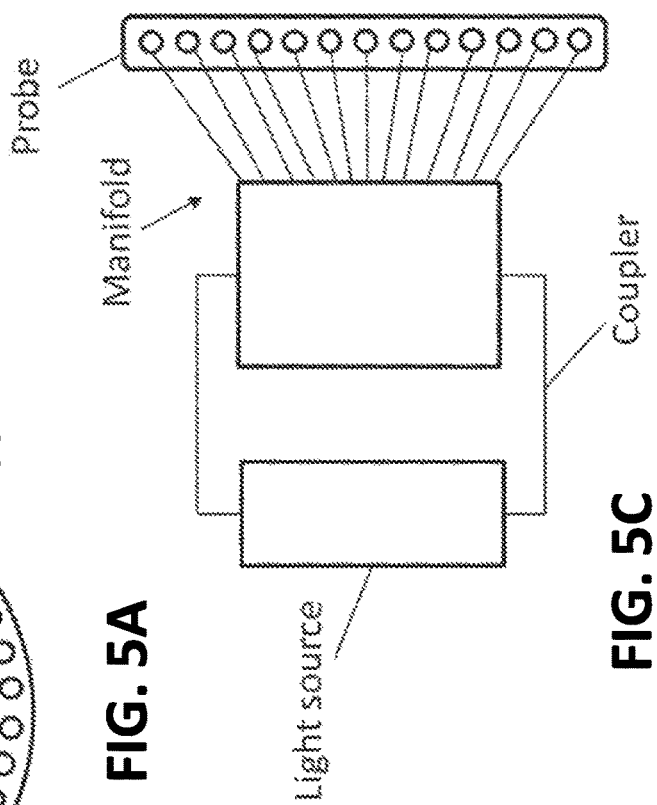
FIG. 5A
FIG. 5B
FIG. 5C

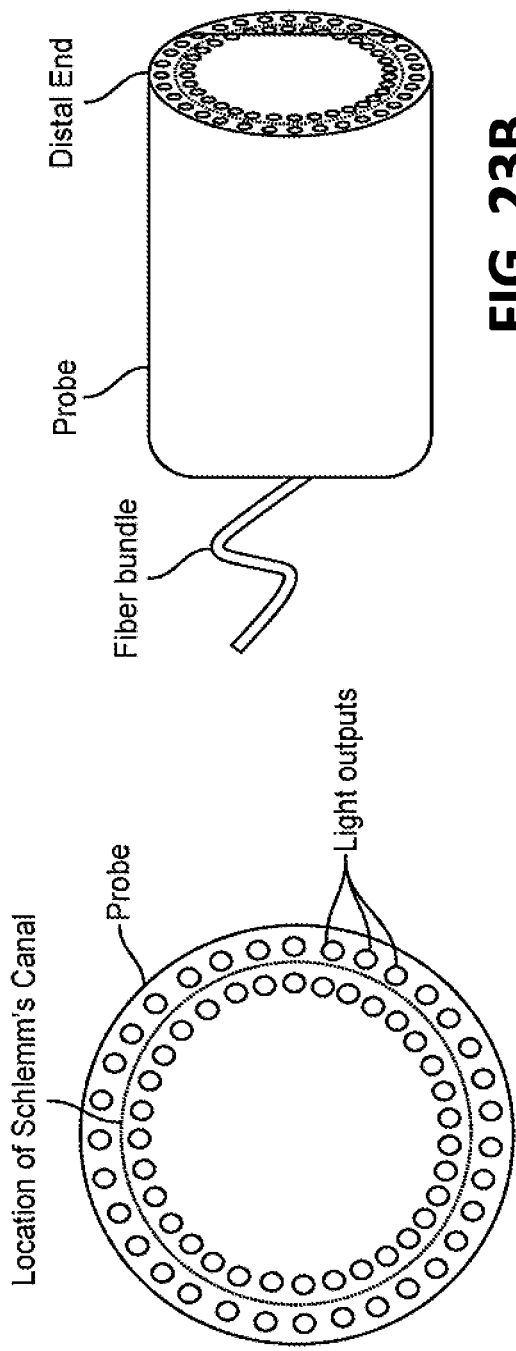
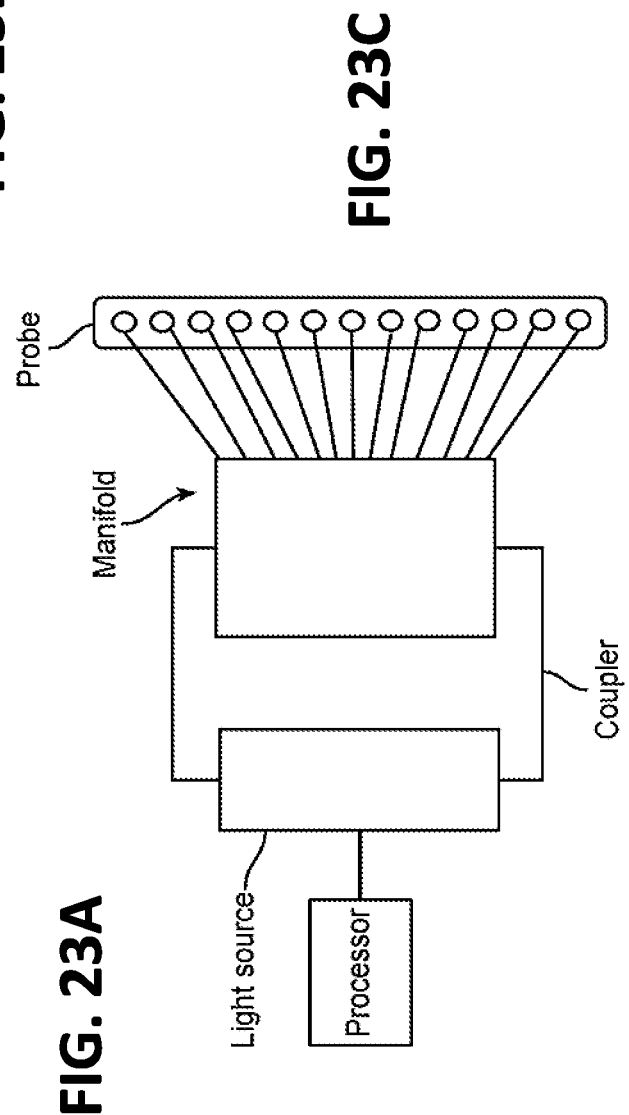

FIG. 31A

ANGLE-OPENING GLAUCOMA TREATMENT METHODS AND APPARATUS

CROSS REFERENCE TO RELATED APPLICATIONS

This is the U.S. National Stage of International Application No. PCT/US2018/052261, filed Sep. 21, 2018, which was published in English under PCT Article 21(2), which in turn claims the benefit of U.S. Provisional Application No. 62/561,642, filed Sep. 21, 2017. The provisional application is incorporated herein in its entirety.

The subject matter of the present application is related to the following patent applications, the entire disclosures of which are incorporated by reference herein to the extent they are not inconsistent with the present disclosure:

U.S. App. Ser. No. 62/385,234, filed Sep. 8, 2016, entitled "EFFECTIVE OCULAR LENS POSITIONING AND GLAUCOMA TREATMENT METHODS AND APPARATUS," U.S. App. Ser. No. 62/473,269, filed Mar. 17, 2017, entitled "GLAUCOMA TREATMENT METHODS AND APPARATUS," U.S. App. Ser. No. 62/556,228, entitled "GLAUCOMA TREATMENT METHODS AND APPARATUS," PCT/US2017/50799, filed Sep. 8, 2017, entitled "GLAUCOMA TREATMENT METHODS AND APPARATUS," PCT/US2017/023092, filed on 17 Mar. 2017, entitled "EFFECTIVE OCULAR LENS POSITIONING METHODS AND APPARATUS," PCT/US2016/055829, filed on 6 Oct. 2016, entitled "ULTRASOUND DIRECTED CAVITATIONAL METHODS AND SYSTEMS FOR OCULAR TREATMENTS," PCT/US2014/023763, filed 11 Mar. 2014, entitled "SCLERAL TRANSLOCATION ELASTO-MODULATION METHODS AND APPARATUS" and U.S. Provisional Application 62/640,502, filed Mar. 8, 2018, entitled "GLAUCOMA TREATMENT METHODS AND APPARATUS."

FIELD

This invention concerns a procedure for lowering intraocular pressure and/or treating glaucoma by applying energy to the eye.

BACKGROUND

Glaucoma is a group of diseases, often characterized by increased intraocular pressure (IOP) that result in damage to the optic nerve. Aqueous humor is produced from the ciliary processes, moves through the pupil into the anterior chamber and into the trabecular meshwork, Schlemm's canal, and uveoscleral outflow pathways. Increased IOP is the result of an imbalance between the production of aqueous humor from the ciliary body and resistance to its outflow through the normal anatomic outflow tract. Glaucoma can lead to chronic, progressive deterioration of the optic nerve that may be detected by identifying cupping and atrophy of the optic disc. The effects of this damage may be accompanied by a progressive loss of the peripheral visual field followed by a loss of central vision that results in irreversible blindness if not timely treated.

The anterior chamber of the eye is the aqueous humor-filled space between the iris and the cornea's innermost surface. The "angle" of the anterior chamber refers to the angle between the iris and the cornea (iridocorneal angle) that is near the limbus which circumscribes the cornea at the border between the transparent cornea and the opaque sclera. Near the vertex of the iridocorneal angle is the trabecular meshwork and Schlemm's canal through which much of the aqueous humor leaves the eye to maintain normal IOP. The depth of the anterior chamber varies between 1.5 and 4.0 mm, averaging 3 mm, and it tends to become shallower with age. Although there are many causes of glaucoma, the most common types are defined with reference to the angle of the anterior chamber: open-angle glaucoma and angle closure glaucoma. Open-angle glaucoma usually develops slowly and painlessly over time and is commonly attributed to a functional or structural obstruction of aqueous outflow within the trabecular meshwork or uveoscleral tract. Angle closure glaucoma (also known as narrow-angle glaucoma) typically occurs when the iris moves forward and narrows the angle of the anterior chamber between the iris and cornea to decrease the depth of the anterior chamber. Angle closure glaucoma can present gradually or suddenly. The sudden presentation may involve eye pain, blurred vision, dilation of the pupil, hyperemia and even nausea.

The most common treatment for glaucoma is the use of medication, such as eye drops. Commonly used eye drops are prostaglandin analogs, beta-adrenergic receptor antagonists, alpha2-adrenergic agonists, and miotic agents. Although the use of such medications has greatly improved the treatment of glaucoma, topical medication in the eye may have local and systemic side-effects. Patient adherence to medication protocols can also be unpredictable and lifelong use of the medication can be expensive. Poor compliance with medication use over extended periods of time is a major reason for vision loss in glaucoma patients. To help circumvent these problems, and treat refractory cases, surgical interventions such as trabeculotomies and antifibrotics with tube shunts have been developed.

Cyclodestructive treatments have traditionally been reserved for blind painful eyes. Transscleral cytophotocoagulation is an ab externo approach that uses a continuous wave diode laser to ablate the ciliary body and decrease aqueous production. Argon laser trabeculoplasty (ALT) aims a thermal argon laser spot at the trabecular meshwork in the anterior angle of the eye. The more recently developed selective laser trabeculoplasty (SLT) uses a 532-nm frequency doubled Nd:YAG laser to target melanin pigment in trabecular meshwork cells. Alternatively, microinvasive ab intern glaucoma surgeries (MIGS) introduce a trabectome handpiece into the eye to physically unroof Schlemm's canal. Stents may be injected into the eye to provide trabecular bypass routes, supraciliary and suprachoridal outflow, or bleb formation.

However, therapies such as trabeculectomy surgery, implantation of glaucoma drainage devices or MIGS require invasive intraocular surgical intervention that can have adverse safety risks in some instances. ALT and SLT are relatively complex procedures that usually require specialized use of a gonioscope lens contacting the cornea to reflect the laser beam through the anterior chamber into the iridocorneal. angle of the eye. It would be advantageous to have a glaucoma treatment procedure that was less invasive or more readily performed yet still effective in reducing IOP without inducing excessive inflammation and scarring, and which minimizes the need for post-operative interventions.

SUMMARY

The systems and methods disclosed herein can open an iridocorneal angle of the eye by delivering energy ab externo to a plurality of treatment locations at least about 2 mm radially outward from a limbus of the eye to treat glaucoma of the eye. In particular embodiments the treatment locations are on the sclera anterior to the equator of the lens. The opening of the iridocorneal angle can be within a range from about 0.5 degrees to about 10 degrees and can be beneficial for treating both narrow angle glaucoma and open angle glaucoma. The opening of the angle can provide beneficial effects to the trabecular meshwork, Schlemm's canal, the collector channels and ostia of the collector channels. In some embodiments the opening of the angle can improve aqueous outflow of the eye associated with narrow angle glaucoma, by moving the iris away from the cornea to open the iridocorneal angle.

The disclosed methods are relatively non-invasive and straightforward. For example, the treatment locations are located on the surface of the eye and can be visualized and treated without the use of a gonioscope. The plurality of ab externo treatment locations at least about 2 mm away from the limbus can provide tensioning to zonules coupled to the lens of the eye to flatten the lens of the eye, which can allow the iris to move posteriorly to open the iridocorneal angle. The treatment locations may include scleral locations, in which shrinkage of scleral tissue at the plurality of treatment locations provides tensioning to the zonules. The treatment locations may include scleral locations near the lens equator and anterior to the lens equator by about 3 mm, and locations in between. The energy delivered to the plurality of locations may comprise thermal energy, RF energy, mechanical energy, electrical energy, microwave energy, light energy, high intensity ultrasound energy, or ultrasound energy. Although reference is made to the treatment of glaucoma with a plurality of treatment locations away from Schlemm's canal, the methods and systems can be combined with other treatments such as glaucoma treatments near Schlemm's canal and refractive treatments of the eye.

In a first aspect, a system for treating glaucoma of an eye is provided. The system comprises an energy source configured to generate energy to treat the eye, a processor, and an energy delivery system coupled to the energy source and the processor. The processor is configured with instructions to direct energy to a plurality of treatment locations of the eye, the plurality of treatment locations at least about 2 mm radially outward from a limbus and corresponding to an angle within a range from about 30 degrees to about 360 degrees around a sclera of the eye. The energy delivery system is configured to deliver the energy (for example externally) to the plurality of treatment locations on the surface of the eye to open an angle of the eye by an amount within a range from about 0.5 degrees to about 10 degrees.

In some embodiments, the eye may comprise a human eye and plurality of locations correspond to a surface area on the sclera. The surface area may be within a range from about 1 $mm^2$ to about 100 $mm^2$. The surface area may be located on a sclera of the eye radially outward from the limbus by at least 2 mm, or more than 2 mm, for example at least about 2.5 mm but anterior to a lens equator on the sclera of the human eye. Optionally, the plurality of treatment locations may be located anterior to the lens equator by no more than about 3 mm. The angle may open in response to the application of the energy to the plurality of treatment locations.

In some embodiments, the processor may be configured to fractionate energy delivered to the plurality of treatment locations. An amount of energy delivered to each of the plurality of treatment locations with an energy exposure may comprise no more than about 50% of a total amount of energy delivered to said each of the plurality of treatment locations. Optionally, the exposure may comprise an amount within a range from about 2% to about 50%, for example within a range from about 10% to 34%, of the total amount of energy delivered for said each of the plurality of treatment locations. The energy exposure may comprise a time within a range from about 1 millisecond (ms) to about 200 ms for each of the plurality of treatment locations. Each of the plurality of treatment locations may receive a plurality of exposures. A time between the plurality of energy exposures for said each of the plurality of treatment locations may be within a range from about three times (3×) or five times (5×) the exposure time to about 200 times (200×) the exposure time. A total amount of energy delivered to the eye with the plurality of treatment patterns to open the angle may be within a range from about 25 J to about 150 J.

In some embodiments, the plurality of treatment locations may be arranged to tension zonules coupled to a lens of the eye to urge an equator of the eye radially outward to allow an iris of the eye to move posteriorly to increase the angle. Optionally, a spherical refraction of the eye (sphere of eyeglass prescription) may change by no more than about 1 Diopters in response to the tensioning of the zonules, for example a change of no more than about 0.5 D. The plurality of treatment locations may be arranged to increase an anterior chamber depth extending between the cornea of the eye and the lens of the eye by an amount within a range from about 0.5 mm to about 2 mm in response to tensioning of the plurality of zonules. In many embodiments, the plurality of treatment locations may comprise locations on a sclera of the eye anterior to a lens equator of the eye. The applied energy may be configured to shrink tissue at the plurality of locations to tension the zonules.

In some embodiments, the processor may be configured with instructions to receive an input corresponding to a location of a lens equator on the sclera or the location of the limbus. The processor may be configured to determine the plurality of locations in response to the input. Optionally, the plurality of locations may be offset radially inward from the input location corresponding to the lens equator on the sclera. In some embodiments, the plurality of treatment locations may correspond to an annular treatment pattern located at least 2.5 mm radially outward from the limbus of the eye and anterior to the lens equator to open the iridocorneal angle in response to the annular treatment pattern. Optionally, the treatment locations may be within a range from about 1 mm to about 10 mm and optionally within a range from about 2 mm to about 6 mm.

In some embodiments, the processor may be configured with instructions to shrink tissue with at least a portion of a first annular treatment pattern prior to shrinking tissue with at least a portion of a second annular treatment pattern. The first annular treatment pattern may comprise a first plurality of spaced apart annular treatment patterns and the second annular treatment pattern may comprise a second plurality of spaced apart annular treatment patterns. The first plurality of spaced apart annular treatment patterns may comprise angularly separated spaced apart treatment patterns and the second plurality of annular treatment pattern may comprise angularly separated spaced apart treatment patterns. The first plurality of spaced apart annular treatment patterns may comprise radially separated spaced apart treatment patterns and the second plurality of annular treatment pattern may comprise radially separated spaced apart treatment patterns.

In some embodiments, the processor may be configured with instructions to repeatedly deliver the energy to each the plurality of treatment locations with a time delay to fractionate delivery of energy to said each of the plurality of treatment locations. The time delay may be within a range from about 10 millisecond (ms) to about 60 seconds. Optionally, the time delay may be within a range from about 100 ms to about 30 seconds, for example within a range from about 500 ms to about 15 seconds such as a range from about 1 second (s) to about 10 seconds.

In some embodiments, the processor coupled to the energy source and the scanner may be configured with instructions to heat tissue at the plurality of treatment locations to a temperature within a range from 60 to 70 degrees Centigrade at a depth within a range from 50 to 400 µm at each of the plurality of treatment locations along the first annular pattern and the second annular pattern. A majority or all of the treatment energy of the first treatment pattern may be located within 2.5 mm of the limbus and a majority of treatment energy of the second pattern may be located within 6.0 mm of the limbus. The first annular treatment pattern and the second annular treatment pattern may be configured to open an iridocorneal angle of the eye by an amount within a range from 1 to 6 degrees.

In some embodiments, the first annular treatment pattern extends at least about 30 degrees around the optical axis of the eye and the second annular treatment pattern extends at least about 30 degrees around the optical axis of the eye. Alternatively, the first annular treatment pattern extends at least about 40 degrees around the optical axis of the eye and the second treatment pattern extends at least about 40 degrees around the optical axis of the eye.

In some embodiments, the first annular treatment pattern and the second annular treatment pattern may be arranged avoid heating tissue overlaying the Schlemm's canal. For example, the annular treatment patterns may be no more closer than 1.5 mm to Schlemm's canal. In many embodiments, the first annular treatment pattern and the second annular treatment pattern may comprise circular, oval, elliptical, egg-like, non-circular, non-elliptical, or asymmetrical, shapes patterned so to correspond to the shape of Schlemm's canal or the limbus.

In some embodiments, the energy source may be one or more of a pulsed laser or a continuous laser. For example, the energy source may be a laser having a wavelength within a range from about 1.4 to 2.3 µm, for example from about 1.9 to 2.1 or 2.3 µm, or 1.4 to 1.6 µm. In some embodiments, the energy delivery system may comprise a scanner, an optical imaging system, a mask, a hand-held probe, or an ultrasound lens.

The processor may be configured with instructions to scan the laser beam in an annular pattern on the sclera one or more times, for example scanning the sclera with two repetitions of the annular pattern. The processor may be configured with instructions to provide a user interface comprising one or more fields and to receive input data from a user which is used to configure and adjust the plurality of treatment locations generated by the processor. In some embodiments, the processor may be configured with instructions to sequentially direct energy to the plurality of locations in response to a radial position of the plurality of locations. Optionally, the radially outward locations of the plurality of locations may be delivered to the sclera of the eye before radially inward locations to generate an anterocentrifugal force to the lens of the eye.

In some embodiments, the processor may be configured with instructions to receive user input corresponding to angles and radial locations. The use input may correspond to a partial annular treatment at a radial location to avoid insertion muscles coupled to the sclera of the eye.

In another aspect, a system to treat glaucoma of an eye is provided. The system comprises an energy source and a handpiece coupled to the energy source. The handpiece comprises an eye contacting surface to couple to the eye and a plurality of energy releasing elements disposed at a plurality of locations to release energy to the eye at a plurality of treatment locations, the plurality of treatment locations located at least about 2 mm radially outward from a limbus and corresponding to an angle within a range from about 30 degrees to about 360 degrees around a sclera of the eye. In particular embodiments the treatment locations are on the sclera, for example in concentric annuli or in annuli around the limbus that correspond to the shape of the limbus of an eye. In some examples the plurality of energy releasing elements are positioned on the eye contacting surface to apply the energy to the treatment locations, for example within 2-6 mm posterior from the limbus, for example 2-5 mm. The handpiece is configured to deliver the energy to the plurality of treatment locations to open an iridocorneal angle of the eye by an amount within a range from about 0.5 degrees to about 10 degrees.

In another aspect, a method for treating glaucoma of an eye is provided. The method comprises delivering energy to a plurality of treatment locations of the eye, the plurality of treatment locations located at least about 2 mm radially outward from a limbus and corresponding to an angle within a range from about 30 degrees to about 360 degrees around a sclera of the eye, wherein the energy delivered to the plurality of treatment locations opens an angle of the eye by an amount within a range from about 0.5 degrees to about 10 degrees.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings. The drawings are intended only as examples of specific embodiments and are not limiting as to the scope of the invention.

FIG. 5A depicts the distal treatment end of a handheld probe having an energy delivering face that is to be placed against the eye to apply treatment energy from light outputs to a predetermined set of treatment locations more than 2 mm posterior to the limbs. The depicted light outputs are arranged in concentric annuli around the center or the face of the probe. FIG. 5B is a perspective side view of the probe, and FIG. 5C is a schematic diagram of the probe and its light source, coupler, manifold and distal end.

FIGS. 23A-23C show an embodiment of a handheld probe that can be used for juxtacanalicular treatments.

DETAILED DESCRIPTION

A better understanding of the features and advantages of the present disclosure will be obtained by reference to the following detailed description that sets forth illustrative embodiments, in which the principles of embodiments of the present disclosure are utilized, and the accompanying drawings.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the method and apparatus of the present disclosure provided herein without departing from the spirit and scope of the invention as described herein. The embodiments disclosed herein can be combined in one or more of many ways to provide improved methods and apparatus for treating the eye. The treated ocular tissue, or membranes or pathological transformations thereof, may comprise one or more of corneal tissue, lens tissue, scleral tissue, vitreal tissue, or zonulae extending between the lens capsule and the ora serrata.

As used herein like characters identify like elements. "A and/or B" encompasses one or more of A or B, and combinations thereof such as A and B.

The embodiments as disclosed herein provide improved methods and apparatus for the treatment of glaucoma. The treatments and apparatus disclosed herein can be combined with many known methods and apparatus for treatment. For example, the methods and apparatus as disclosed herein can be combined with one or more other glaucoma therapies. Alternatively, or in combination, the methods and apparatus as disclosed herein can be combined with one or more presbyopia and/or refractive therapies.

The methods and apparatus disclosed herein are well suited for combination with other treatments such as surgical implants, intraocular lenses, laser in situ keratomileusis (LASIK), photorefractive keratectomy, small incision lens extraction (SMILE), crosslinking and corneal crosslinking.

Anatomy of the Eye

Figure 1:
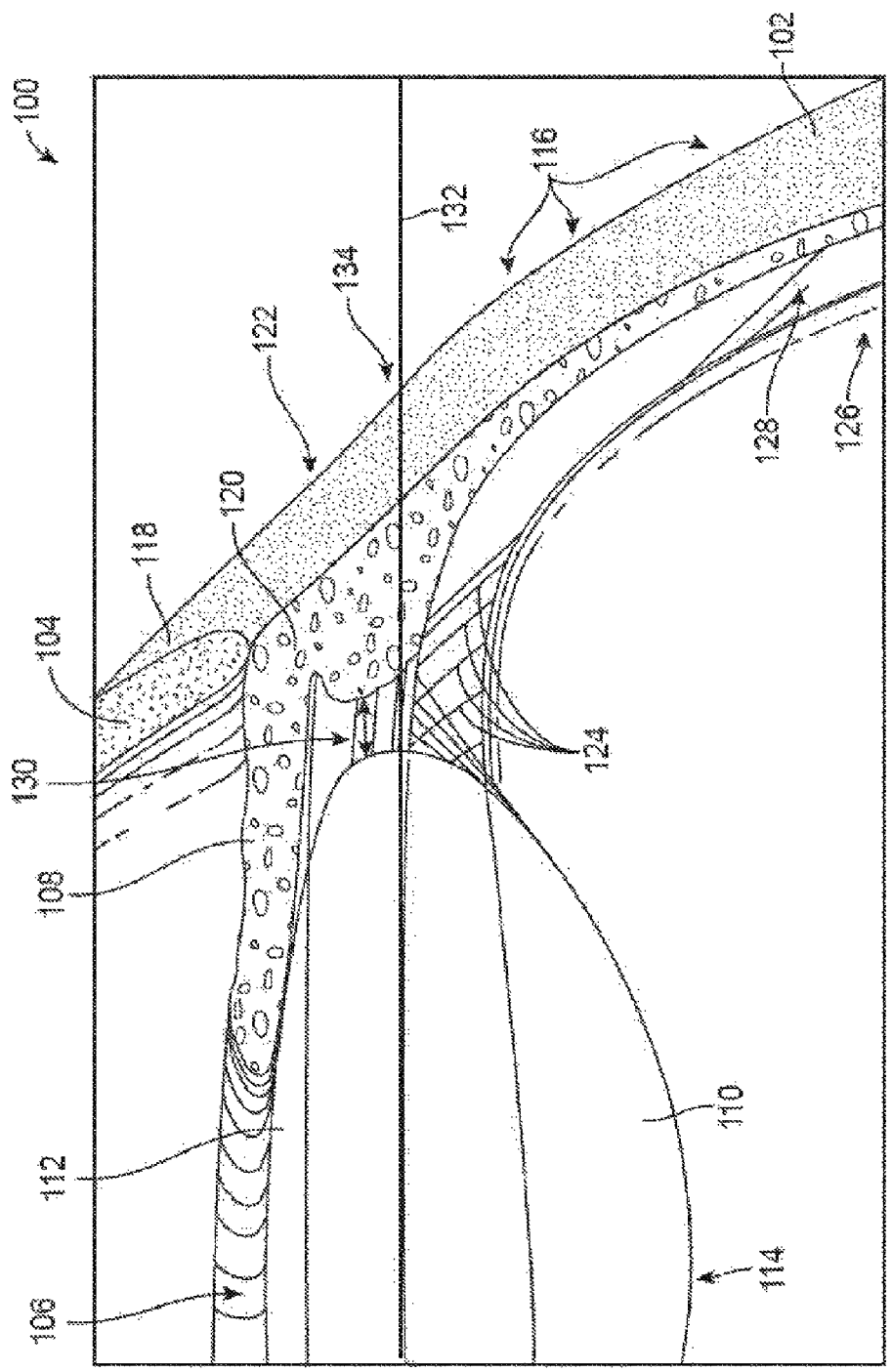
FIG. 1 schematically illustrates the anatomy of the anterior chamber of the eye.

FIG. 1 illustrates an eye 100, in accordance with embodiments. The eye 100 includes a sclera 102, a cornea 104, a pupil 106, an iris 108, and a lens 110 within a lens capsule, the lens capsule including a lens capsule anterior surface 112 and a lens capsule posterior surface 114. The sclera is lined by a conjunctiva 116 and includes a sclera spur 118 adjacent the cornea 104. A ciliary body 120 is adjacent the ciliary body sclera region 122. The ciliary body 120 is connected to the lens 110 by vitreal zonules 124 and to the ora serrata 127 by the posterior vitreal zonules 128 (hereinafter "PVZ"). A circumlental space 130 (hereinafter "CLS") is defined by the distance between the lens 110 and the ciliary body 120 along a lens equator plane 132, the lens equator plane 132 passing through an equatorial sclera region 134.

The term "anterior" as used with respect to the eye means toward the front of the eye and the cornea, while the term "posterior" means toward the back or the eye and retina, and away from the cornea. The marginal circumference of the lens, where anterior and posterior surfaces of the lens meet, are known as the equator of the lens. The equator of the lens is encircled by the ciliary processes of the ciliary body and held in location by zonules. Locations may be radially outward from the limbus if they are posterior to the limbus. Locations are radially inward from the limbus if they are anterior to the limbus. Locations are radially inward from the equator of the lens if they are anterior to the plane in which the circumferential equator of the lens lies. In some embodiments, the locations may be a substantially fixed distance from the reference point on the limbus or generally a fixed distance from and anterior to the plane through the equator of the lens.

Glaucoma

Figure 2A:
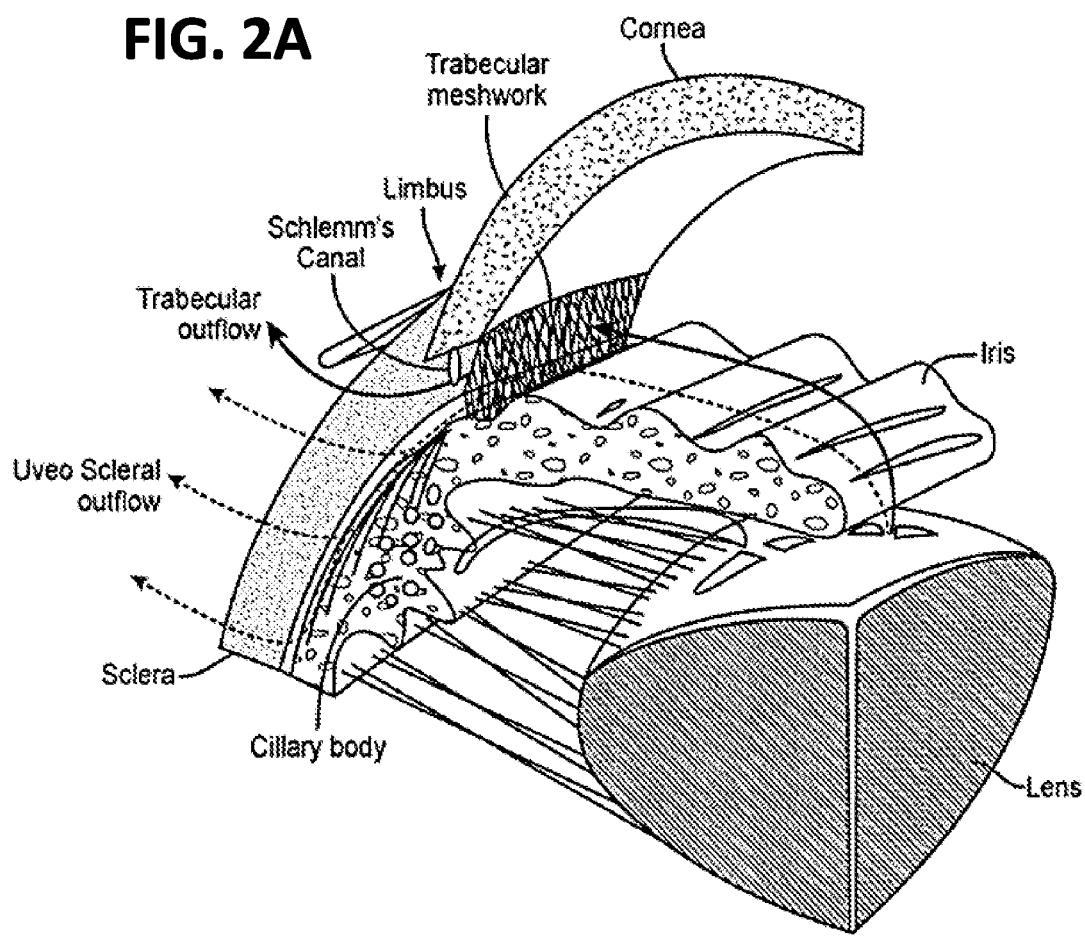
FIG. 2A schematically illustrates common fluid outflow paths of the eye including the location of the limbus and Schlemm's Canal.

FIG. 2A illustrates common fluid outflow paths of the eye including the location of the limbus and Schlemm's canal. Glaucoma may be caused by obstruction to one or more fluid outflow paths. Aqueous humor is produced by the ciliary body processes and secreted into the posterior chamber. From there it flows through the narrow cleft between the anterior surface of the lens and the posterior surface of the iris, into the anterior chamber. The fluid may exit the anterior chamber via the trabecular outflow route and/or the uveoscleral outflow route into the anterior chamber angle (drainage canal) and out of the eye. The fluid may alternatively or in combination exit the anterior chamber through the iris surface and capillaries. In the trabecular outflow route, the fluid exits the anterior chamber and travels out of the eye via the trabecular meshwork. The fluid then drains directly into Schlemm's canal, an endothelial cell-lined channel at the limbus (where the cornea and sclera meet), or indirectly through collector channels and then into the episcleral venous system. In the uveoscleral outflow route, aqueous humor seeps through, around, and between tissues, including the supraciliary space, ciliary muscle, suprachoroidal space, choroidal vessels, emissarial canals, sclera, and lymphatic vessels, but does not have a well-defined structural pathway like the trabecular route. Blockage of one or more outflow pathways may increase intraocular pressure (IOP) and cause glaucoma. Reduction of IOP may treat glaucoma. Common mechanisms by which these outflow pathways are blocked include closing of the anterior chamber angle, blockage of pores and/or vacuoles in Schlemm's canal, blockage (and/or collapse) or Schlemm's canal, blockage of uveo-sclera outflow (for example blockage of vacuoles or pores of the perilimbic sclera), and any combination thereof.

Narrow Angle Glaucoma

Figure 2B:
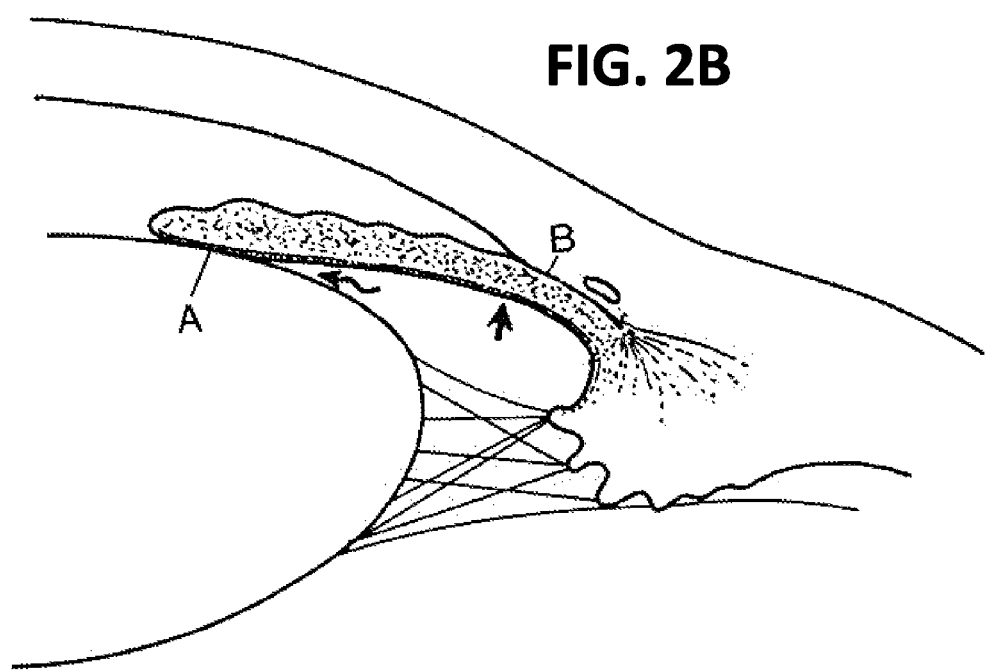
FIG. 2B schematically illustrates a type of angle closure glaucoma in which a functional block between the lens and iris (A) leads to increased pressure in the posterior chamber (arrows) with forward shift of the peripheral iris and resulting narrowing of the anterior chamber angle (B).

Narrowing of the iridocorneal angle can cause angle closure glaucoma. Pupillary block, with forward bowing of the iris, is a common cause of angle closure glaucoma that is depicted in FIG. 2B. A functional block between the lens and iris (A) lead to increased pressure in the posterior chamber with forward shift of the peripheral iris and closure of the anterior chamber angle (B). Angle closure glaucoma may also occur without pupillary block. For example, the depth of the anterior chamber tends to narrow with age which can predispose one to develop a narrow angle glaucoma. In another non-limiting example, the iris may adhere to the trabecular meshwork and narrow the angle following inflammation, neovascularization, or endothelial proliferation.

Angle-Opening Method

Figure 3A:
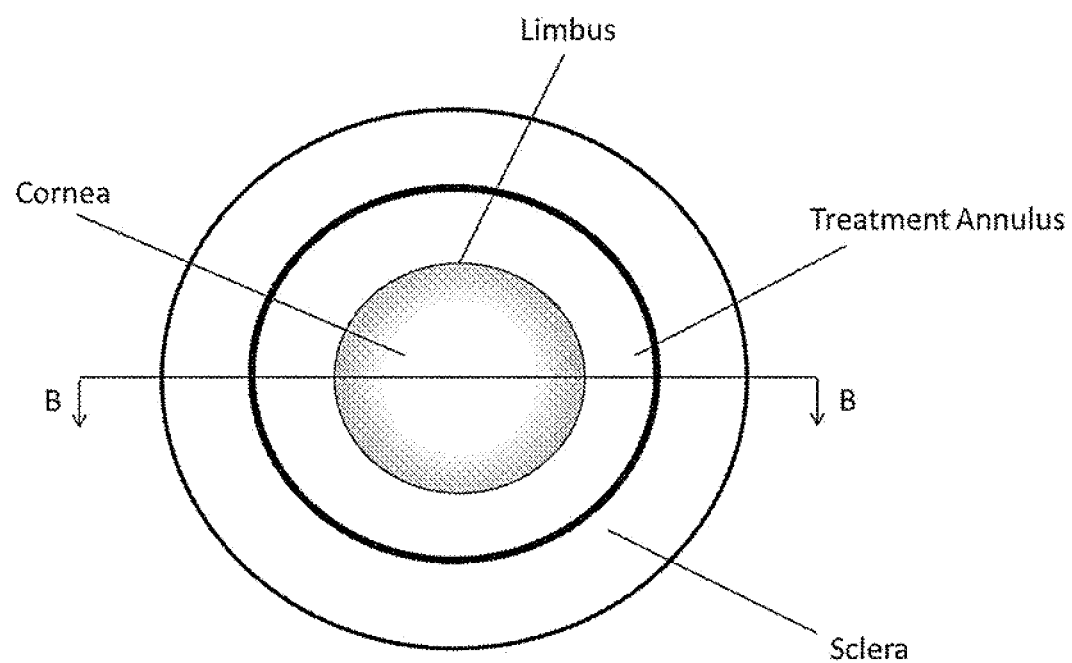
FIG. 3A illustrates a treatment pattern which may be used to open a narrow iridocorneal angle of the eye.

FIG. 3A illustrates a treatment pattern which may be used to open a narrow iridocorneal angle. Treatment may be patterned in an annulus in the posterior sclera at a location anterior to (i.e. radially inward of) the lens equator. Without being bound by theory, it is believed that shrinkage treatment near the lens equator induces tension in the ciliary processes. The ciliary processes then move radially outward (and/or posteriorly), and in doing so, pull on the zonules to flatten the lens. This flattening induces the iris to move posteriorly towards the lens and open the iridocorneal angle, to improve aqueous outflow and reduce intraocular pressure for treatment of narrow angle glaucoma.

The treatment annulus may comprise a single continuous treatment annulus. Alternatively, the treatment annulus may comprise a single discontinuous treatment annulus with a predetermined amount of space between "dashes" or "spots" of treatment along the treatment annulus (for example as described in FIGS. 5A-5B). In some instances, the treatment annulus may comprise a plurality of treatment annuli, for example treatment two or more treatment annuli posterior to the limbus and anterior to the lens equator, such as annuli 2-6 mm posterior to the limbus. The treatment annulus may have a pre-determined width which is made up by the plurality of treatment annuli. The plurality of annuli may be overlapping or non-overlapping. For example, the plurality of annuli may be overlapping to generate the treatment annulus with a width greater than the spot size of the energy beam (e.g. laser beam). The plurality of annuli may be non-overlapping, with a pre-determined radial distance between each of the plurality of annuli making up the treatment annulus.

The treatment annulus may be located more than about 2 mm radially outward of the limbus and/or at least or about 1 mm radially inward of the lens equator. The treatment annulus may include a plurality of treatment locations as described herein. The plurality of treatment locations may correspond to an annular treatment pattern located at least 2.5 mm radially outward from the limbus of the eye and anterior to the lens equator. Optionally, the plurality of treatment locations may be located anterior to the lens equator by no more than about 3 mm.

The iridocorneal angle ("the angle") may open in response to the plurality of treatment locations by an amount within a range from 1 to 6 degrees, for example within a range of 2 to 5 degrees, such as within a range of 3 to 4 degrees. The angle may open about 1 degree, about 2 degrees, about 3 degrees, about 4 degrees, about 5 degrees, or about 6 degrees.

The treatment annulus energy may be configured to shrink tissue at the plurality of treatment locations to tension the zonules. The plurality of treatment locations may correspond to an angle within a range from about 30 degrees to about 360 degrees around a sclera of the eye, for example within a range from about 90 degrees to about 360 degrees, within a range from about 90 degrees to about 180 degrees, or within a range from about 180 degrees to about 360 degrees. The plurality of treatment locations may correspond to an angle of about 30 degrees, about 45 degrees, about 60 degrees, about 75 degrees, about 90 degrees, about 180 degrees, about 270 degrees, or about 360 degrees. For example, FIG. 3D shows a plurality of arcuate, substantially parallel treatment patterns at different distances d1, d2, and d3 from the optical center of the cornea. In the illustrated examples, d1 is 6 mm from the limbus L, d2 is 4 mm from the limbus L, and d3 is 2 mm from the limbus L. Each of the parallel curves may be at a substantially fixed normal distance from the limbus L, and the parallel curves may be at a fixed distance from each other. The curves in FIG. 3D extend 90 degrees around the optical axis OA of the eye, and one or more of these sector treatments may be used to extend the treatment zone.

The translocation vector of sequential tracks near each other is from the first toward the last track. To promote outward movement of treated scleral tissue, treatment locations may be treated by ping-ponging 180° from one treatment location to the next. For example, a 360° circumferential limbus may divided into equal arcuate segments (such as 36 arcuate segments). The treatment locations may, for example, sequentially be at 0°, 180°, 10°, 190°, 20°, 200°, 30°, 210°, 40°, 220°, etc. through the entire 360° annulus.

The plurality of treatment locations may comprise at least a first annular treatment pattern and a second annular treatment pattern. The annular pattern is ring-like but need not be internally and externally bounded by circles. Other polygonal shapes can also bound the annulus, and the annulus includes portions of the annulus that are recognizable as portions of the annulus. The annulus surrounds or partially surrounds the optical axis, limbus, or other structure of the eye. For example, the first annular treatment pattern may extend at least about 30 degrees around the optical axis of the eye and the second annular treatment pattern for example extend at least about 30 degrees around the optical axis of the eye. The first annular treatment pattern may for example extend at least about 40 degrees around the optical axis of the eye and the second treatment pattern may for example extend at least about 40 degrees around the optical axis of the eye. The first and second treatment patterns may subtend the same angles (adjacent treatment patterns) or different angles (offset treatment patterns), or they may partially overlap.

The energy delivery system may be configured to deliver the energy to the plurality of treatment locations to open an angle of the eye by an amount within a range from about 0.5 degrees to about 10 degrees. The angle may open by an amount within a range from about 1 degree to about 10 degrees, within a range from about 2 degrees to about 9 degrees, within a range from about 3 degrees to about 8 degrees, within a range of about 4 degrees to about 7 degrees, within a range of about 5 degrees to about 6 degrees.

The eye may comprise a human eye and plurality of treatment locations may correspond to a surface area on the sclera. The surface area may be within a range from about 1 $mm^2$ to about 100 $mm^2$. The surface area may be located radially outward from the limbus on a sclera of the eye by at least about 2.5 mm and anterior to a lens equator on the sclera of the human eye.

The iris may open by the amount in response to the annular treatment pattern. Optionally, the amount may be within a range from about 1 mm to about 10 mm, for example within a range from about 2 mm to about 6 mm.

In some embodiments, a plurality of treatment locations may also be provided in a first juxtacanalicular annular pattern and a second juxtacanalicular annular pattern. A majority of the treatment energy of the first treatment pattern may be located within 1.5 mm of the Schlemm's canal and a majority of the treatment energy of the second pattern may be located within 1.5 mm of Schlemm's canal. The first annular treatment pattern and the second annular treatment pattern may be configured to open an angle of the eye by an amount within a range from 1 to 6 degrees. These treatment locations that are located 2 mm or less from Schlemm's Canal are referred to herein as "juxtacanalicular" treatment locations. For purposes of distinction, treatment locations that are on the sclera more than 2 mm from Schlemm's Canal are referred to as "paralimbal" treatment locations.

In yet other embodiments, a plurality of treatment locations may also be provided within 1 mm of the collector channels or ostia thereof to increase outflow through the collector channels.

For any of these treatment patterns, a processor may be coupled to the energy source and the scanner may be configured with instructions to heat tissue at the plurality of treatment locations, providing an automated or computer-implemented treatment that more precisely delivers energy to the preselected treatment locations. The treatment locations may be heated to a temperature within a range from 60 to 70 degrees Centigrade at a depth within a range from 50 to 400 µm at each of the plurality of treatment locations along the first annular pattern and the second annular pattern. The plurality of treatment locations, for example a first annular treatment pattern and a second annular treatment pattern, may be arranged avoid heating tissue overlaying Schlemm's canal or the collector channels, and the pattern may avoid underlying anatomic structures such as the insertions of intraocular muscles. In some embodiments computer implementation of automated treatment patterns can achieve controlled heating of specific locations to achieve the desired outcomes.

At least a portion of a first annular treatment pattern may be shrunk prior to shrinking tissue with at least a portion of a second annular treatment pattern. The first annular treatment pattern may include a first plurality of spaced apart annular treatment patterns and the second annular treatment pattern may include a second plurality of spaced apart annular treatment patterns. The first plurality of spaced apart annular treatment patterns may include angularly separated spaced apart treatment patterns and the second plurality of annular treatment pattern may include angularly separated spaced apart treatment patterns. The first plurality of spaced apart annular treatment patterns may comprise radially separated spaced apart treatment patterns and the second plurality of annular treatment pattern may comprise radially separated spaced apart treatment patterns.

The energy delivered to the plurality of treatment locations may be fractionated as described herein. An amount of energy delivered to each of the plurality of treatment locations with an energy exposure may comprise no more than about 50% of a total amount of energy delivered to each of the plurality of treatment locations. Optionally, said exposure may comprise an amount within a range from about 2% to about 50% for said each of the plurality of treatment locations. Optionally, said amount may be within a range from about 10% to 34% of the total amount of energy delivered for said each of the plurality of treatment locations.

The energy exposure may be delivered within a range from about 1 millisecond (ms) to about 200 ms for said each of the plurality of treatment locations. Each of the plurality of treatment locations may receive a plurality of exposures. A time between the plurality of energy exposures for said each of the plurality of treatment locations may be within a range from about three times (3×) or 5 times (5×) the exposure time to about 200 times (200×) the exposure time.

A total amount of energy delivered to the eye with the plurality of treatment patterns to open the angle may be within a range from about 25 J to about 150 J. Energy may be repeatedly delivered to each the plurality of treatment locations with a time delay to fractionate delivery of energy to said each of the plurality of treatment locations. The time delay may be within a range from about 10 millisecond (ms) to about 60 seconds. Optionally, the time delay may be within a range from about 100 ms to about 30 seconds and optionally within a range from about 500 ms to about 15 seconds and optionally within a range from about 1 second (s) to about 10 seconds.

The treatment annulus (or annuli) may be circular as shown. Alternatively, the annulus may be oval, elliptical, egg-like, non-circular, non-elliptical, asymmetrical, or patterned to mimic (e.g. correspond to) the shape of Schlemm's canal or the limbus which may have a non-regular shape. The annuli may be shaped roughly the same as one another or may be differently shaped.

The plurality of treatment locations may be arranged to tension zonules coupled to a lens of the eye to urge an equator of the eye radially outward to induce an iris of the eye to move posteriorly to increase the angle. Optionally, a spherical refraction of the eye (sphere of eyeglass prescription) may change by no more than about 1 Diopters, for example no more than 0.5 Diopters, in response to the tensioning of the zonules.

The plurality of treatment locations may be arranged to increase an anterior chamber depth extending between a cornea of the eye and a lens of the eye by an amount within a range from about 0.5 mm to about 2 mm in response to tensioning of the zonules.

The plurality of treatment locations may for example comprise a plurality of spaced apart treatment annuli. For example, the plurality of treatment locations may comprise an inner treatment annulus and an outer treatment annulus located radially outward of the inner treatment annulus. The angle-opening treatment locations are radially outward from the limbus in the sense that they are spaced farther from the optical axis of the eye, and in some embodiments may be a fixed distance posterior to the limbus and the optical axis of the eye. The angle-opening treatment locations are radially inward from the equator of the lens in that they are spaced closer to the optical axis of the eye, and in some embodiments may be a fixed distance from and anterior to the plane through the equator of the lens. The term "anterior" as used with respect to the eye means toward the front of the eye and the cornea, while the term "posterior" means toward the back or the eye and retina, and away from the cornea.

The angle-opening treatment locations may be spaced to lie radially inward of the lens equator and/or radially outward of the limbus. For example, the treatment locations may be arranged to form a single annulus located radially inward of the lens equator. The treatment locations may provide light energy to a portion of the eye, for example the sclera, that is anterior to (e.g. radially inward of) the lens equator. In some embodiments, the annulus is spaced to provide the light energy in a circular pattern a fixed distance from the limbus or equatorial plane, such treatment locations apply energy to the eye a fixed distance from the limbus or equatorial plane. In other embodiments the annulus is spaced a variable distance from the limbus or equatorial plane, for example such that the annulus is elliptical or ovoid or another irregular shape. The shape of the annulus may be determined based on the eye anatomy of a particular subject, for example a subject having an irregularly shaped or asymmetric limbus. The treatment locations may be symmetric about a central point or about a central plane that bisects the annulus. In other embodiments they may be asymmetric with respect to the central point or central plane.

The order of treatment of the annuli may be based on the direction, or vector, of movement desired. For example, to move or translocate the eye's center of mass outward and anteriorly (to flatten the lens and open a narrow angle), the outer treatment annulus may be treated before the inner treatment annulus such that the direction of movement of the eye moves along the vector created by the direction of treatment.

Figure 3B:
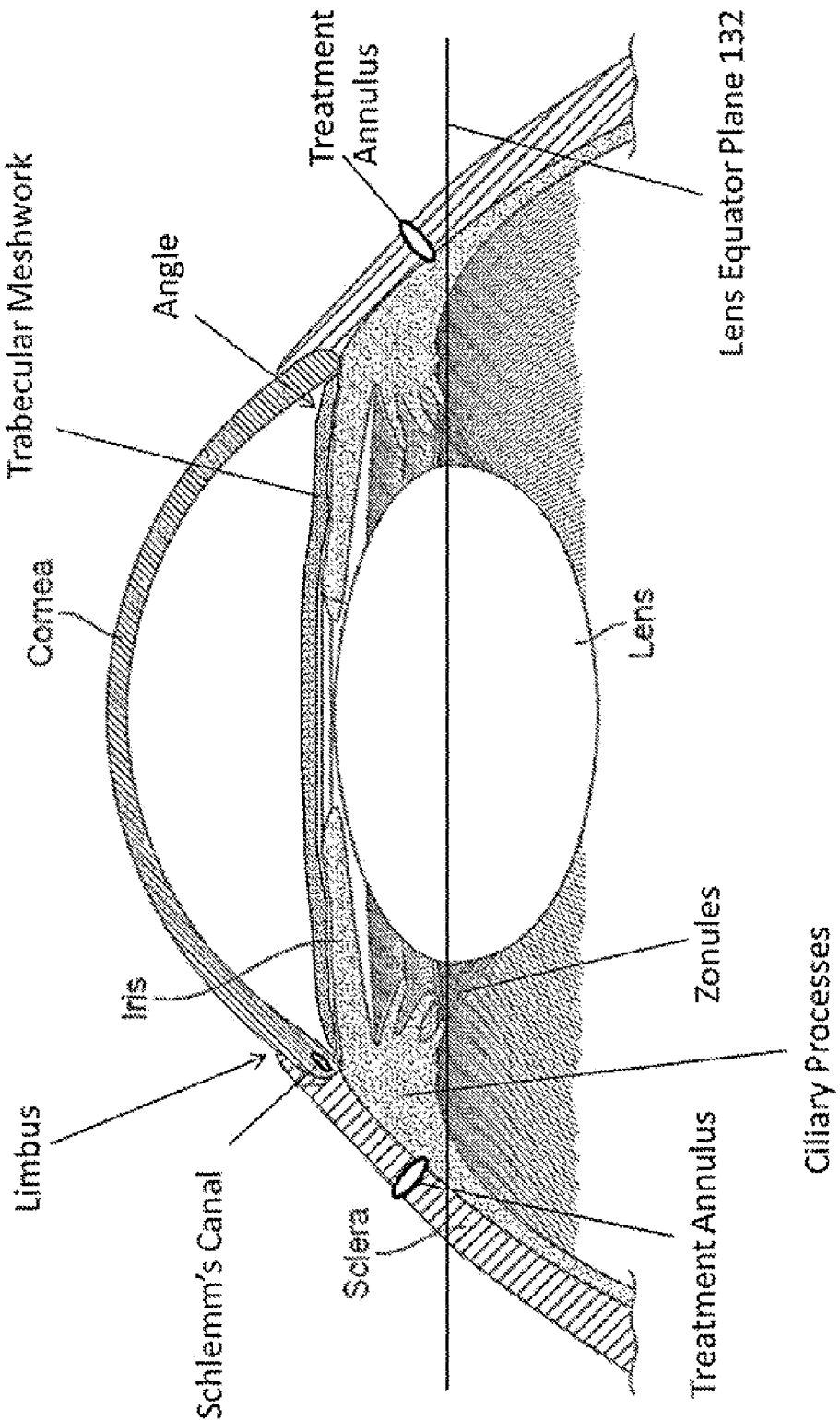
FIG. 3B shows a cross-section of the eye of FIG. 3A taken along line B-B with treatment annuli located anterior to the lens equator.
Figure 3C:
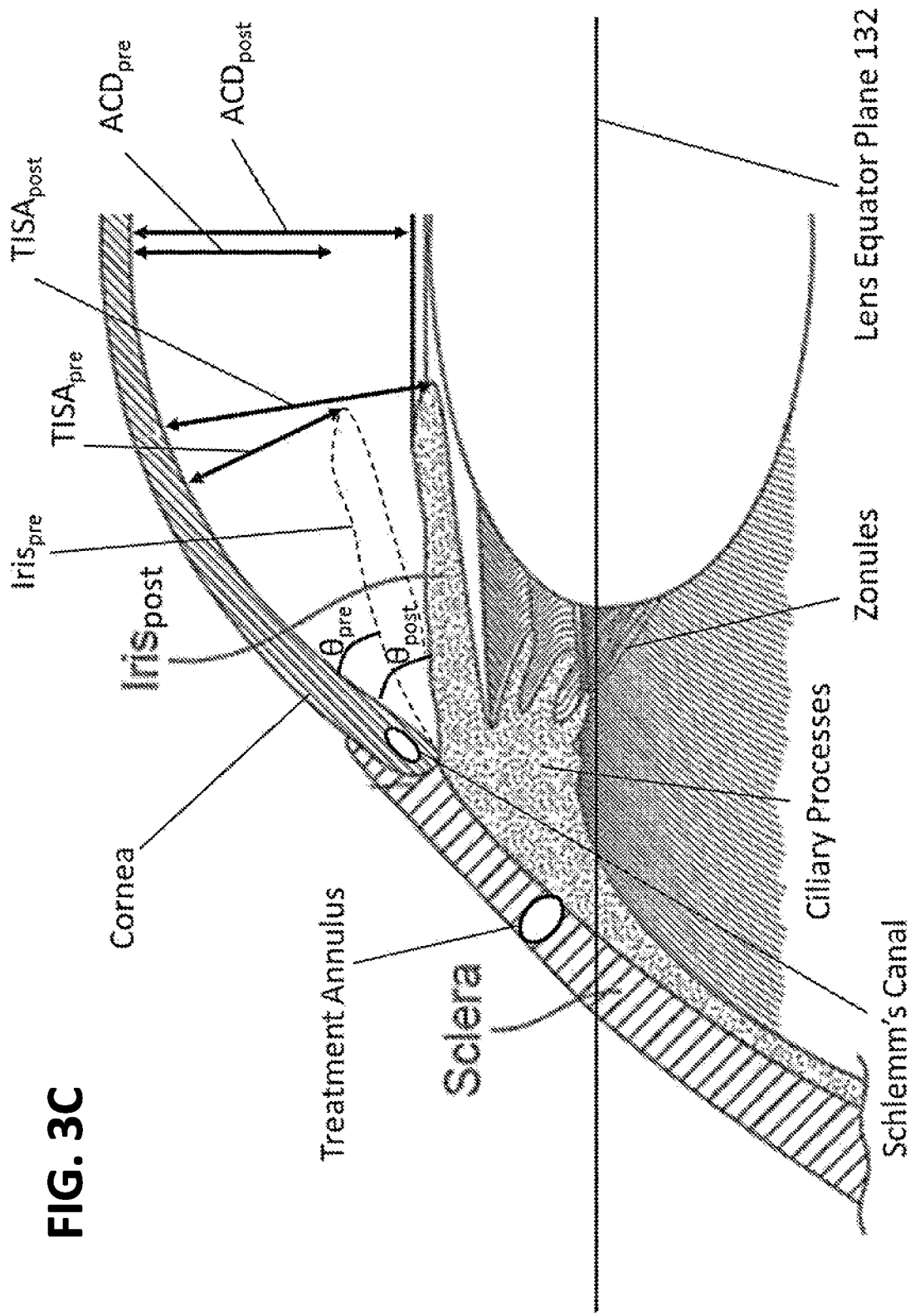
FIG. 3C is an enlarged view of the left half of FIG. 3B, illustrating the movement of the iris and an increase in the angle θ of the iridocorneal angle in response to the angle-opening method disclosed herein. Treatment anterior to the equator increases the anterior chamber depth (ACD), pupil-anterior chamber depth (Pupil-ACD), and trabecular iris space area (TISA).
Figure 3D:
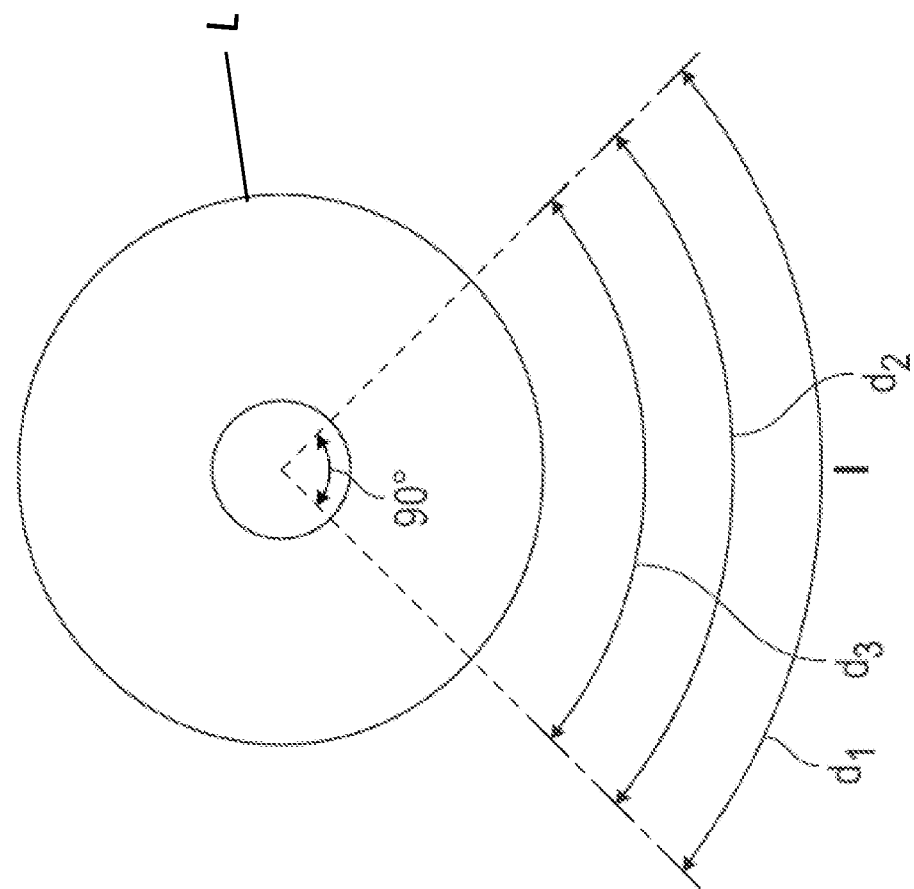
FIG. 3D schematically illustrates several angle-opening treatment patterns applied to the sclera, anterior to the equator of the lens, at different distances d1, d2 and d3 from the limbus L in a 90-degree treatment sector.

FIG. 3B shows a cross-section of the eye of FIG. 3A taken along line B-B of FIG. 3A with a treatment annulus located radially outward of the limbus and inward of the lens equator. FIG. 3C shows a magnified view of the left half of FIG. 3B. Shrinkage of the tissue within the treatment annulus may generate sufficient strain within the scleral tissue surrounding the treatment locations to pull on the ciliary processes. The ciliary processes may in turn "pull" on the zonules, leading to flattening of the lens and iris and opening of the iridocorneal angle, thereby improving aqueous outflow for treatment of glaucoma. As illustrated in FIG. 3C, the angle $\theta$ (the iridocorneal angle) increases from the pretreatment angle ($\theta_{pre}$) to the posttreatment angle ($\theta_{post}$) thereby opening the outflow tract through the trabecular meshwork and Schlemm's canal.

The extent of angle-opening may be approximated using full-scale extended Trabecular Iris Space Area measurements ("TISA-750"). As shown in FIG. 3C, the $TISA_{pre}$ measurement may be measured from the tip of the iris to the cornea for the pre-operative angle approximation. The $TISA_{post}$ measurement may be measured from the tip of the iris to the cornea for the post-operative angle approximation. The change in TISA measurement from pre-op to post-op is proportionally related to the change in angle and a change in TISA may be measured to monitor the change in angle. The change in anterior chamber depth ("$ACD_{pre}$" to "$ACD_{post}$") may be used to determine the extent of lens flattening.

The processor may be configured with instructions to receive an input corresponding to a location of a lens equator on the sclera. The processor may be configured to determine the plurality of angle-opening locations in response to the input. Optionally, the plurality of angle-opening locations may be offset radially inward from the input location corresponding to the lens equator on the sclera. The processor may be configured with instructions to scan the laser beam with an annular pattern on the sclera; to scan the sclera with two repetitions of the annular pattern; to provide a user interface comprising one or more fields and to receive input data from a user which is used to configure and adjust the plurality of treatment locations generated by the processor; and/or to sequentially direct energy to the plurality of locations in response to a radial position of the plurality of locations.

Optionally, the radially outward locations of the plurality of locations may be delivered to the sclera of the eye before radially inward locations to generate an antero-centrifugal force to the lens of the eye. The processor may be configured with instructions to receive user input to corresponding to angles and radial locations. The use input may correspond to a partial annular treatment at a radial location to avoid insertion muscles coupled to the sclera of the eye.

Figure 4A:
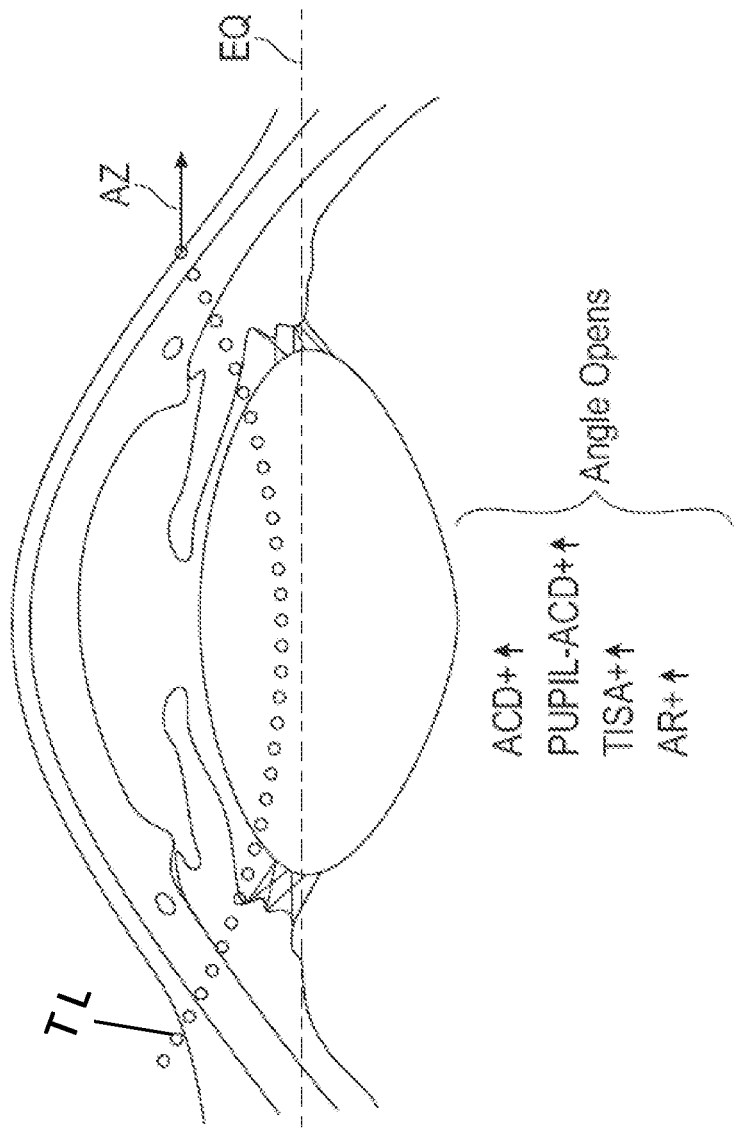
FIG. 4A is a horizontal schematic cross-section of the eye viewed from above showing the equator of the lens that divides the anterior and posterior faces of the lens, and an example of the placement of treatment locations TL to the sclera to tighten the zonules of the eye and deepen the anterior chamber of the eye.

FIG. 4A schematically illustrates how treatment anterior to the equator and posterior to the limbus may improve narrow angle glaucoma. A plurality of treatment locations TL may be located within the sclera anterior to the lens equator. The plurality of treatment locations TL may for example be located at around 2-4 mm, for example 2-3 mm, posterior to the limbus. A laser may be used to deliver shrinkage energy to the plurality of treatment locations to shrink the scleral tissue at the plurality of treatment locations anterior to the lens equator. Shrinkage of the scleral tissue anterior to the lens equator is applied to induce tension in the anterior zonules (AZ) of the eye and open the iridocorneal angle as described herein. Treatment may also result in an increase in the anterior chamber depth ("ACD"), an increase in the pupillary-ACD ("P-ACD"; also referred to herein as the TISA distance), an increase in the Trabecular Iris Space Area ("TISA"), and/or an improvement in angle recession ("AR").

Figure 4B:
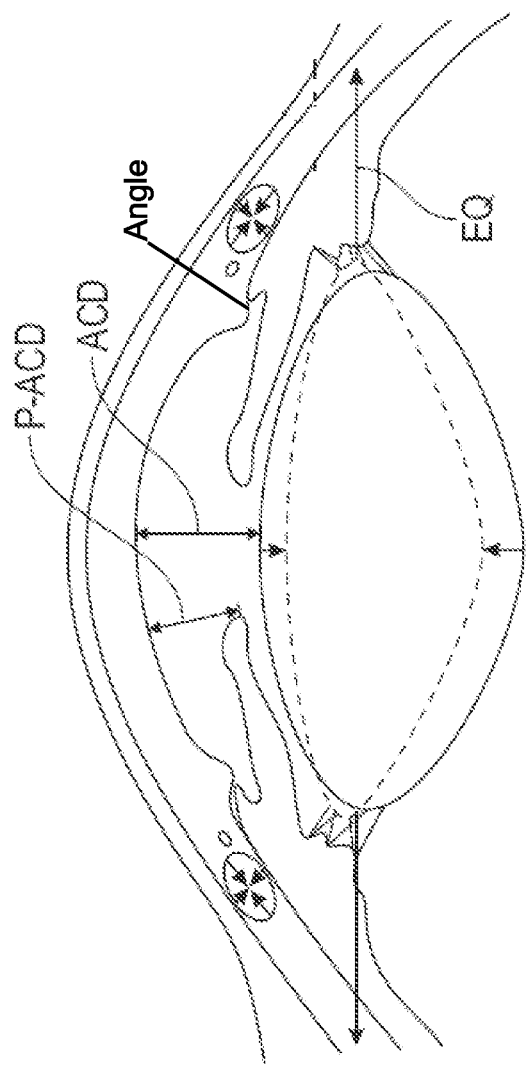
FIG. 4B is a view similar to FIG. 4A but illustrating the post-operative (PO) effect of the angle-opening treatment in which laser shrinkage of the sclera has induced a tightening of the zonules which exerts tension on the zonules at the equator of the lens, stretches the lens to narrow its anterior-posterior dimension, and increase the anterior chamber depth (ACD) and pupil-anterior chamber depth (P-ACD).

FIG. 4B schematically illustrates the effects of laser induced scleral shrinkage anterior to the lens equator. Scleral shrinkage anterior to the lens equator may cause the lens to stretch radially outward and flatten near the center. The pre-treatment lens is shown in solid lines, while the post-treatment stretched lens is shown in phantom (dashed lines). The illustrated treatment induced flattening of the lens moves the iris radially inward and posteriorly, to increase ACD, P-ACD, and/or the iridocorneal angle as described herein.

Figure 4C:
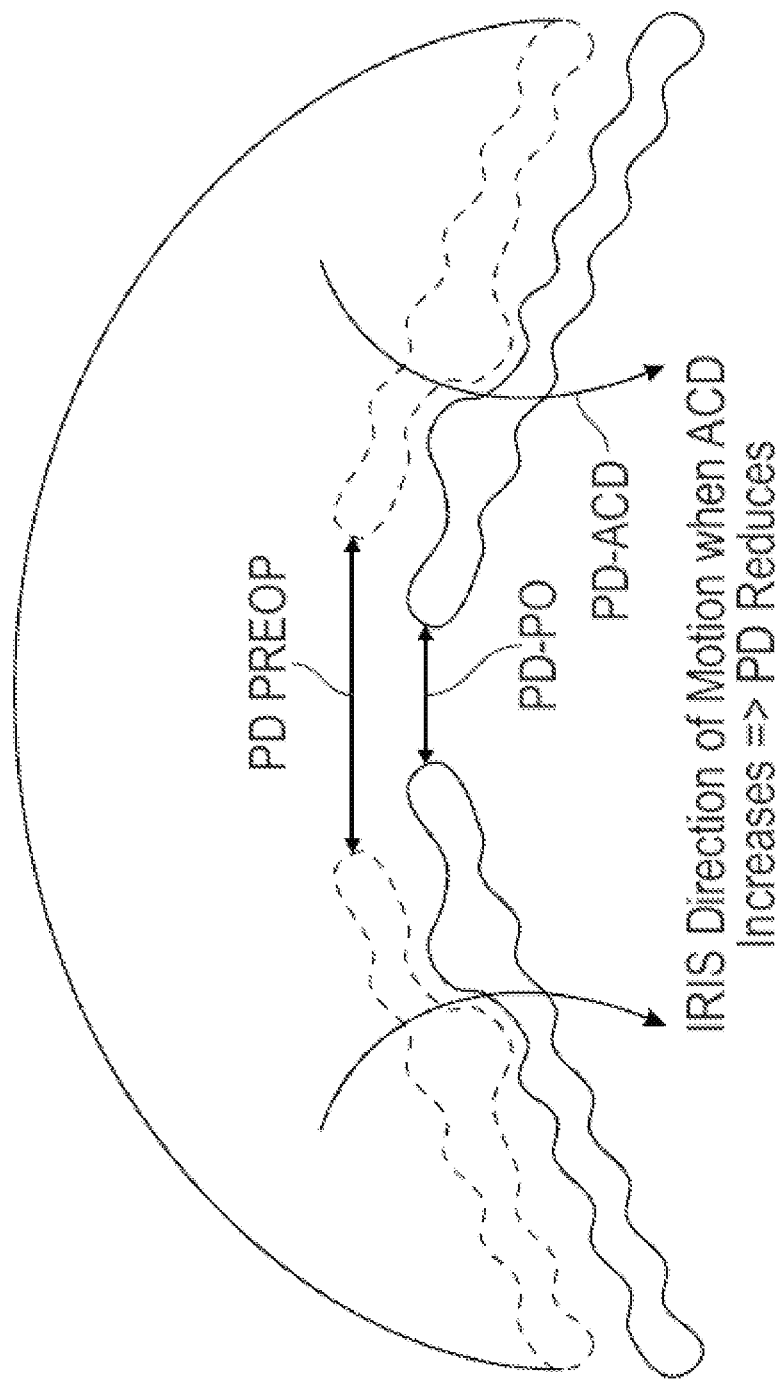
FIG. 4C further illustrates changes in eye dimensions induced by the angle-opening method.

FIG. 4C schematically illustrates opening of the iridocorneal angle via posterior movement of the iris. As the iris moves from a pre-operative, narrow angle configuration to a post-operative open angle configuration the anterior chamber depth ("ACD") may increase. Additionally, the pupillary distance ("PD") may decrease as the iris moves posteriorly and the ACD increases.

FIGS. 5A-5C show a handheld treatment probe 250 in the form of a substantially cylindrical handpiece 252 having a distal face 254 of for applying angle-opening energy to the eye in accordance with some embodiments of the disclosed systems and methods for opening the iridocorneal angle. Face 254 may be substantially flat and circular in cross-section or curved to conform to the corneal-scleral surface to which it is to be applied. Energy is supplied to probe 250 though a fiber optic bundle 56 that communicates with a proximal end of handpiece 252. An inner set of light outputs is arranged in a first inner annulus 258 on face 254, and an outer set of light outputs is arranged in a second outer annulus 260 on face 254. Annuli 258, 260 are concentric; the individual light outputs of inner annulus 258 are substantially equidistantly spaced from the geometric center C of face 254, and the individual light outputs of outer annulus 260 are substantially equidistantly spaced from geometric center C. The probable target annulus 262 on face 254 that would contact the limbus of a subject is shown in phantom. The individual light outputs of inner annulus 258 are substantially equidistantly spaced from the target annulus 262, and the individual light outputs of outer annulus 260 are substantially equidistantly spaced from target annulus 262, such that annuli 258, 260 and 262 are substantially concentric. Although the illustrated annuli are circular and the light outputs are equally spaced within each annulus, the annuli can be of other shapes (such as ellipses, polygons, or other irregular shapes) and the light outputs in each annulus may be unequally spaced from one another.

The probe directs angle-opening treatment energy to one or more pre-set locations on or inside the eye. In the illustrated embodiment of FIG. 5A, the light outputs on distal face 254 of handheld probe 250 includes a plurality of fixed light outputs that are positioned to direct treatment energy to desired locations on the sclera anterior to the limbus and posterior to the equator of the lens as described in this specification to open the iridocorneal angle. The light outputs may be oriented and/or spaced on the distal end of the handheld probe to target one or more regions of the eye and/or avoid treatment in one or more regions of the eye. For example, the light outputs may be arranged to form one or more annuli on the distal end of the probe. The one or more annuli may be spaced to lie radially inward of the lens equator and/or radially outward of the limbus when the probe is applied to the eye.

For example, the light outputs may be arranged to form a single annulus located radially inward of the lens equator. The annulus may be spaced such that it provides light energy to a portion of the eye, for example the sclera, that is anterior to (e.g. radially inward of) the lens equator. In some embodiments, the annulus is spaced to provide the light energy in a circular pattern a fixed distance from the center of the probe, such that the light outputs of the annulus apply energy to the eye a fixed distance from the center of the probe. In other embodiments the annulus is spaced a variable distance from the center of the probe, such that the light outputs are elliptical or ovoid. The light outputs may be symmetric about a central point or central plane that bisects the annulus. In other embodiments they may be asymmetric with respect to the central point or central plane.

The annulus may be spaced such that it provides light energy to a portion of the eye, for example the sclera, that is radially outward of (or posterior to) the limbus, for example more than about 2 mm radially outward of the limbus. Alternatively, the light outputs may be arranged to form two or more annuli located radially inward of the lens equator. The annuli may be spaced such that they provide light energy to a portion of the eye, for example the sclera, that is anterior to (e.g. radially inward of) the lens equator. The annuli may be spaced such that it provides light energy to a portion of the eye, for example the sclera, that is radially outward of (or posterior to) the limbus, for example more than about 2 mm radially outward of the limbus. The dashed line 262 in FIG. 5A represents an expected location of the limbus relative to the light outputs when the probe is applied to the eye. In the illustrated embodiment the annuli are both radially outward from the limbus and positioned a distance that would place them at the desired locations posterior to the limbus and anterior to the equatorial plane of the lens. In this way, the eye may be treated with the handheld probe to open a narrow angle of the eye as described herein.

It will be understood by one of ordinary skill in the art that the light outputs may be arranged in any location and/or pattern on the distal end of the probe to provide treatment to the desired location(s) of the eye. For example, alternatively or in combination, an annulus of light outputs may be provided radially inward of the annuli shown in FIG. 5A at a desired location to treat the sclera to generate areas of contraction as described herein. Alternatively, or in combination, the user may pattern the light outputs to avoid critical structures of the eye such as the vasculature or insertions of the intraocular muscles (such as the superior, inferior, medial and lateral rectus muscle insertions). For example, the pattern may be spaced a distance from the limbus that the pattern is unlikely to overlap with the muscle insertions, or the annular pattern can be interrupted at the superior, inferior, medial and lateral sectors where the muscles insert. In view of the different sizes, shapes and symmetries of the human limbus the position of the light outputs can be positioned so as to statistically be within a range of 2-6 mm, or alternatively a minimum distance or 2 mm or 3 mm to a maximum distance of 4 mm, 5 mm or 6 mm from the position of an average human limbus. Different probes of different dimensions may also be used depending on the size of the eye being treated and the dimensions of the limbus in a subject.

The light outputs may for example include a plurality of light sources such as laser diodes or light emitting diodes configured to emit light at a wavelength suitable for treating the eye as described herein. Alternatively, the plurality of light sources may comprise openings in a mask configured to transmit light to desired treatment locations and block light at other treatment locations. In some embodiments the treatment probe comprises a diffractive optic, an axicon or lenses, as is known to one of ordinary skill in the art, configured to delivery energy to the plurality of treatment locations. Alternatively, or in combination, the light outputs may transmit light towards the eye from a light source external to the handheld probe, for example from a light source via a fiber bundle as shown in FIG. 5B and/or from a laser light source via a coupler and a manifold assembly as shown in FIG. 5C. In some instances, the light outputs may be controlled as one with a processor as described herein. In some instances, the light outputs may be individually and independently controlled, for example to adjust the treatment pattern delivered to a patient's eye. The light outputs may provide continuous or pulsed light energy to the treatment location. The light outputs may be configured to deliver light energy at the same wavelength. Alternatively, the light outputs may be configured to deliver different wavelengths of light energy. For example, the outer annulus shown in FIG. 5A may comprise light at a wavelength of 1.48 μm while the inner annulus may comprise light at a wavelength of 2.01 μm, or vice versa.

Although reference is made to a probe comprising a handpiece configured for treatment radially inward of the lens equator, the probe can be configured in many ways to treat the eye, for example to treat regions of the sclera of the eye radially outward from Schlemm's canal and the limbus and may be configured to avoid the cornea and limbus in some embodiments. In other words, all the light outputs may be positioned on the distal face of the probe at a sufficient distance from the center of the distal face to avoid contact with the cornea and/or limbus when the distal probe face is applied to the eye during treatment. The light outputs may also be positioned to avoid the insertions of intraocular muscles on the eye.

The handheld probe may be configured to be directly coupled with the patient eye. Alternatively, or in combination, the handheld probe may be configured to be coupled to a patient interface or patient coupling structure as described herein (as discussed in connection with FIGS. 9B, 9C and 9D). The distal face 254 of probe 250 may for example be configured to dock with a patient interface or to directly contact the eye to be treated. It will be understood by one of ordinary skill in the art that the light outputs may be replaced by any source of treatment energy as described herein. For example, the light outputs may be replaced by radiofrequency electrodes or the like.

A system to treat glaucoma of an eye with the hand-held energy probe may comprise an energy source, such as one or more of the laser light sources as described herein. The handpiece comprising the treatment probe is coupled to the energy source. The handpiece comprises an eye contacting surface to couple to the eye on the distal end of the probe, and a plurality of energy releasing elements disposed at a plurality of locations to release energy to the eye at a plurality of treatment locations radially inward of the lens equator. The distal face of the probe on which the light outputs are arranged can be a variety of shapes and sizes. The distal end may comprise a concave shape such as a spherical shape or a conical shape to engage the eye. The distal face may, for example, but flat or curved; if curved it may be of a curvature to substantially conform to the curvature of the front of the eye to which the distal face is to be applied. In particular embodiments, the diameter of the distal face of the probe is 19 mm in diameter and the face may be a contact lens that acts as a heart sink to conduct heat away from the surface of the eye. In some embodiments the laser patterns are arranged in concentric first and second annuli, with the first annulus 14 mm diameter from the center of the distal probe face, and the second annulus 15 mm from the center of the distal probe face. In other embodiments the distal face has a radius of curvature or radii of curvatures of between 8-12 mm to substantially conform to the shape of the cornea and sclera. In other embodiments the central curvature of the face can be 6-8 mm with a longer radius of curvature (or no curvature at all). Some embodiments can have central holes for added functionality, for example holes having a diameter of 0.5 mm to 1 mm or 0.5 mm to 1.5 mm or 2 mm. These lenses can be coated with heat conducting materials such as Single Layer Graphene and can be assembled with microcircuits for specialized functions such as conductivity and pressure measurements. Suitable lenses are more fully disclosed in US2018/0177632 that is incorporated by reference to the extent it is not inconsistent with the present specification.

The handpiece therefore includes an eye contacting surface to couple directly or indirectly to the eye and a plurality of energy releasing elements disposed at a plurality of locations on the probe to release energy to the eye at the predetermined plurality of treatment locations. The plurality of predetermined treatment locations may be as described herein, for example located at least about 2 mm radially outward from a limbus and corresponding to an angle within a range from about 30 degrees to about 360 degrees around a sclera of the eye. The handpiece may be configured to deliver the energy to the plurality of treatment locations to open an angle of the eye by an amount within a range from about 0.5 degrees to about 10 degrees. The energy releasing elements may comprise electrodes or light outputs such as ends of optical fibers. The plurality of locations may correspond to treatment locations located radially inward from the equator of the eye toward an optical axis of the eye and radially outward from the limbus away from the optical axis of the eye or the center of the cornea as measured along an exterior surface of the eye. The plurality of treatment locations may generally correspond to a diameter more than about 2 mm from the limbus. The plurality of energy releasing elements may comprise a plurality of optical fibers and the energy source may comprise a laser.

Alternatively, or in combination, the plurality of energy releasing elements may comprise a plurality of electrodes and the energy source may comprise an electroporation energy source, a microwave energy source, a thermal energy source, an electrical energy source, an electrophoretic energy source, or a di-electrophoretic energy source.

Experimental Results for Angle-Opening Method

Initial experimental data was obtained in pig eyes, which are 10-20% larger than human eyes. The average limbal diameter in humans is generally considered to be about 10-12 mm (*Clin. Exp. Optom.* 2017; 100: 522-528). The average pig eye limbus has a diameter of 13.5 mm, which is about 1.5 mm larger than in a human.

FIGS. 6A-6B and 7A-7B show OCT images of eyes from experiments done in ex vivo porcine eyes showing that the systems and methods described herein may be used to open the iridocorneal angle to treat narrow angle glaucoma by increasing the iridocorneal angle. OCT images were taken prior to treatment ("pre-op") and after treatment ("post-op") and the laser-induced angle-opening was measured using full-scale extended Trabecular Iris Space Area measurements ("TISA-750"). FIGS. 6A, 6B, 7A and 7B show pre-treatment and post-treatment images from experiments done using a system comprising a 1.43 µm laser. FIGS. 8A-8B show pre-treatment and post-treatment results from experiments done using a system comprising a 2.01 µm laser.

Figure 6B:
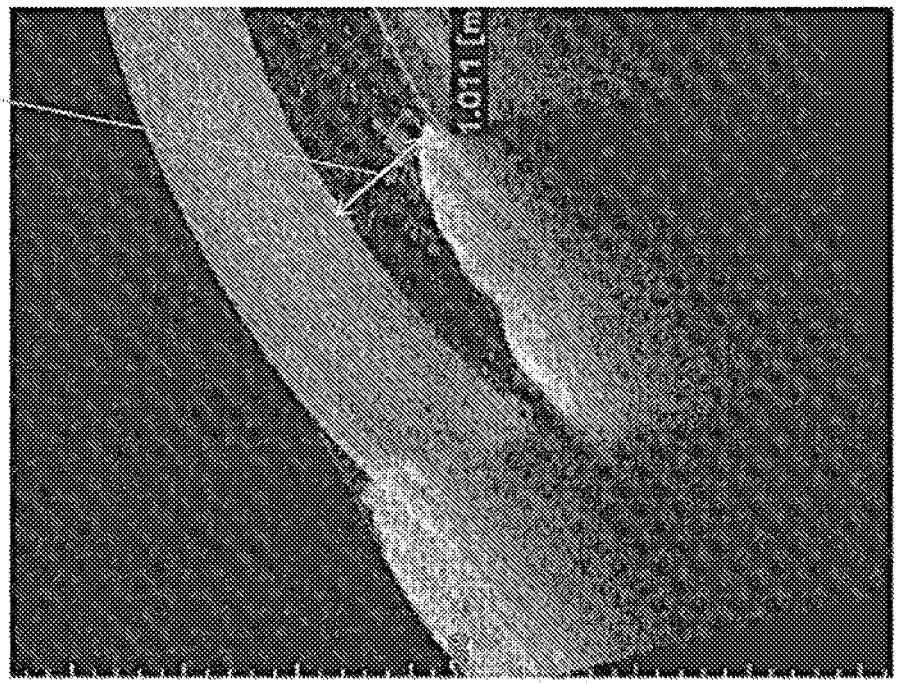
FIGS. 6A and 6B show pre-operative and post-operative images respectively of the inferior angle of a porcine eye treated ex vivo, in accordance with the angle-opening method disclosed herein.
Figure 6A:
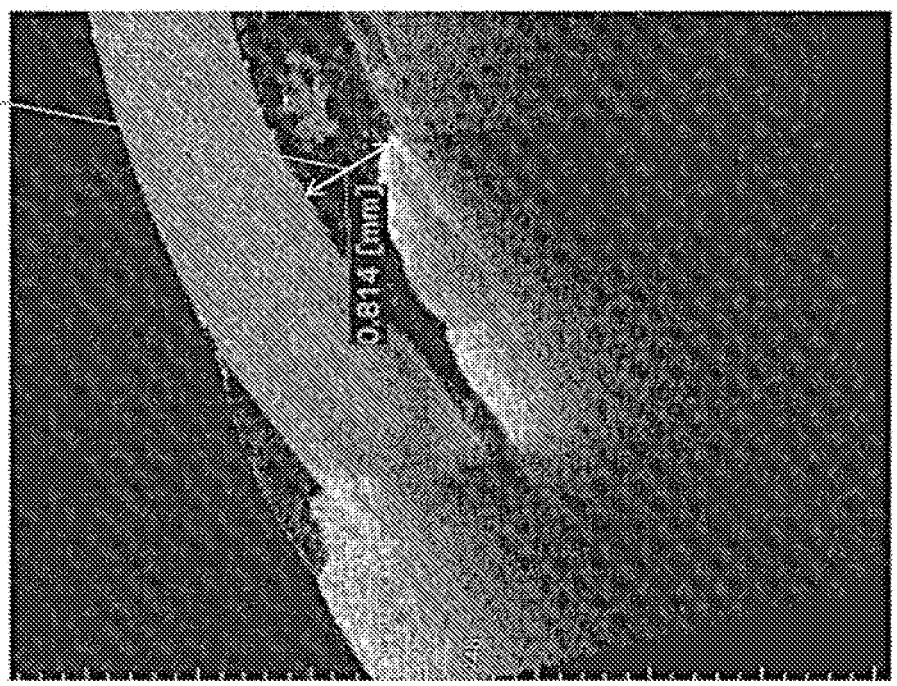

FIGS. 6A and 6B show pre-operative and post-operative images of the inferior angle of a porcine eye treated ex vivo with the system described herein. Treatment was patterned for 360 degrees in an annulus 2 mm radially outward from the limbus. The annulus was shaped to correspond to or mimic the shape of the limbus using the methods described herein. The continuous wave laser was operated with a power of 300 mw, a beam size of 0.6 mm, and a scan speed of 10 mm/s. 12 repetitions were performed. Prior to treatment, the TISA distance ("TISApre") was measured to be 0.814 mm After treatment, the TISA distance ("TISApost") was measured to be 1.011 mm. The change in TISA distance (pre-op to post-op) was 0.197 mm, or about 24%.

Figure 7B:
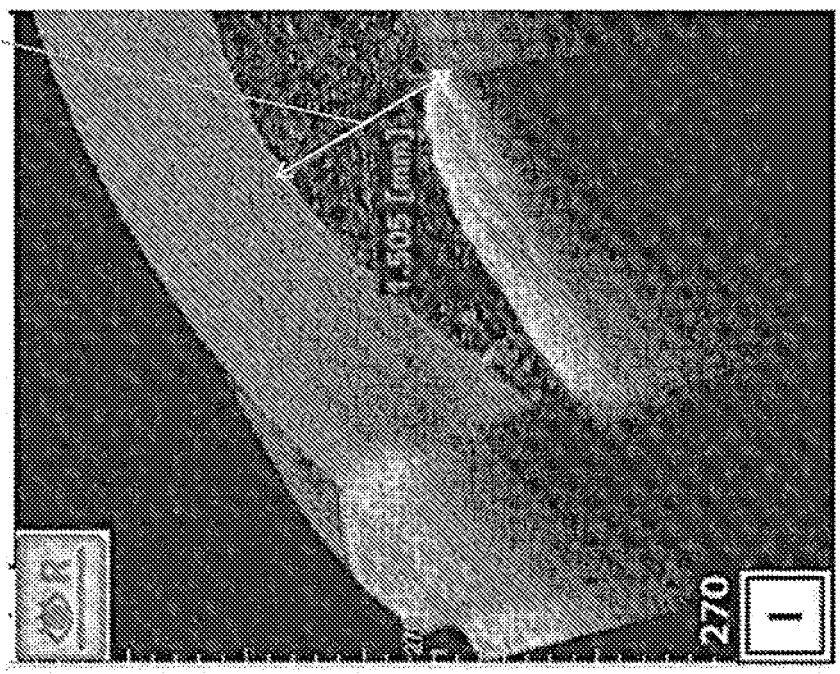
FIGS. 7A and 7B show pre-operative and post-operative images respectively of the inferior angle of a porcine eye treated ex vivo, in accordance with the angle-opening method disclosed herein.
Figure 7A:
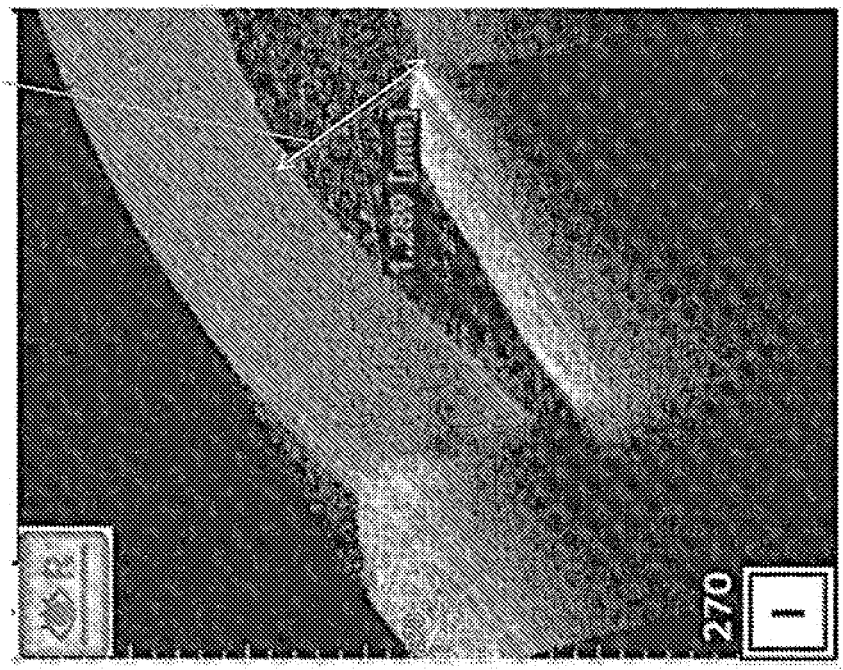
Figure 8A:
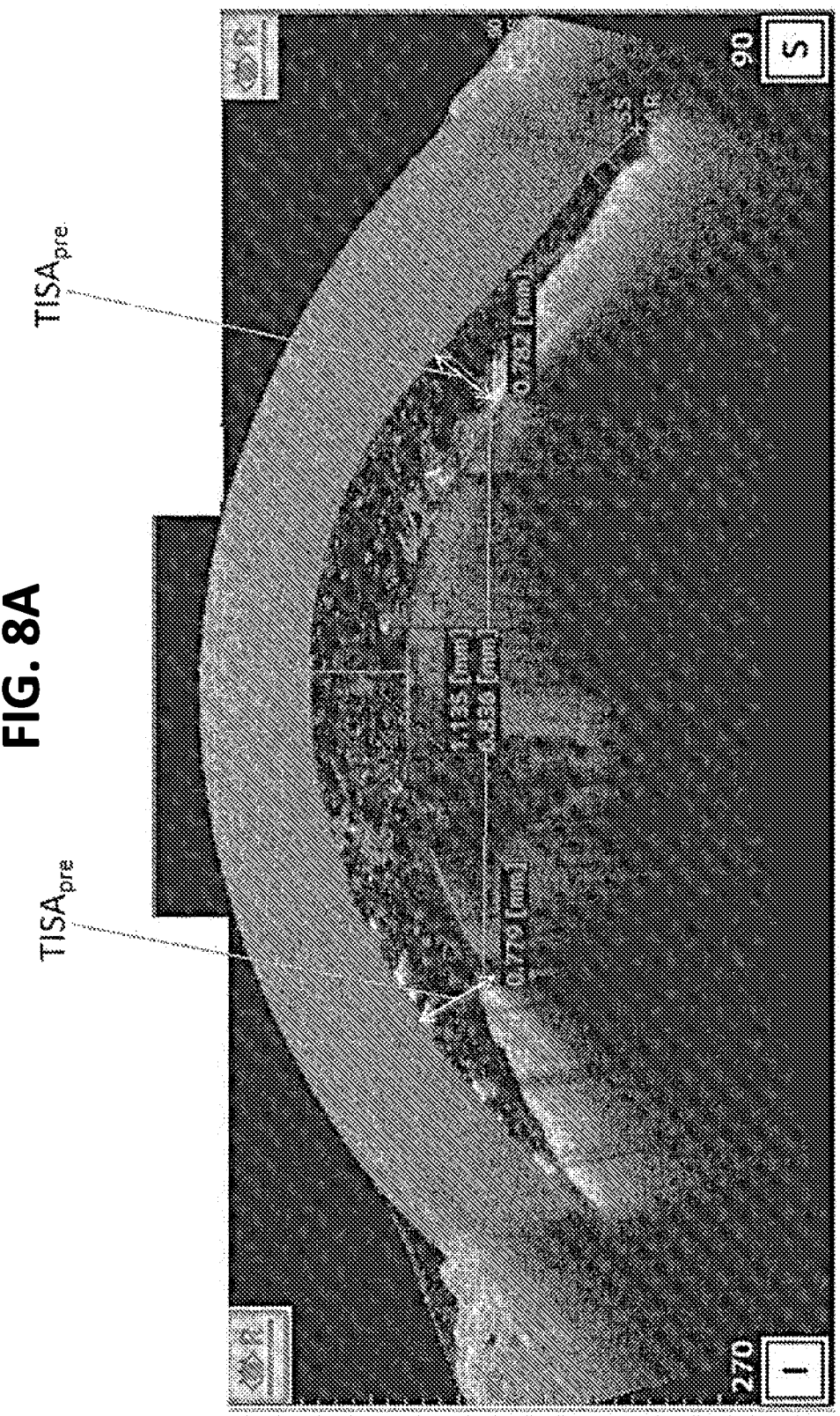
FIGS. 8A and 8B show pre-operative and post-operative images respectively of the superior-inferior line of a porcine eye treated ex vivo, in accordance with the angle-opening method.
Figure 8B:
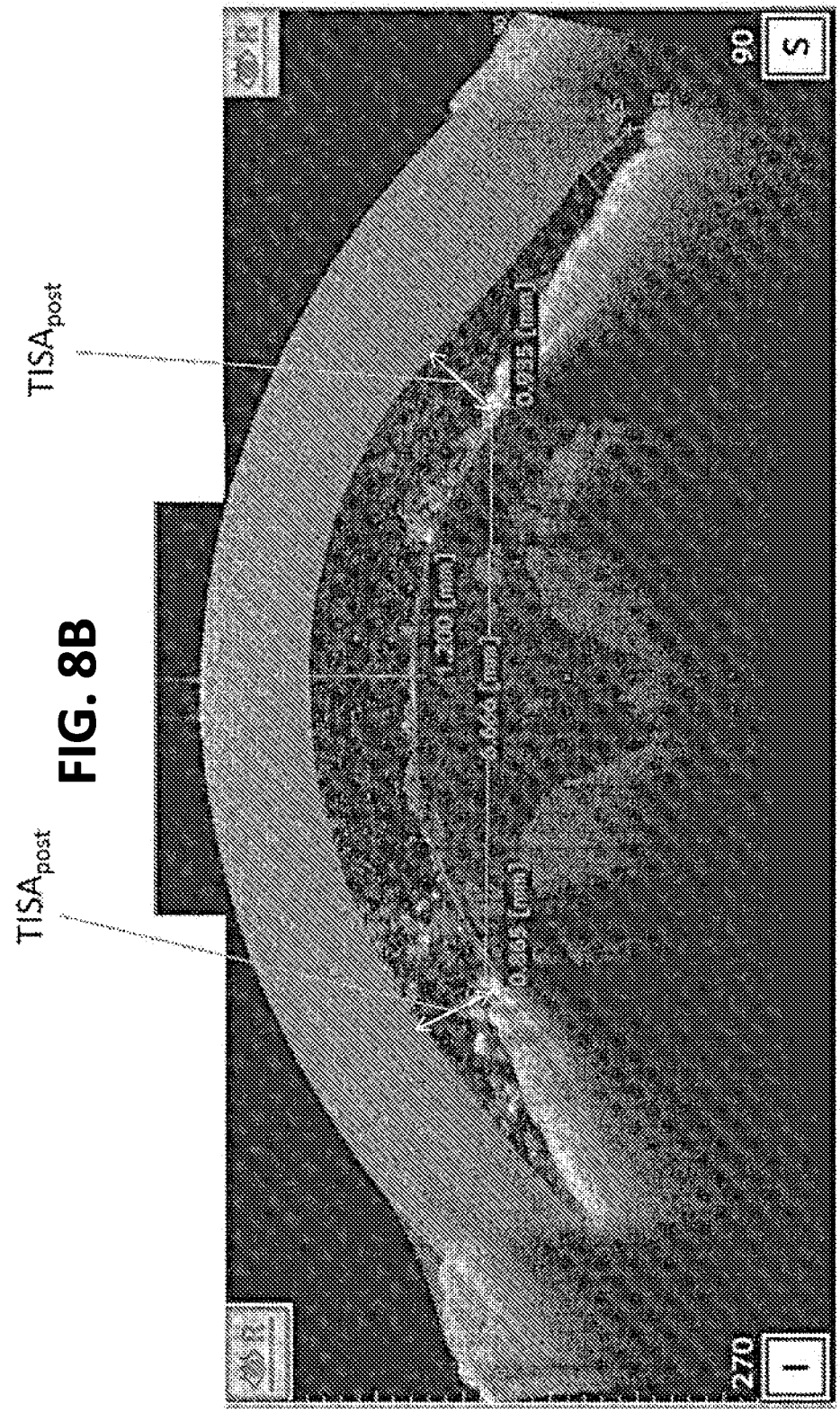

FIGS. 7A and 7B show pre-operative and post-operative images of the inferior angle of a porcine eye treated ex vivo with the system described herein. Treatment was patterned for 360 degrees in annuli located approximately 16 mm, 17 mm, and 17.5 mm radially outward from the center of the eye, which corresponds to about 2.5 mm to 4 mm radially outward from the limbus of the pig, or about 2.0 to about 3.5 mm outward from the limbus in a human. The continuous wave laser was operated with a power of 800 mw, a beam size of 0.6 mm, and a scan speed of 2.5 mm/s. Two repetitions were performed. Prior to treatment, the TISA distance ("TISApre") was measured to be 1.289 mm After treatment, the TISA distance ("TISApost") was measured to be 1.505 mm. The change in TISA distance (pre-op to post-op) was 0.216 mm, or about 16%.

FIGS. 8A and 8B show pre-operative and post-operative images of the superior-inferior line of a porcine eye treated ex vivo with the system described herein. Treatment was patterned for 360 degrees in annuli located approximately 2.5 and 3.0 mm outwardly from the limbus. The continuous wave laser was operated with a power of 400 mw, a beam size of 0.6 mm, and a scan speed of 5 mm/s. Five repetitions were performed. Prior to treatment, the inferior TISA distance ("TISApre") was measured to be 0.779 mm After treatment, the inferior TISA distance ("TISApost") was measured to be 0.865 mm. The change in inferior TISA distance (pre-op to post-op) was 0.086 mm, or about 11%. Prior to treatment, the superior TISA distance ("TISApre") was measured to be 0.782 mm After treatment, the superior TISA distance ("TISApost") was measured to be 0.935 mm. The change in superior TISA distance (pre-op to post-op) was 0.153 mm, or about 20%.

Tables 1-2 show the results of similar proof-of-concept experiments (Experiments 1-15) with varying treatment parameters. Table 1 shows the treatment parameters used for each experimental group. Table 2 shows the average change in TISA measurement (post-op vs. pre-op) for the inferior angle and the superior angle as well as the average change in anterior chamber depth ("ACD") for each treatment group. OCT images were taken pre- and post-op (not shown) along an superior-inferior line spanning roughly from 90° to 270° using conventional reference angles used by a physician. TISA was performed to determine the iridocorneal angle for both the inferior angle (located at about 270°) and the superior angle (located at about 90°). Table 3 shows the average change in angle calculated from the ACD measurements. Assuming that the volume of the lens is unchanged by treatment, in order to translocate the ACD (i.e. to translocate the apex of the lens), the equator of the lens may translate an estimated twice as much, based on curvature differences and assuming capsular elasticity to be uniform. The law of cosines may be used to calculate the iridocorneal angle based on the change in ACD. For example, a typical pig eye with an angle of 8 mm×6 mm×5.5 mm may change by 150 ums in ACD and equates to 300 µm triangular shift or about 3 degrees at the iridocorneal angle.

TABLE 1

Experimental Parameters

| Exp No. | n | Wavelength (um) | Beam size (mm) | Power (mW) | Scan Speed (mm/s) | No. Reps | 1st Annulus (mm) | 2nd Annulus (mm) | 3rd Annulus (mm) |
|---|---|---|---|---|---|---|---|---|---|
| 1 | 11 | 2.01 | 0.6 | 400 | 10 | 10 | 2.5 | 3.0 | 3.5 |
| 2 | 12 | 2.01 | 0.6 | 400 | 5 | 5 | 2.5 | 3.5 | |

TABLE 1-continued

Experimental Parameters

| Exp No. | n | Wavelength (um) | Beam size (mm) | Power (mW) | Scan Speed (mm/s) | No. Reps | 1st Annulus (mm) | 2nd Annulus (mm) | 3rd Annulus (mm) |
|---|---|---|---|---|---|---|---|---|---|
| 3 | 1 | 2.01 | 0.6 | 400 | 5 | 10 | 3.5 | 4 | |
| 4 | 3 | 2.01 | 0.6 | 400 | 5 | 10 | 3.5 | 4 | |
| 5 | 10 | 2.01 | 0.6 | 400 | 5 | 4 | 3.0 | 3.5 | 4.0 |
| 6 | 10 | SHAM | SHAM | SHAM | SHAM | SHAM | SHAM | SHAM | SHAM |
| 7 | 10 | 2.01 | 0.6 | 400 | 5 | 4 | 3.0 | 3.5 | 4.0 |
| 8 | 10 | 1.48 | 0.6 | 800 | 5 | 4 | 4.0 | 3.5 | 3.0 |
| 9 | 6 | 1.48 | 0.6 | 800 | 2.5 | 1 | 4.0 | 3.5 | |
| 10 | 7 | 1.48 | 0.6 | 800 | 2.5 | 2 | 4.0 | 3.5 | 3.0 |
| 11 | 7 | 1.48 | 0.6 | 800 | 2.5 | 2 | 4.0 (90°) | 3.5 (90°) | 3 (90°) |
| 12 | 5 | 1.48 | 0.6 | 800 | 10 | 40 | 4.0 (90°) | 3.5 (90°) | 3 (90°) |
| 13 | 9 | 1.48 | 0.6 | 800 | 2.5 | 4 | 4.0 (90°) | 3.5 (90°) | 3 (90°) |
| 14 | 6 | 1.48 | 0.6 | 800 | 10 | 40 | 4.0 | 3.5 | 3 |
| 15 | 13 | 1.48 | 0.6 | 800 | 2.5 | 4 | 4.0 | 3.5 | 3.0 |

TABLE 2

Experimental Results

| Exp No. | Avg Δinf (mm) | SD ΔInf | p value Δinf | Avg Δsup (mm) | SD ΔSup | p value ΔSup | Avg ΔACD (mm) | SD ΔACD | p value ΔACD |
|---|---|---|---|---|---|---|---|---|---|
| 1 | 0.06 | 0.06 | 0.0051 | 0.1 | 0.06 | 0.0002 | 0.06 | 0.03 | 0.0001 |
| 2 | 0.08 | 0.04 | 0.0001 | 0.08 | 0.05 | 0.0002 | 0.08 | 0.04 | 0 |
| 3 | 0.03 | N/A | N/A | 0.1 | N/A | N/A | 0.07 | N/A | N/A |
| 4 | 0.1 | 0.1 | 0.24 | 0.1 | 0.04 | 0.053 | 0.07 | 0.05 | 0.136 |
| 5 | 0.08 | 0.06 | 0.0018 | 0.08 | 0.04 | 0.0002 | 0.05 | 0.05 | 0.005 |
| 6 | 0 | 0.03 | 0.8704 | 0.01 | 0.02 | 0.1048 | <0.0001 | 0.02 | 0.811 |
| 7 | 0.04 | 0.04 | 0.08 | 0.07 | 0.09 | 0.094 | 0.08 | 0.06 | 0.0298 |
| 8 | 0.11 | 0.08 | 0.001 | 0.11 | 0.09 | 0.002 | 0.11 | 0.05 | 0.0002 |
| 9 | 0.1 | 0.09 | 0.037 | 0.1 | 0.06 | 0.01 | 0.11 | 0.05 | 0.0036 |
| 10 | 0.19 | 0.09 | 0.002 | 0.14 | 0.06 | 0.001 | 0.18 | 0.05 | 0.0001 |
| 11 | 0.1 | 0.04 | 0.0004 | 0.02 | 0.02 | 0.064 | 0.13 | 0.06 | 0.0014 |
| 12 | 0.13 | 0.11 | 0.048 | 0.03 | 0.04 | 0.228 | 0.15 | 0.04 | 0.0012 |
| 13 | 0.18 | 0.31 | 0.0113 | 0.04 | 0.09 | 0.184 | 0.08 | 0.08 | 0.0134 |
| 14 | | | | | | | 0.09 | 0.03 | 0.0005 |
| 15 | | | | | | | 0.16 | 0.06 | 0.0001 |

TABLE 3

Calculated Change in Angle

| Exp No. | Avg Δangle (°) | SD Δangle | p value Δangle |
|---|---|---|---|
| 1 | 2.55 | 0.63 | 0.0001 |
| 2 | 2.81 | 0.71 | <0.0001 |
| 3 | 3.67 | N/A | N/A |
| 4 | 3.75 | 0.58 | 0.008 |
| 5 | 3.54 | 0.51 | 0.0001 |
| 6 | 1.36 | 0.33 | <0.0001 |
| 7 | 2.9 | 1.27 | 0.0026 |
| 8 | 3.42 | 1.08 | <0.0001 |
| 9 | 3.51 | 1.04 | 0.0004 |
| 10 | 4.85 | 0.99 | <0.0001 |
| 11 | 3.83 | 1.17 | 0.02 |
| 12 | 4.27 | 0.8 | 0.0003 |
| 13 | 2.77 | 1.69 | 0.0004 |
| 14 | 3.05 | 0.53 | 0.0001 |
| 15 | 4.55 | 1.22 | 0.0001 |

The examples of the method were performed at powers of 400-800 mW, scanning speeds of 2.5-10 mm/s, with repetitions ranging from 1-40. The treatment method may be performed using other parameters, such as a power of 200-2000 mW, scanning speeds of 1-20 mm/s, and repetitions ranging from 1-100.

Porcine eyes were collected for ex vivo use and stored for 2-3 days before treatment. Extended storage time may lead to exaggerated angle closure after collection (see for example Table 4). The eyes were then soaked in tap water at room temperatures for at least 15 minutes before being loaded into the patient interface described herein. Thealoz Duo 3× drops were then added onto the cornea. Prior to treatment, an OCT scan was taken to assess the position of the eye. The position of the eye within the fixture was adjustable for tip/tilt minimization using the OCT scan as a guide. The treatment protocol was set up using the processor and GUI as described herein.

Experiments 1-10 and 14-15 were treated with 360° annuli radially inward (i.e. anterior) of the lens equator. Annuli were spaced at 16 mm, 16.5 mm, 17 mm, and/or 17.5 mm radially outwards from the center of the eye. It is noted that these values were chosen for porcine eyes, which are generally about 10-20% larger dimensionally that human eyes, although most pig eyes fall within that range and not at its endpoints. One of ordinary skill in the art will understand how to adjust the parameters and treatment locations described herein to account for the difference in size between a pig eye and a human eye, and the relationship to the limbus in a pig or human. For example, 16 mm, 16.5 mm and 17 mm from the center of the pig eye correspond respectively to about 2.5 mm, 3 mm and 3.5 mm radially outward from the pig limbus, which generally corresponds on average to slightly more than 2 mm, 2.5 mm and 3.0 mm respectively radially outward from the human limbus. The $1^{st}$ annulus was applied first, the $2^{nd}$ annulus next, and the $3^{rd}$ annulus (if any) was applied third.

Thermal laser and patterning requirements for angle-opening can be significantly different than for opening of Schlemm's canal or the trabecular meshwork. For example, angle-opening treatment may be patterned to avoid ciliary body, choroidal coagulation, and preferably treat in the outer posterior sclera, sparing the conjunctiva. If coagulative shrinkage can be constrained at scleral depth from 50 μm to 400 um, the inventors estimate that most patients will be protected. Use of a 2.01 μm (or 1.93 um) laser is selected provide such a range. A 2.01 laser can provide a better margin than the 1.48 μm laser, although the latter may provide the necessary depth of penetration for canalicular-proximal shrinkages. On the theory that the presumed mechanism for angle-opening is Anterior Zonular tightening at its scleral insertion, circumferentially resulting in pupillary ACD perpendicular distance increase along with angle as described herein, there is believed to be less of a requirement to deposit a precise custom treatment pattern near the limbus. In fact, the limbus may be avoided by a margin of at least about 1 mm, preferably about 2 mm in order to minimize refractive changes, when opening of Schlemm's canal is not the goal of the applied treatment pattern.

Experiment 1:

Eleven eyes were treated. Treatment was patterned for 360 degrees in annuli located approximately 2.5 mm, 3 mm, and 3.5 mm radially outward from the limbus. The 2.01 μm continuous wave laser was operated with a power of 400 mw, a beam size of 0.6 mm, and a scan speed of 10 mm/s. Ten repetitions were performed. The average change in inferior TISA distance (pre-op to post-op) was 0.06±0.06 mm, with a p-value of p=0.0051. The average change in superior TISA distance (pre-op to post-op) was 0.1±0.06 mm, with a p-value of p=0.0002. The average change in ACD (pre-op to post-op) was 0.06±0.03 mm, with a p-value of p=0.0001. Together these changes resulted in an average change in angle of 2.55±0.63°, with a p-value of p=0.0001.

Experiment 2:

Twelve eyes were treated. Treatment was patterned for 360 degrees in annuli located approximately 2.5 mm and 3.5 mm radially outward from the limbus. The 2.01 μm continuous wave laser was operated with a power of 400 mw, a beam size of 0.6 mm, and a scan speed of 5 mm/s. Five repetitions were performed. The average change in inferior TISA distance (pre-op to post-op) was 0.08±0.04 mm, with a p-value of p=0.0001. The average change in superior TISA distance (pre-op to post-op) was 0.08±0.05 mm, with a p-value of p=0.0002. The average change in ACD (pre-op to post-op) was 0.08±0.04 mm, with a p-value of p<0.0001. Together these changes resulted in an average change in angle of 2.81±0.71°, with a p-value of p<0.0001.

Experiment 3:

One eye was treated. Treatment was patterned for 360 degrees in annuli located approximately 3.4 mm and 4.0 mm radially outward from the limbus. The 2.01 μm continuous wave laser was operated with a power of 400 mw, a beam size of 0.6 mm, and a scan speed of 5 mm/s. Ten repetitions were performed. The change in inferior TISA distance (pre-op to post-op) was 0.03 mm. The change in superior TISA distance (pre-op to post-op) was 0.01 mm. The change in ACD (pre-op to post-op) was 0.07 mm. Together these changes resulted in a change in angle of 3.67°.

Experiment 4:

Three eyes were treated. Treatment was patterned for 360 degrees in annuli located approximately 3.5 mm and 4.0 mm radially outward from the limbus. The 2.01 μm continuous wave laser was operated with a power of 400 mw, a beam size of 0.6 mm, and a scan speed of 5 mm/s. Ten repetitions were performed. The average change in inferior TISA distance (pre-op to post-op) was 0.1±0.1 mm, with a p-value of p=0.24. The average change in superior TISA distance (pre-op to post-op) was 0.1±0.04 mm, with a p-value of p=0.053. The average change in ACD (pre-op to post-op) was 0.07±0.05 mm, with a p-value of p=0.136. Together these changes resulted in an average change in angle of 3.75±0.58°, with a p-value of p=0.008.

Experiment 5:

Ten eyes were treated. Treatment was patterned for 360 degrees in annuli located approximately 3 mm, 3.5 mm, and 4.0 mm radially outward from the limbus. The 2.01 μm continuous wave laser was operated with a power of 400 mw, a beam size of 0.6 mm, and a scan speed of 5 mm/s. Four repetitions were performed. The average change in inferior TISA distance (pre-op to post-op) was 0.08±0.06 mm, with a p-value of p=0.0018. The average change in superior TISA distance (pre-op to post-op) was 0.08±0.04 mm, with a p-value of p=0.0002. The average change in ACD (pre-op to post-op) was 0.05±0.05 mm, with a p-value of p=0.005. Together these changes resulted in an average change in angle of 3.54±0.51°, with a p-value of p=0.0001.

Experiment 6:

Ten eyes were treated with a SHAM treatment (i.e. without laser deposition) as a negative control. The average change in inferior TISA distance (pre-op to post-op) was 0±0.03 mm, with a p-value of p=0.8704. The average change in superior TISA distance (pre-op to post-op) was 0.01±0.02 mm, with a p-value of p=0.1048. The average change in ACD (pre-op to post-op) was 0±0.02 mm, with a p-value of p=0.811. Together these changes resulted in an average change in angle of 1.36±0.33°, with a p-value of p<0.0001.

Experiment 7:

Six eyes were treated. Treatment was patterned for 360 degrees in annuli located approximately 3 mm, 3.5 mm, and 4.0 mm radially outward from the limbus. The 2.01 μm continuous wave laser was operated with a power of 400 mw, a beam size of 0.6 mm, and a scan speed of 5 mm/s. Four repetitions were performed. The average change in inferior TISA distance (pre-op to post-op) was 0.04±0.04 mm, with a p-value of p=0.08. The average change in superior TISA distance (pre-op to post-op) was 0.07±0.09 mm, with a p-value of p=0.094. The average change in ACD (pre-op to post-op) was 0.08±0.06 mm, with a p-value of p=0.0298. Together these changes resulted in an average change in angle of 2.9±1.27°, with a p-value of p=0.0026.

Experiment 8:

Ten eyes were treated. Treatment was patterned for 360 degrees in annuli located approximately 4 mm, 3.5 mm, and 3.0 mm radially outward from the limbus. The 1.48 μm continuous wave laser was operated with a power of 800 mw, a beam size of 0.6 mm, and a scan speed of 5 mm/s. Four repetitions were performed. The average change in inferior TISA distance (pre-op to post-op) was 0.11±0.08 mm, with a p-value of p=0.001. The average change in superior TISA distance (pre-op to post-op) was 0.11±0.09 mm, with a p-value of p=0.002. The average change in ACD (pre-op to post-op) was 0.11±0.05 mm, with a p-value of p=0.0002. Together these changes resulted in an average change in angle of 3.42±1.08°, with a p-value of p<0.0001.

Experiment 9:

Six eyes were treated. Treatment was patterned for 360 degrees in annuli located approximately 4.0 mm, and then 3.5 mm radially outward from the limbus. The 1.48 μm continuous wave laser was operated with a power of 800 mw, a beam size of 0.6 mm, and a scan speed of 2.5 mm/s. One repetition was performed. The average change in inferior TISA distance (pre-op to post-op) was 0.1±0.09 mm, with a p-value of p=0.037. The average change in superior TISA distance (pre-op to post-op) was 0.1±0.06 mm, with a p-value of p=0.01. The average change in ACD (pre-op to post-op) was 0.11±0.05 mm, with a p-value of p=0.0036. Together these changes resulted in an average change in angle of 3.51±1.04°, with a p-value of p=0.0004.

Experiment 10:

Seven eyes were treated. Treatment was patterned for 360 degrees in annuli located approximately 4.0 mm, 3.5 mm, and 3.0 mm radially outward from the limbus. The 1.48 μm continuous wave laser was operated with a power of 800 mw, a beam size of 0.6 mm, and a scan speed of 2.5 mm/s. Two repetitions were performed. The average change in inferior TISA distance (pre-op to post-op) was 0.19±0.09 mm, with a p-value of p=0.002. The average change in superior TISA distance (pre-op to post-op) was 0.14±0.06 mm, with a p-value of p=0.001. The average change in ACD (pre-op to post-op) was 0.18±0.05 mm, with a p-value of p=0.0001. Together these changes resulted in an average change in angle of 4.85±0.99°, with a p-value of p<0.0001.

Experiment 14:

Six eyes were treated. Treatment was patterned for 360 degrees in annuli located approximately 4.0 mm, 3.5 mm, and 3.0 mm radially outward from the limbus. The 1.48 μm continuous wave laser was operated with a power of 800 mw, a beam size of 0.6 mm, and a scan speed of 10 mm/s. Forty repetitions were performed. The average change in ACD (pre-op to post-op) was 0.09±0.03 mm, with a p-value of p=0.0005. Together these changes resulted in an average change in angle of 3.05±0.53°, with a p-value of p=0.0001. TISA distances were not measured.

Experiment 15:

Thirteen eyes were treated. Treatment was patterned for 360 degrees in annuli located approximately 4.0 mm, 3.5 mm, and 3.0 mm radially outward from the limbus. The 1.48 μm continuous wave laser was operated with a power of 800 mw, a beam size of 0.6 mm, and a scan speed of 2.5 mm/s. Four repetitions were performed. The average change in ACD (pre-op to post-op) was 0.16±0.06 mm, with a p-value of p=0.0001. Together these changes resulted in an average change in angle of 4.55±1.22°, with a p-value of p=0.0001. TISA distances were not measured.

Experiments 11-13 were treated with 90° arcs about the superior-inferior line on the inferior side of the eye radially inward (i.e. anterior) of the lens equator as shown in FIG. 3D. The arcs were spaced at 3.0 mm, 3.5 mm, and 4.0 mm radially outward from the limbus. It is noted that these values were chosen for porcine eyes, which are generally larger dimensionally that human eyes. One of ordinary skill in the art will understand how to adjust the parameters and treatment locations described herein to account for the difference in size between a pig eye and a human eye.

Experiment 11:

Seven eyes were treated. Treatment was patterned for 90 degrees in arcs located approximately 3.0 mm, 3.5 mm, and 4.0 mm radially outward from the limbus. The 1.48 μm continuous wave laser was operated with a power of 800 mw, a beam size of 0.6 mm, and a scan speed of 2.5 mm/s. Two repetitions were performed. The average change in inferior TISA distance (pre-op to post-op) was 0.1±0.04 mm, with a p-value of p=0.0004. The average change in superior TISA distance (pre-op to post-op) was 0.02±0.02 mm, with a p-value of p=0.064. The average change in ACD (pre-op to post-op) was 0.13±0.06 mm, with a p-value of p=0.0014. Together these changes resulted in an average change in inferior angle of 3.83±1.17°, with a p-value of p=0.02.

Experiment 12:

Five eyes were treated. Treatment was patterned for 90 degrees in arcs located approximately 3.0 mm, 3.5 mm, and 4.0 mm radially outward from the limbus. The 1.48 μm continuous wave laser was operated with a power of 800 mw, a beam size of 0.6 mm, and a scan speed of 10 mm/s. Forty repetitions were performed. The average change in inferior TISA distance (pre-op to post-op) was 0.13±0.11 mm, with a p-value of p=0.048. The average change in superior TISA distance (pre-op to post-op) was 0.03±0.04 mm, with a p-value of p=0.228. The average change in ACD (pre-op to post-op) was 0.15±0.04 mm, with a p-value of p=0.0012. Together these changes resulted in an average change in inferior angle of 4.27±0.8°, with a p-value of p=0.0003.

Experiment 13:

Nine eyes were treated. Treatment was patterned for 90 degrees in arcs located approximately 3.0 mm, 3.5 mm, and 4.0 mm radially outward from the limbus. The 1.48 μm continuous wave laser was operated with a power of 800 mw, a beam size of 0.6 mm, and a scan speed of 2.5 mm/s. Four repetitions were performed. The average change in inferior TISA distance (pre-op to post-op) was 0.18±0.31 mm, with a p-value of p=0.0113. The average change in superior TISA distance (pre-op to post-op) was 0.04±0.09 mm, with a p-value of p=0.184. The average change in ACD (pre-op to post-op) was 0.08±0.08 mm, with a p-value of p=0.0134. Together these changes resulted in an average change in inferior angle of 2.77±1.69°, with a p-value of p=0.0004.

Table 4 shows how storage time of ex vivo porcine eyes can affect the ACD. After a day of storage, the average ACD was 2.2±0.31 mm After two days, the average ACD had decreased to 1.32±0.18 mm After three days, the average ACD had further decreased to 0.91±0.32 mm. The average ACD was significantly larger on day 1 than on day 3 (p=0.003). The average ACD was significantly smaller on day 2 than on day 1 (p=0.003). The average ACD was significantly smaller on day 3 than on day 1 (p=0.003).

TABLE 4

Change in ACD with increasing storage time.

| n | Storage Time (days) | Avg ACD (mm) | SD ACD | p value ACD |
|---|---|---|---|---|
| 6 | 1 | 2.2 | 0.31 | 0.003 |
| 8 | 2 | 1.32 | 0.18 | 0.003 |
| 8 | 3 | 0.91 | 0.32 | 0.003 |

Tables 5-6 show the results of Experiment 16 testing how the ACD changes as sequential treatment annuli are applied to the eye with varying treatment parameters. Table 5 shows the treatment parameters used for each experimental group. Table 6 shows the average change in ACD for each treatment group after the first treatment annulus and after the addition of the second treatment annulus. OCT images were taken pre- and post-op (not shown) along a superior-inferior line spanning roughly from 90° to 270° using conventional reference angles used by a physician and the change in ACD was measured as described herein. Porcine eyes were collected for ex vivo use and stored for 2-3 days before treatment.

TABLE 5

Experimental Parameters

| Exp No. | n | Wavelength (um) | Beam size (mm) | Power (mW) | Scan Speed (mm/s) | No. Reps | 1st Annulus (mm) | 2nd Annulus (mm) | 3rd Annulus (mm) |
|---|---|---|---|---|---|---|---|---|---|
| 16 | 9 | 1.48 | 0.6 | 800 | 2.5 | 4 | 4 | 3.5 | |

TABLE 6

Experimental Results

| Exp No. | Avg ΔACD (mm) after $1^{st}$ annulus | SD ΔACD (mm) after $2^{st}$ annulus | p value ΔACD ($1^{st}$ annulus vs. $2^{nd}$ annulus) | Avg ΔACD (mm) after $2^{st}$ annulus | SD ΔACD (mm) after $2^{nd}$ annulus | p value ΔACD($1^{st}$ annulus vs. $2^{nd}$ annulus) |
|---|---|---|---|---|---|---|
| 16 | 0.11 | 0.04 | 0.0001 | 0.04 | 0.04 | 0.003 |

Experiment 16:

Nine eyes were treated. Treatment was patterned for 360 degrees in annuli located approximately 3.5 mm and 4 mm radially outward from the limbus. The 1.48 μm continuous wave laser was operated with a power of 800 mw, a beam size of 0.6 mm, and a scan speed of 2.5 mm/s. Four repetitions were performed. The first annulus treated was at 17.5 mm and the second annulus treated was at 17 mm. The average change in ACD (pre-op to Pt annulus) after treating the first annulus was 0.11±0.04 mm, with a p-value of p=0.0001. The average added change in ACD ($1^{st}$ annulus to $2^{nd}$ annulus) after treating the second annulus was 0.04±0.04 mm, with a p-value of p=0.003 compared to treatment with the first annulus alone.

Changes in Anterior Chamber Depth Using Different Laser Wavelengths

Changes in anterior chamber depth were measured for the method performed at different laser wavelengths, for example 1.4-2.01 μm wavelengths, and delivery of the total energy over different periods of time, such as 100-200 s, for example 105-156 s, and delivery of different total energies, such as 30-100 J, for example 42-62 J.

Pig eyes were trimmed of muscle and fat, soaked in water at room temperature for at least 15 minutes, loaded onto a suction ring with major axis along length and narrower limbus segment towards the handle. Thealoz Duo 3X 4 drops were placed on pig eye cornea, and the suction ring was loaded onto a Casia2 video imaging alignment fixture, sequential user ID and pig eye #were selected with preop cataract protocol and cornea scan on the 2A.R software version. The pig eye was adjusted in the fixture for tip/tilt minimization as seen on the OCT V&H scan and scans were saved. Front Camera report was selected and the images exported to Photo Export folder.

It was confirmed that the laser was spatially (Center, Scale Zap-it Burn paper) and Power delivery calibrated (Gentec). The suction ring and pig eye were transferred to the laser cone, oriented in the same way throughout the experiments. Thealoz Duo 3X 4 drops were added to the pig eye cornea. Once the limbus of pig eye was manually centered under the cone as seen on the camera image, eye placement was considered "registered" to begin treatment. Upon completion, Thealoz Duo 3X 4 drops were placed on pig eye cornea, and the ring and eye to alignment fixture were moved on the Casia2 OCT. Post-op OCT scans were taken with the same pre-cataract cornea protocol.

The mechanism for angle opening is circumferential anterior zonular tightening at the scleral insertion, resulting in an increase in pupillary ACD perpendicular distance and the iridocorneal angle. There is less of a requirement for a precise custom treatment pattern near the limbus which can be avoided by a large margin (at least 1 mm) if Schlemm's Canal is not to be treated. Outcomes for a 2.01 μm and 1.48 μm laser were compared, and it was demonstrated that it is possible to open the angle with high confidence without using a custom limbus patterned plan (all eyes in a group received the same treatment). The ability to open the angle without a custom pattern permits a more efficient, less costly treatment, for example in a largely Asian angle closure patient demographic. Outcomes for the 1.48 μm laser (Group 1) compared to 2.01 μm laser (Group 2) were not statistically different. Group 1 on average took 156 secs depositing 62 J while Group 2 on average had slightly better outcomes and took 105 secs depositing only 42 J.

To better mimic an angle-opening procedure, pig eyes exhibiting some angle closure were used, so the post-treatment angle-opening metric was a more relevant measure. Pig eye angle closure was induced by increasing refrigerated storage so that the eyes were at least 2 days old and some were 3 days old. A corresponding increase to the laser duration (reps) from 3 to 5 still only applied 42 J of total energy. This shelf life showed a significant and duration-dependent capsular bag turgidity with angles reduced compared to freshly obtained ones. Prior experiments have shown reduction in capsular warpage ("Capsular Roughness Index") with such posterior scleral annular treatments.

Experimental testing was also performed on an aphakic pig eye. The treatment annuli did not have any effect on the pupillary ACD as would be expected because the equatorial stretch has no capsular bag on which to exert tension and increase ACD. This data supports a mechanism which is primarily lenticular/zonular (high post-cataract similarity) and the need to be near the limbus is only necessitated when opening the SC. The anterior direction of the aphakic pupil-cornea motion, iris scleral insertion bend angle increase and some reduction in the PD suggests, in intact pig eyes, there is a balance between forward shrinkage forces due to the anterior annuli and shrinkage induced centrifugal forces (capsular molding) due to the AEZ (anterior equatorial zonules) stretching from posterior laser annuli. This is believed to minimize post-Op induced effective lens position (ELP) drift.

Pig eye direct TISA measurements on the OCT indicated in one example comparing pre-treatment to post-treatment ΔTISA, ΔAOD and ΔTIA, and increase over 25% with only a 4 degree 9% pupil-ACD (extended TISA).

| 255 Sup | ΔAOD | ΔARA | ΔTISA | ΔTIA |
|---|---|---|---|---|
| % | 39.86 | 68.75 | 64.84 | 23.01 |

ACD increased, P-ACD increased, PD reduced, TISA. All these changes are measurable at statistically significant levels on a total of 76+ eyes (so far). However, aphakic eyes are not benefited (although they are seldom affected by a narrow angle either). A posterior scleral 2.01/1.93/1.48 μm laser exposure is therefore considered effective for minimally invasive ab externo treatment to achieve circumferential angle opening.

TABLE 7

Changes in Anterior Chamber Depth (ACD) at different wavelength laser treatments

| Exp No. | N | Δinf | ΔSup | ΔACD | Avg ΔACD | Laser (um) |
|---|---|---|---|---|---|---|
| 1 | 12 | 0.0008 | 0.006 | tbd | | PE 1.48 |
| 2 | 8 | 0.0064 | 0.001 | 0.001 | 60 | 2.01 |
| 3 | 10 | 0.0003 | 0.0001 | 0.0002 | 60 | 2.01 |
| 4 | 7 | 0.041 | 0.024 | 0.007 | 60 | 2.01 |
| 5 | 9 | 0.17 | 0.0002 | 0.004 | 60 | 2.01 |
| 6 | 10 | 0.0018 | 0.0002 | 0.005 | 50 | 2.01 |
| 7 | 10 | 0.460 | 0.216 | 0.423 | 0.01 | sham |
| 8 | 10 | 0.079 | 0.094 | 0.030 | 60 | 1.48 |
| 9 | 10 | 0.079 | 0.094 | 0.030 | 70 | 1.48 |
| 10 | 6 | 0.079 | 0.094 | 0.030 | 110 | 1.48 |
| 11 | 7 | 0.002 | 0.001 | 0.0001 | 180 | 1.48 |
| 12 | 7 | 0.000 | 0.064* | 0.0014 | 130 | 1.48 |
| 13 | 5 | 0.048 | 0.228 | 0.0012 | 160 | 1.48 |
| 14 | 9 | 0.011 | 0.184 | 0.0134 | 80 | 1.48 |
| 15 (N total) | 120 | | | Avg ΔACD μm* *excl sham | 90 | |

*controls: S&I subluxation effects noted
The 1.48 μm laser generally produced greater average changes in the ACD.

Patient Interface and Heat Sink

In many embodiments a patient interface is used to apply the treatment energy to the eye at the desired locations described herein. In some embodiments the patient interface can perform multiple functions during treatment, such as helping stabilize the position of the eye, coupling a source of light energy to the eye, providing an interface for imaging the treatment area, and/or providing a heat sink for coupling to the conjunctiva to protect superficial areas of the treatment area during application of the energy. The location of the heat sink can be fixed in relation to a fixed structure of the laser system to fix the location of the eye, and the heat sink may comprise one or more curved surfaces such as a concave surface to engage the eye. In many embodiments, an arm extends from the fixed structure of the laser system to the heat sink in order to fix the location of the heat sink.

A heat sink material is transmissive to the light energy being applied to the eye and may be made of a material such as sapphire or Zinc Selenide (hereinafter "ZnSe"). The heat sink material can be configured to transmit light energy absorbed more strongly by the stroma than water. The heat sink can be chilled to inhibit damage to the conjunctiva of the eye and can provide improved transmission of light energy when condensation is present, as the condensed water may be less strongly absorbed by the laser beam. In many embodiments, one or more layers of the epithelium of the eye (basal layer, wing layer or squamous layer) remains substantially intact above the zone where the eye has been treated, for example at least one layer of viable epithelial cells can remain intact when the heat sink is removed. Additional information about the structure and composition of suitable heat sink lenses is provided in US20180177632 the disclosure of which is incorporated by reference to the extent it is not inconsistent with the present disclosure.

In some embodiments, the optically transmissive material of the heat sink is shaped and optically configured with smooth surfaces, such as an optically transparent heat sink, for example a lens. The heat sink may comprise a window of the optically transmissive material and can be one or more of many shapes such as a flat on opposing surfaces, plano-concave, or convex-concave. The convex-concave heat sink window may comprise a meniscus shaped lens, having substantial optical power or no substantial optical power, for example.

In some embodiments the treatment apparatus includes an energy source such as a laser and a docking station to retain the eye in a treatment position. In some embodiments the docking station comprises a chilled optically-transmissive heat sink to couple to the eye. The docking station couples to the eye such that the heat sink contacts the conjunctiva of the eye and fixes the working distance of the eye relative to the surgical laser, such that the scleral treatment posterior to the lens equator can be performed accurately. In many embodiments, the heat sink is chilled such that at least one epithelial layer of the conjunctiva of the eye above the treated tissue remains viable, to expedite healing of the eye and decrease invasiveness of the procedure. The chilled heat sink structure can be chilled to a temperature within a range from above the freezing temperature of the eye and saline, at about −3 degrees Celsius (C), to below an ambient room temperature of about 20 degrees Celsius. Alternatively, a heat sink can be provided without chilling.

In many embodiments, the freezing temperature of the eye corresponds to the freezing temperature of saline, for example about −3 degrees. In some embodiments, the apparatus comprises a scanner to scan the laser beam. The laser beam can be pulsed or continuous, and in many embodiments comprises a continuous laser beam configured to inhibit temperature spikes related to ablation of the eye. In some embodiments the laser irradiance comprises a temporal and spatial profile to inhibit transient heating peaks of the tissue that can be related to removal of tissue such as ablation. The scanner can be configured to scan the laser beam in a plurality of quadrants, such as for quadrants with untreated regions between each of the quadrants to inhibit damage to muscles of the eye located between the treatment quadrants.

The cooling methods and apparatus disclosed herein can be combined with the energy sources described herein to decrease heating of tissue near external surfaces of the eye, such as conjunctival and epithelial layers of the eye. Decreased heating of tissue near external surfaces of the eye may result in the tissue near the external surfaces of the eye remaining substantially viable when the tissue below it is treated. This may for example be done to inhibit pain and swelling of the eye during and/or after treatment.

Figure 9A:
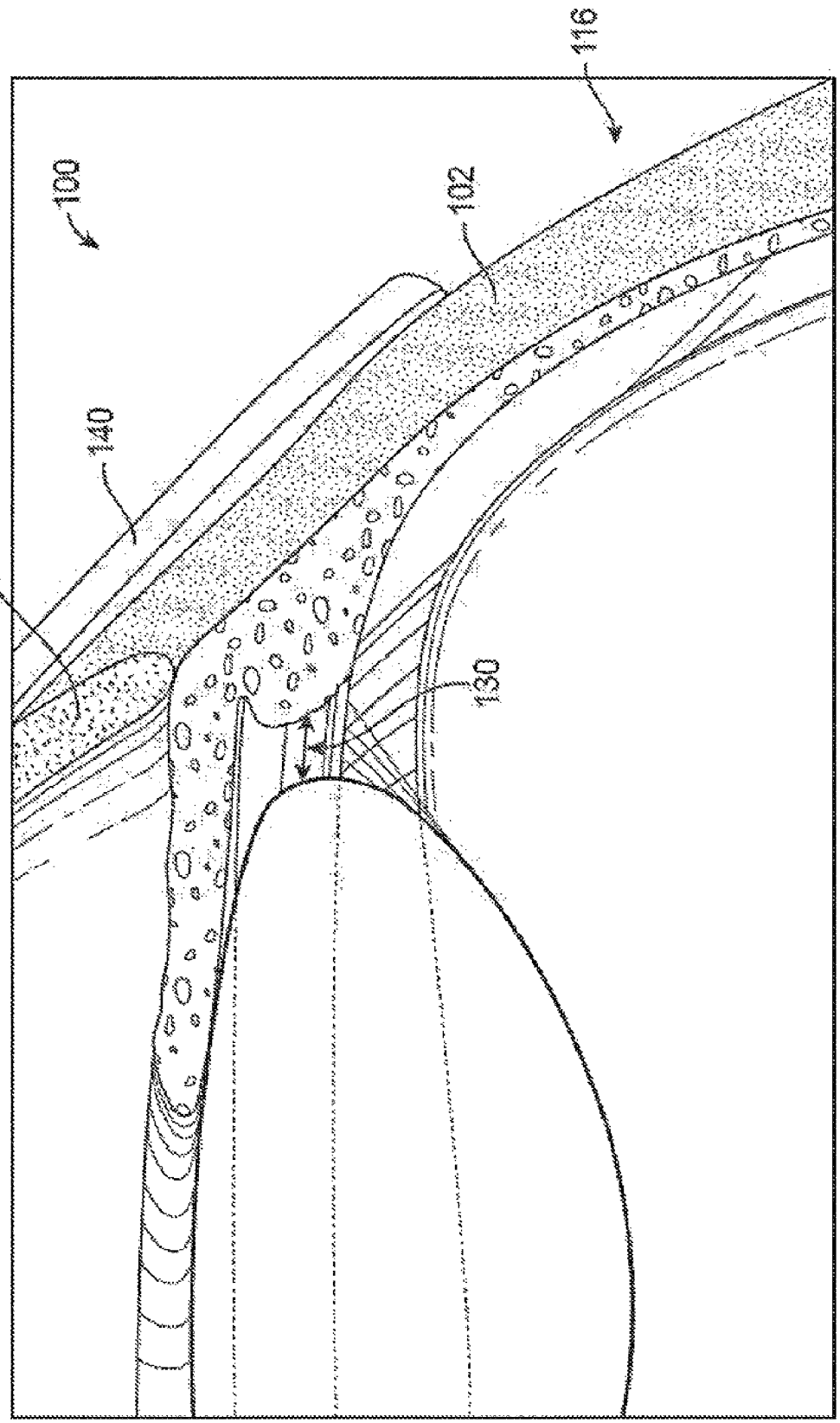
FIG. 9A schematically illustrates a heat sink contact lens applied to the surface of the eye to cool the surface of the eye during the angle-opening treatment.

FIG. 9A illustrates a heat sink 140 placed over the eye 100 of FIG. 1 to cool the surface of the eye during the treatment of glaucoma, in accordance with the methods disclosed herein. The heat sink 140, for example a chilled contact lens, can be inserted over an outer portion of the eye 100 including the cornea 104, sclera 102, and conjunctiva 116, to conduct heat away from the outer portion of the eye 100 during the treatment procedure. The heat sink can be made of any suitable material and may include a material transmissive to wavelengths of light energy (e.g., sapphire or diamond-like carbon transmissive to certain wavelengths of IR light), so that the eye tissue beneath the heat sink can be heated with absorbed light energy.

Figure 9B:
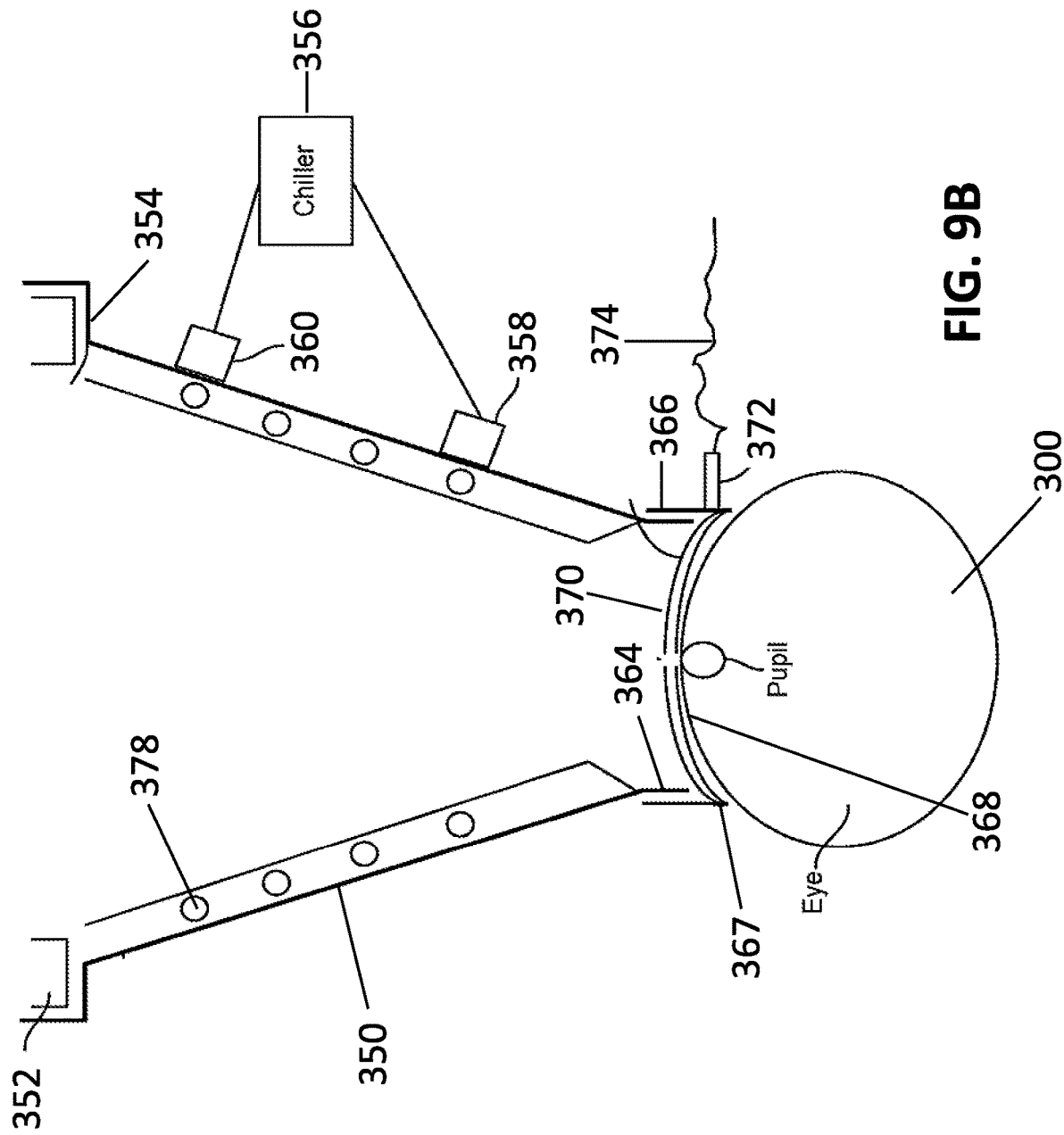
FIG. 9B is a cross-sectional side view of a patient interface for coupling an energy delivery system to the eye with a patient fixation ring and a heat sink contact lens.
Figure 9C:
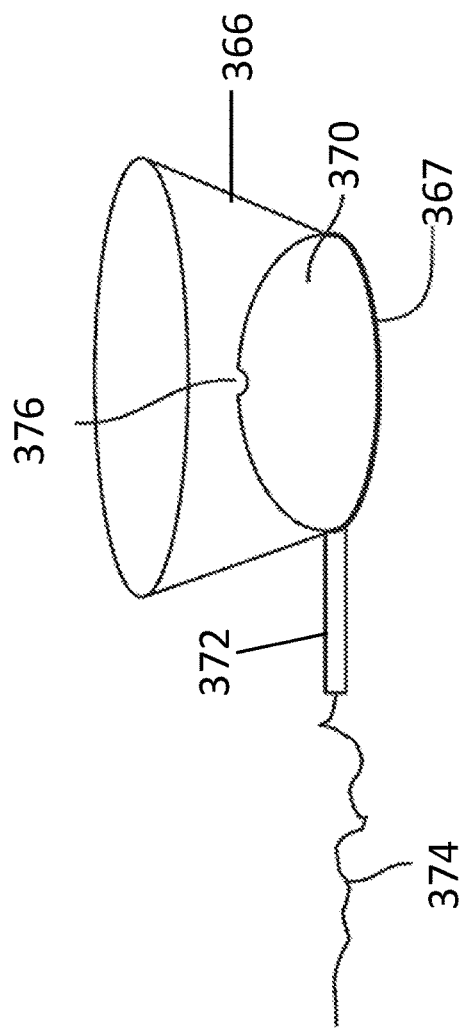
FIG. 9C schematically illustrates a coupling into which the energy delivery system is introduced.
Figure 9D:
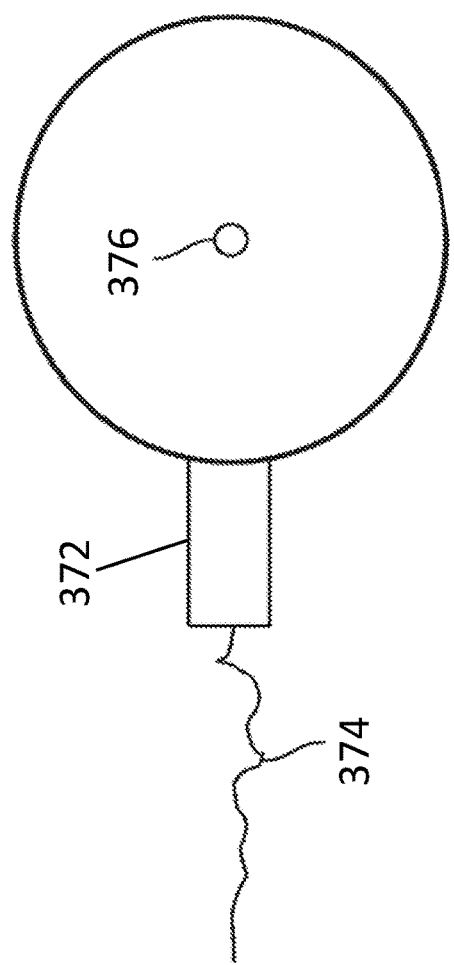
FIG. 9D is a top view of FIG. 9C.

FIGS. 9B, 9C and 9D show a structure for coupling an energy source to a surface of an eye 300. FIG. 9B shows a cross-sectional side view of a cooling member shaped as a frustum of a cone 350 that tapers in diameter from an open larger-diameter proximal end to a narrow open end of circular cross-section. Cone 350 may be made of a high thermal conductivity material such as metal (for example steel), and contains a laser support structure 352, optics tray 354, chiller 356, and couplings 358, 360 for cooling cone 350. The laser support structure may support one or more laser sources, as described herein. The optics tray may support one or more optical components that direct one or more lasers to a surface of an eye, as described herein. The narrow open end of cone 350 terminates in a peripheral lip 364 that is parallel to the longitudinal axis of cone 350. Peripheral lip 364 docks in a compression fit with a receptacle 366 that includes a circular peripheral silicone fixation ring 367 for seating against the anterior surface 368 of the eye 300 to be treated. The support structure provides the energy source to apply the therapeutic energy to the designated treatment locations on the surface of the eye. A heat sink contact lens 370 is retained within and coupled to the bottom of receptacle 366, for example within fixation ring 367, for placement on the eye as a heat sink. A suction port 372 communicates with the interior of receptacle 366 below fixation ring 369 to maintain fixation ring 368 against eye 300.

FIG. 9C shows a transparent schematic side view of an illustrated structure for coupling the energy source to the surface of eye 300. Fixation ring 367 surrounds the bottom edge of contact lens 370 to form a light seal under negative pressure against the eye to help maintain the eye in position during the procedure. A central fluid flow opening 376 may be provided in contact lens 370 to drain cooling fluid from receptacle 366, whence it is then removed through suction port 372 and tubing 374. Suction in tubing 374 may be provided by connecting a syringe to the suction tubing and withdrawing the plunger within the syringe. Alternatively, the suction tubing may be connected to a conventional vacuum source with a vacuum pressure sensor. FIG. 9D shows a top view of the coupling structure of 9C for coupling an energy source to a surface of an eye. The coupling structure may be configured to remove heat from a surface of an eye, for example being composed of a material having a high thermal conductivity such as metal.

The heat sink contact lens 370 seated within fixation ring 367 is configured to fit against the cornea and/or sclera of an eye, and may be composed of a material having a high thermal conductivity, such as sapphire, diamond or a diamond-like material. Contact lens 370 may be of a uniform thickness, or it may taper or thicken from the center to the peripheral edge. Opening 376 may be located at approximately the center of contact lens 370 to provide a pathway for the flow of fluids (such as air or liquids) away from the eye. Contact lens 370 may have an outer diameter of about 15 mm, 16 mm, 17 mm, 18 mm, 19 mm, or 20 mm. In particular examples, contact lens 370 has an outer diameter of less than 15 mm or greater than 20 mm Contact lens 170 may have a thickness of about 0.5 mm, 1 mm, or 1.5 mm. The heat sink contact lens may have a thickness of less than 0.5 mm, or may have a thickness of greater than 1.5 mm.

The patient interface may be positioned on a counter-weighted moveable arm such that no weight rests on the eye when the cone 350 is docked to patient fixation ring 367. Cone 350 provides a fixed working distance such that the distance between the surface of the eye and the energy source carried by cone 350 may be constant between patients. Cone 350 may be thermally controlled, for example with a fluid-based (such as water-based) heat exchanger or Peltier cooler, to help maintain the desired temperature of the patient interface and/or contact lens. Controlling the temperature of the cone may allow the preservation of tissues within the eye during an interaction with an energy source. For instance, cooling cone 350 may allow for the preservation of the epithelium during heating with a laser source.

In some embodiments, the temperature of cone 350 may be thermally controlled using a fluid-based heat exchanger. Cone 350 may comprise one or more fluid channels such as channel 378 in FIG. 9B. The fluid channels may be fluidically coupled to a chiller through one or more couplings and one or more tubes or hoses. The couplings may be threaded couplings or compression couplings. The chiller may circulate a cooling fluid (such as water, ethylene glycol, or another liquid coolant) through the fluid channels to cool the cone. The chiller may cool cone 350 to a temperature less than 37° C., less than 30° C., less than 25° C., less than 20° C., less than 15° C., less than 10° C., less than 5° C., or less than 0° C. The chiller may comprise a water exchanger which, for example, has a lateral footprint of approximately 8 inches×8 inches and draws an electric power of approximately 160 W.

If cone 350 is thermally controlled using a thermoelectric cooler such as a Peltier cooler, the cooler may be located on the counter-weighted moveable arms and placed in thermal connection with the heat sink lens. The Peltier cooler may cool the cone to a temperature less than 37° C., less than 30° C., less than 25° C., less than 20° C., less than 15° C., less than 10° C., less than 5° C., or less than 0° C. In some embodiments, the thermoelectric cooler may be a disc-shaped thermoelectric cooler located on the top of the patient interface cone.

The system may be operated by optionally applying vacuum to the eye by drawing suction through port 372 and tubing 374, aiming an illumination beam at the eye from optics tray 354, and obtaining an OCT image of the eye. The OCT image may provide a baseline image of the eye prior to treatment. A treatment may be started once the heat sink contact lens has been secured in place on the eye by the negative pressure or vacuum. An OCT image may also be obtained following treatment and compared with the baseline image to obtain a precise measurement of changes induced by the treatment.

In some instances, medicaments may be added to the eye prior to and/or after treatment to further protect the corneal surface against thermal insult and/or stabilize treatment effects. Eye drops may contain medicaments which sequester and/or protect against collagen degradation and may be applied to the eye prior to and/or after treatment. In some instances, the medicaments may be collagen-sparing. The eye drops may contain medicaments such as hyaluronate or the like, polymers such as hydroxypropyl methylcellulose, and/or dissacharides optionally selected from the group consisting of Sucrose (table sugar, cane sugar, beet sugar, or saccharose), Lactulose, Lactose (milk sugar), Maltose (malt sugar), Trehalose, Cellobiose, Chitobiose, Kojibiose, Nigerose, Isomaltose, Trehalose (for example β,β-Trehalose or α,β-Trehalose), Sophorose, Laminaribiose, Gentiobiose, Turanose, Maltulose, Palatinose, Gentiobiulose, Mannobiose, Melibiose, Melibiulose, Rutinose, Rutinulose, Xylobiose, and any combination thereof.

In some instances, a topical anesthetic may be applied to the eye prior to or after treatment. Such anesthetics may include anesthetics with a tropane skeleton optionally selected from the group consisting of the Amylocaine, Articaine, Benzocaine, Bupivacaine, Butacaine, Carticaine, Chloroprocaine, Cinchocaine/Dibucaine, Cyclomethycaine, Etidocaine, Eucaine, Fomocaine[55], Fotocaine[55], Hexylcaine, Levobupivacaine, Lidocaine/Lignocaine, Mepivacaine, Meprylcaine/Oracaine, Metabutoxycaine, Phenacaine/Holocaine, Piperocaine, Pramocaine/Pramoxine, Prilocaine, Propoxycaine/Ravocaine, Procaine/Novocaine, Proparacaine/Alcaine, Quinisocaine, Risocaine, Ropivacaine, Tetracaine/Amethocaine, Trimecaine, and any combination thereof.

Figure 10:
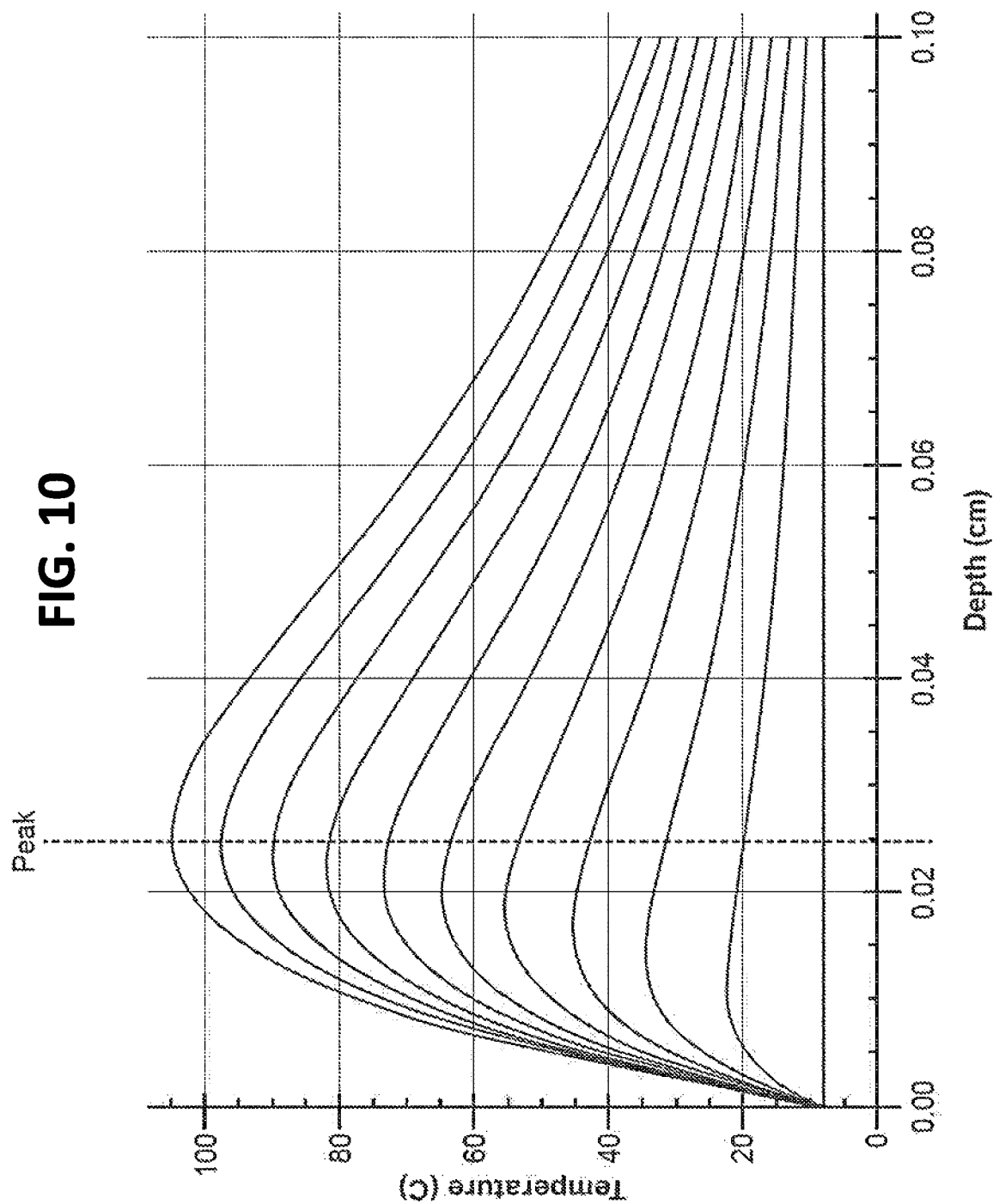
FIG. 10 shows temperature profiles of an eye treated with a laser beam with the eye coupled to a chilled lens, in accordance with embodiments.

FIG. 10 shows temperature profiles of an eye treated with a laser beam with the eye coupled to a chilled lens based on computer modeling. FIG. 10 shows a plot of a finite element analysis model of temperature (in degrees C.) as a function of scleral tissue depth (in mm). The modeling was performed with commercially available COMSOL finite element software to model heat transfer and tissue temperature with energy delivered to the sclera. Temperature profiles of an eye treated with a 2.1 μm laser beam were simulated with the eye coupled to a chilled lens using computer modeling. The finite element analysis assumed anisotropy in the radial and axial dimensions. Each line represents a different amount of energy deposited within the tissue. Changes in the simulated power and/or time were used to alter the total simulated energy deposited within the tissue. For each of the treatment parameters simulated, the tissue reached a peak temperature at about 250 μm deep. The simulation was conducted assuming a laser intensity of 200 W cm$^{-2}$ and tissue absorptivity at 2.1 μm of 20 mm$^{-1}$. The total amount of energy deposited and peak temperature is related to the treatment time. These plots show increased peak temperatures and deeper locations of the peak temperature with increased treatment times.

The chilled lens was modeled at the surface with a fixed temperature of about 6 to 8 C, assuming that the lens would remain at the substantially the same temperature to which it was cooled prior to or during (via active cooling methods) treatment. Such temperatures may for example be reached by placing a cooled lens on the surface of the eye for a predetermined amount of time, for example about 10 to about 30 seconds, prior to initiating treatment as described herein. The amount of time sufficient to cool and protect the surface of the eye may vary depending on the thickness of the cornea and the extent of suction applied by the system to maintain contact between the lens, patient interface, and the surface of the eye.

In some instances, a temperature of about 60 to about 70 degrees may be reached at a depth of about 50 μm to about 400 μm in the sclera. A temperature of about 60 to about 70 degrees may be reached at a depth of about 50 μm to about 300 μm in the cornea. The conjunctiva and/or the epithelium may remain substantially intact during heating of the underlying tissue due to the use of a cooling element or heat sink, such as a chilled contact lens, to inhibit damage to these sensitive surface tissues of the eye. The surface of the sclera may be chilled so as to remain at or near 4 C.

Energy Sources

The angle-opening procedure and apparatus employs an energy delivery system configured to delivery energy to tissue of the eye, such as the sclera. One or more of the energy source, processor, or energy delivery system may be configured to deliver energy to the eye and shrink scleral tissue to exert tension on the zonules, flatten the lens, and increase the iridocorneal angle. The energy sources may include, for example, one or more of light energy, ultrasound energy, high intensity ultrasound energy, mechanical energy, radiofrequency energy, electrical energy, thermal energy, electroporation, microwave energy, optoporation, photonic desincrustation, or galvanic desincrustation.

The energy described above may originate from an energy source, e.g. a laser, such as a pulsed laser or a continuous laser. In some instances, the energy source may be configured to generate energy having a wavelength within a range from about 1.5 μm to about 2.1 um. Optionally, the energy may have a wavelength equal to or less than about 0.8 um, 1 um, 1.2 um, 1.4 um, 1.6 um, 1.8 um, 2.0 um, 2.2 um, 2.4 um, 2.6 um, 2.8 um, or 3.0 um.

In some instances, the energy source may direct energy to the eye with a power from about 50 mW to about 900 mW. Optionally, the energy source may direct energy to the eye with a power from about 100 mW to about 700 mW. Optionally, the energy source may direct energy to the eye with a power from about 200 mW to about 400 mW. Optionally, the energy source may direct energy to the eye with a power equal to or less than about 10 mW, 25 mW, 50 mW, 150 mW, 200 mW, 300 mW, 400 mW, 500 mW, 600 mW, 700 mW, 800 mW, 900 mW, 1 W, 1.2 W, 1.4 W, 1.6 W, 1.8 W, or 2.0 W.

In some instances, the energy directed to the eye may have a total energy within a range from about 4 J to about 90 J. Optionally, the energy directed to the eye may have a total energy within a range from about 5 J to about 50 J. Optionally, the energy directed to the eye may have a total energy equal to or less than about 1 J, 2 J, 5 J, 10 J, 15 J, 20 J, 25 J, 30 J, 35 J, 40 J, 45 J, 50 J, 60 J, 70 J, 80 J, 90 J, 100 J, 120 J, or 150 J.

In some instances, the energy may be directed to the eye for a duration (e.g. treatment time) within a range from about 4 to 200 seconds. Optionally, the energy may be directed to the eye for a duration (e.g. treatment time) within a range from about 8 to 100 seconds. Optionally, the energy may be directed to the eye for a duration equal to or less than about 2, 4, 6, 8, 10, 12, 15, 20, 25, 30, 35, 40, 45, 50, 60, 70, 80, 90, 100, 120, 140, 160, 180, 200, 220, 240, 260, 280, or 300 seconds.

In some instances, the energy directed to the eye may comprise a cross-sectional beam spot size within a range from about 100 to about 500 um. Optionally, the spot size may be within a range from about 150 to about 400 um. Optionally, the spot size may be within a range from about 200 to about 300 urn. In some instances, the spot size may be a spot size that is applied to tissue near the Schlemm's canal. In some instances, the cross-sectional beam spot size may be within a range from about 100 to about 800 urn, for example about 600 urn.

In some instances, the energy may be scanned along the eye with a scan rate within a range from about 10 to about 100 mm/second. Optionally, the energy may be scanned along the eye within a range from about 12 to about 50 mm per second. Optionally, the energy may be scanned along the eye within a range from about 20 to about 30 mm/second. In some instances, the energy may be scanned along the eye at a rate equal to or less than about 5 mm/s, 10 mm/s, 15 mm/s, 20 mm/s, 25 mm/s, 30 mm/s, 35 mm/s, 40 mm/s, 45 mm/s, 50 mm/s, 55 mm/s, 60 mm/s, 70 mm/s, 80 mm/s, 90 mm/s, or 100 mm/s.

The energy delivered to tissue within a treatment region can be fractionated by exposing tissue to energy at separate times. For example, energy can be delivered to a specific location within the treatment region at a first time and delivered again at a second time so as to fractionally deliver the energy to location of the tissue. The number of times energy can be repeatedly delivered to a region of tissue can be greater than two and can comprise for example 3 to 10 repeated exposures to a region of tissue. The amount of time between successive energy exposures to the region of tissue can be related to a thermal relaxation time of the tissue and generally comprises an amount of time greater than a thermal relaxation time. The thermal relaxation time generally corresponds to an amount of time that it takes for a region of tissue to decay from a peak temperature, e.g. about 60 degrees C., to a temperature within about 37% (1/e) of the pre-exposure temperature, e.g. about 5 degrees C. The thermal relaxation time can be determined experimentally with a thermal camera or computer modelling, for example, as is known to one of ordinary skill in the art. The thermal relaxation time can be related to tissue thermal conductivity and several treatment parameters such as the size of the region exposed to energy, e.g. beam diameter, and the amount of time a region of tissue is exposed to energy with each scan, e.g. scan rate.

The amount of time between repeated applications of energy to a region of tissue can be related to the scan rate and size of the energy beam at the location. For example, with a scan at a diameter of 12 mm, the total length scanned with a first 360 degree pass comprises about 37.7 mm (12 mm*3.14). With a scan rate of 10 mm/s, the total amount of time for a complete 360 degree scan comprises about 3.7 s. For a beam diameter of about 0.600 mm, and a scan rate of 10 mm/s, the amount of time which a region of tissue along the scan path is exposed comprises about 0.06 s (60 ms). For repeated scans of the treatment beam along a similar trajectory with substantially the same diameter without pauses between scans, there is a delay of about 3.7 s between repeated exposures at the tissue location for continuous scanning. For repeated scans of the beam to the tissue location, the fractionation of the energy delivered to the tissue location corresponds to a duty cycle of about 0.159% at the tissue location. Within this framework, a person of ordinary skill in the art can configure the systems as described herein to fractionate the energy delivered to a tissue location in many ways, for example with scanning pulsed energy sources, repeatedly applying substantially fixed energy sources (e.g. an annular handpiece), or scanning continuous energy sources, and combinations thereof.

In some instances, a plurality of repetitions with substantially the same treatment pattern may be used to increase the total amount of energy deposited at the treatment location(s). Increased total energy deposition may lead to a more complete, and optionally more stable, transformation within the tissue. By using a plurality of repetitions to fractionate the energy, the total amount of energy deposited at the treatment location may be fractionated, with the amount of energy deposited per repetition reduced compared to the total energy deposited at the location with the treatment, which may provide for more uniform treatment. Repetitions may be overlapping, for example partially or fully overlapping, for example, and may be offset from each other by a distance, such as a predetermined distance. The number of repetitions may for example be within a range of about 1 to about 1000 repetitions, for example about 10, 20, 30, 40, 50, 100, 200, 300, 400, 500, or 1000 repetitions, or within a range bounded by any two of the preceding values.

In some instances, a plurality of repetitions of the laser may be used to fractionate the treatment energy delivered to a treatment location. Fractionation of the treatment may be provided to increase the total energy deposition at a desired treatment location, or within a desired treatment pattern, while decreasing tissue damage by spacing the energy deposition out over time. For example, a desired treatment location or pattern may receive a plurality of energy pulses over a pre-determined amount of time, with a pre-determined delay between each of the plurality of energy pulses, in order to deposit the desired total energy to the tissue and induce the desired changes (e.g. stretching, relaxation, shrinking, etc.) without overheating or over-dosing the tissue. The fractionation of energy delivery can provide more uniform tissue effects, such as more uniform shrinkage or allow for increasing an amount of tissue effect, such as stretching, by allowing for repeated exposures.

Fractionation of the treatment energy delivered to a treatment location may for example allow for delivery of energy to the tissue without inducing cell death at the treatment location. Fractionation of the treatment energy may for example allow for delivery of energy to the tissue at a level below which the cells are killed but above which certain biological stress mechanisms are induced. For example, fractionation of the treatment energy may be used to deliver energy to the tissue in order to induce a cellular response which may improve IOP, such as the induction of HSP and/or cytokine expression as described herein which may be beneficial in regulating IOP. Any of the systems described herein may comprise a processor configured with instructions to fractionate delivery of the energy to each of a plurality of treatment locations with repeated delivery of energy to said each of the plurality of treatment locations. The fractionation optionally may comprise an amount of fractionation within a range from about 0.1% to about 10%, optionally wherein the range is from about 0.2% to about 5%. The fractionation may optionally correspond to an amount of exposure time for said each location and a time delay between successive exposures to said plurality of locations.

The processor may be configured with instructions to configured repeatedly deliver the energy to each the plurality of treatment locations with a time delay in order to fractionate delivery of energy to said each of the plurality of treatment locations. The time delay may be within a range from about 10 millisecond (ms) to about 60 seconds, for example within a range from about 100 ms to about 30 seconds, within a range from about 500 ms to about 15 seconds, or within a range from about 1 second (s) to about 10 seconds.

While a laser is described, a person of ordinary skill in the art will be able to modify the treatment parameters such that any energy delivery apparatus as described herein may be used to acquire the desired results of treating glaucoma and reduction of intraocular pressure (IOP).

Light Energy Sources

In some embodiments, the light energy comprises wavelengths within a range from about 1 to 6 um, such as from about 1 to 3 um. In many embodiments the light energy comprises wavelengths within a range from about 1.4 to about 2 um, for example about 1.46 μm or 2.01 μm, and other ranges as described herein.

The laser may comprise one or more of many lasers emitting one or more of many wavelengths, such as infrared lasers. In many embodiments, the laser comprises a quantum cascade laser configured to emit light having a wavelength within a range from about 5.8 to about 6.6 um, for example from about 6 to about 6.25 um. In some embodiments, the laser comprises a quantum cascade laser or continuous wave laser configured to emit light having a wavelength within a range from about 1 to about 6 um, such as from about 1 to 3 um. In many embodiments the laser is configured to emit light having a wavelength within a range from about 1.4 to about 2.3 um, for example about 1.46 μm or 2.01 um, and other wavelength ranges as described herein. Such lasers are commercially available and can be configured by a person of ordinary skill in the art for treatment of the eye as described herein.

Ultrasound Imaging

Figure 11:
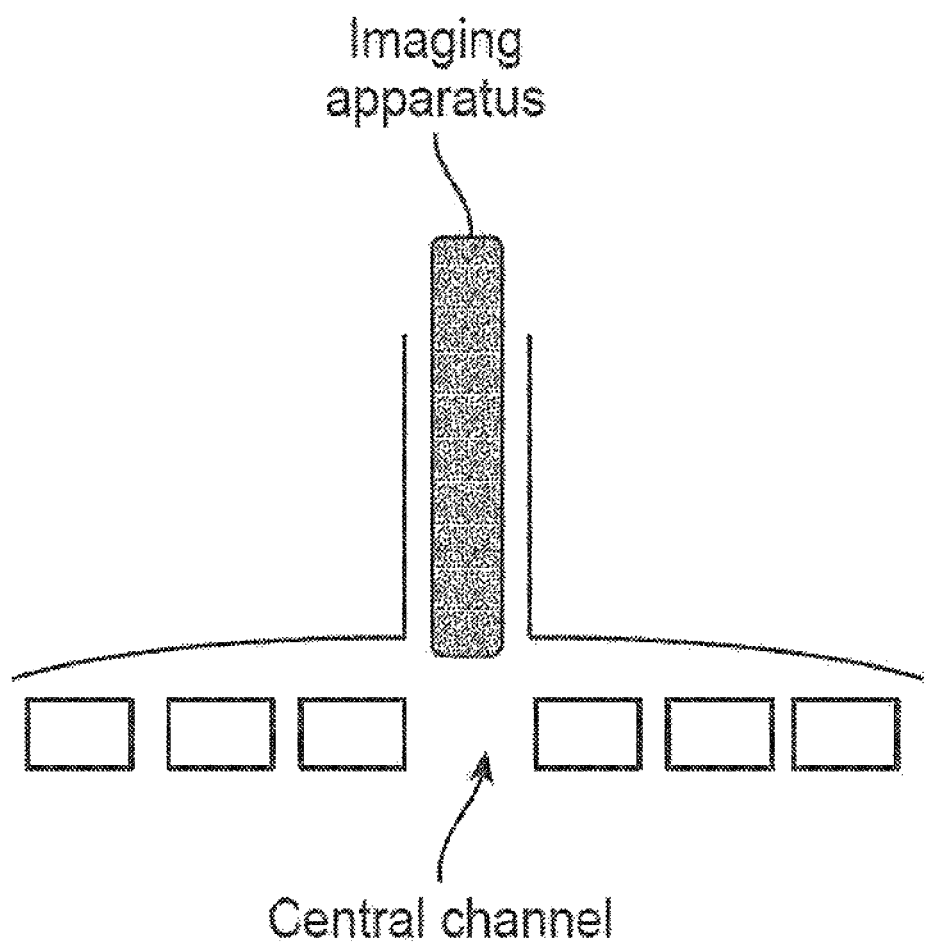
FIG. 11 shows an imaging apparatus, in accordance with embodiments.

FIG. 11 shows an embodiment of an imaging apparatus. The imaging apparatus may be an ultrasound array which in this embodiment includes a transducer with a central channel in which the imaging apparatus may be disposed. In some examples, the imaging apparatus may be an OCT fiber optic cable. The OCT fiber may be disposed inside a channel extending from the center of the energy source and can allow for real-time imaging of tissue at one or more times before, during, or after treatment with the energy source. A number of imaging systems may be used, including but not limited to MRI, UBM, ultrasound imaging, OCT, OCE, or US elastography.

Combination Treatment Methods

Glaucoma is a complex multifactorial disease that has many possible etiologies. The angle-opening method disclosed herein can be used in combination with other modalities of treatment to lower intraocular pressure. For example, the disclosed procedure can be combined with eye drops, or with one or more other glaucoma treatment procedures, to cumulatively lower IOP. By way of example, the other glaucoma treatment procedure may be a procedure for delivering energy to the eye as disclosed in U.S. App. Ser. No. 62/385,234, filed Sep. 8, 2016, entitled "EFFECTIVE OCULAR LENS POSITIONING AND GLAUCOMA TREATMENT METHODS AND APPARATUS," U.S. App. Ser. No. 62/473,269, filed Mar. 17, 2017, entitled "GLAUCOMA TREATMENT METHODS AND APPARATUS," U.S. App. Ser. No. 62/556,228, entitled "GLAUCOMA TREATMENT METHODS AND APPARATUS," PCT/US2017/50799, filed Sep. 8, 2017, entitled "GLAUCOMA TREATMENT METHODS AND APPARATUS," PCT/US2017/023092, filed on 17 Mar. 2017, entitled "EFFECTIVE OCULAR LENS POSITIONING METHODS AND APPARATUS," PCT/US2016/055829, filed on 6 Oct. 2016, entitled "ULTRASOUND DIRECTED CAVITATIONAL METHODS AND SYSTEMS FOR OCULAR TREATMENTS," PCT/US2014/023763, filed 11 Mar. 2014, entitled "SCLERAL TRANSLOCATION ELASTO-MODULATION METHODS AND APPARATUS" and U.S. Provisional Application 62/640,502, filed Mar. 8, 2018, entitled "GLAUCOMA TREATMENT METHODS AND APPARATUS."

Possible outcomes of the glaucoma treatment protocols described herein may include restoration of outflow through one or more of the three primary outflow pathways. Treatment may be used to open closed angle, dilate and/or stretch the trabecular meshwork, dilate and/or stretch Schlemm's canal or the collecting channels, increase porosity and/or dilate vacuoles of the perilimbic sclera, or any combination thereof. For example, PCT/US2017/50799, incorporated herein by reference, discloses treating primary open angle glaucoma by applying the energy to treatment locations on the cornea and sclera within 2 mm of the limbus to promote opening of Schlemm's Canal and facilitate the outflow of aqueous humor from the eye to lower IOP. U.S. Provisional Application 62/640,502 discloses applying energy to treatment locations adjacent the collector channels and/or ostia to dilate the collector channels or ostia to improve uveoscleral outflow of aqueous humor. The movement of collagenous tissue in the sclera and/or cornea from a first location to a second location provides improved treatment with less regression of effect and healing.

Figure 12:
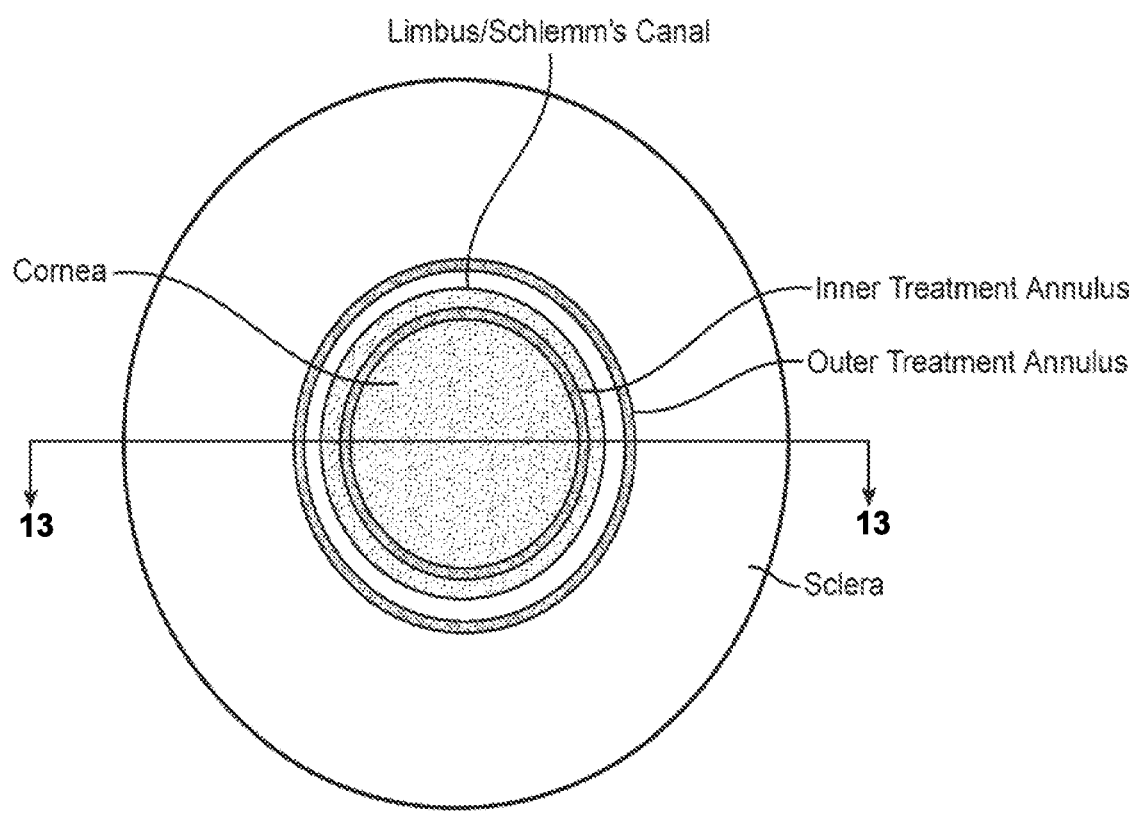
FIG. 12 schematically illustrates a juxtacanalicular treatment pattern for opening Schelmm's Canal which may be used to dilate Schlemm's canal, either alone or in combination with another IOP-lowering treatment, such as the angle-opening method disclosed herein or a collector channel opening method.

FIG. 12 illustrates a juxtacanalicular corneal and scleral treatment pattern within 2 mm of the limbus which may be used to dilate Schlemm's canal, for example in combination with a paralimbal scleral treatment pattern greater than 2 mm from the limbus to increase the depth of the anterior chamber. Two or more juxtacanalicular annuli or rings may be patterned to straddle Schlemm's canal. For example, an inner treatment annulus may be positioned radially inward of Schlemm's canal and an outer treatment annulus may be positioned radially outward of Schlemm's canal. Juxtacanalicular treatment of Schlemm's canal with the inner annulus separated from the outer annulus the may induce improved stretching between the annuli similar to a suspension effect and may improve dilation of Schlemm's canal and/or porosity of the sclera. The inner treatment annulus may be located within the cornea. The outer treatment annulus may be located within the sclera.

When more than one annulus is used for a treatment pattern (for either juxtacanalicular or paralimbal annuli) the inner or outer annulus may comprise a single continuous treatment annulus. Alternatively, the annulus may comprise a single discontinuous treatment annulus with a predetermined amount of space between "dashes" or "spots" of treatment along inner annulus. In some instances, the annulus may comprise a plurality of treatment annuli. The annulus may have a pre-determined width which is made up by the plurality of treatment annuli. The annuli may be overlapping or non-overlapping. For example, the plurality of annuli may be overlapping to generate an annulus with a width greater than the spot size of the energy beam (e.g. laser beam). The plurality of annuli may be non-overlapping, with a pre-determined radial distance between each of the plurality of annuli making up the inner annulus.

The inner and the outer juxtacanalicular annuli may be separated by a distance of about 0.5 mm to about 4 mm. The inner treatment annulus may be located within about 2 mm radially inward of Schlemm's canal. The inner treatment annulus may for example be located about 1 mm radially inward of the innermost edge of Schlemm's canal. The outer treatment annulus may be located within about 2 mm radially outward of Schlemm's canal. The outer treatment annulus may for example be located about 1 mmm radially outward of the outermost edge of Schlemm's canal.

The juxtacanalicular or paralimbal annuli may be circular, or they may be oval, elliptical, egg-like, non-circular, non-elliptical, asymmetrical, or patterned to mimic (e.g. correspond to) the shape of Schlemm's canal or the limbus which may have a non-regular shape. The annuli may be shaped roughly the same as one another or may be differently shaped.

Figure 13:
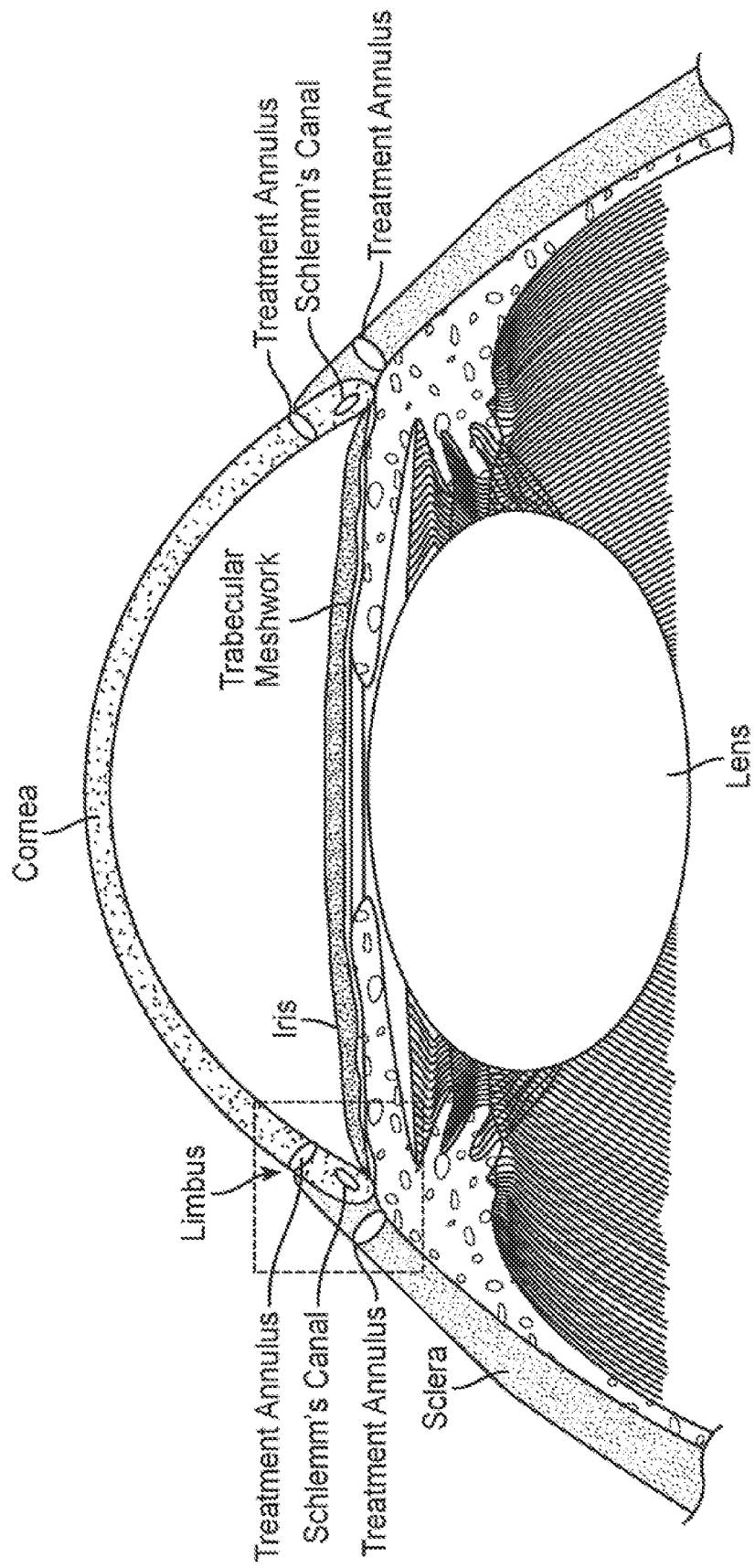
FIG. 13 is a cross-section of the eye of 12 taken along line 13-13 of FIG. 12, showing juxtacanalicular treatment annuli on opposing sides of Schelmm's Canal.
Figure 14:
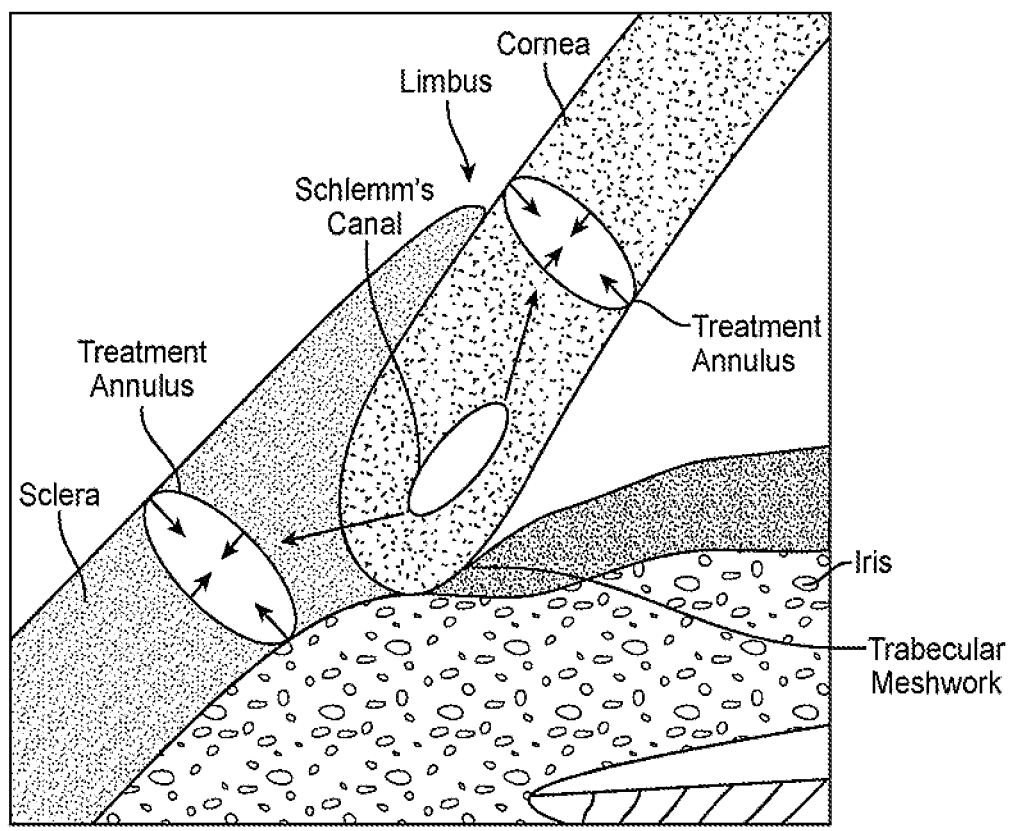
FIG. 14 shows a magnified view of the dashed box indicated in FIG. 13, illustrating contraction of tissue in the juxtacanalicular treatment annuli to exert an opening force on Schlemm's Canal.

FIG. 13 shows a cross-section of the eye of FIG. 12 taken along line 13-13 with treatment annuli located on either side of Schlemm's canal. FIG. 14 shows a magnified view of the dashed box indicated in FIG. 13. The two treatment annuli are positioned to straddle Schlemm's canal. Shrinkage of the tissue within the treatment annuli (as indicated by the arrows pointing inward in the treatment locations on FIG. 14) may generate sufficient strain within the scleral tissue surrounding the treatment locations to open Schlemm's canal. The tissue surrounding Schlemm's canal may be urged towards the treatment locations following treatment (as indicated by the arrows extending from Schlemm's canal in FIG. 14) which may in turn "pull" on the roof of Schlemm's canal and cause dilation and/or translocation of Schlemm's canal, thereby improving aqueous outflow for treatment of glaucoma. Note FIG. 4B in which scleral tissue between Schlemm's Canal and the equator of the lens is contracted to tension the zonules and flatten the lens to increase the idirocorneal angle.

Figure 15:
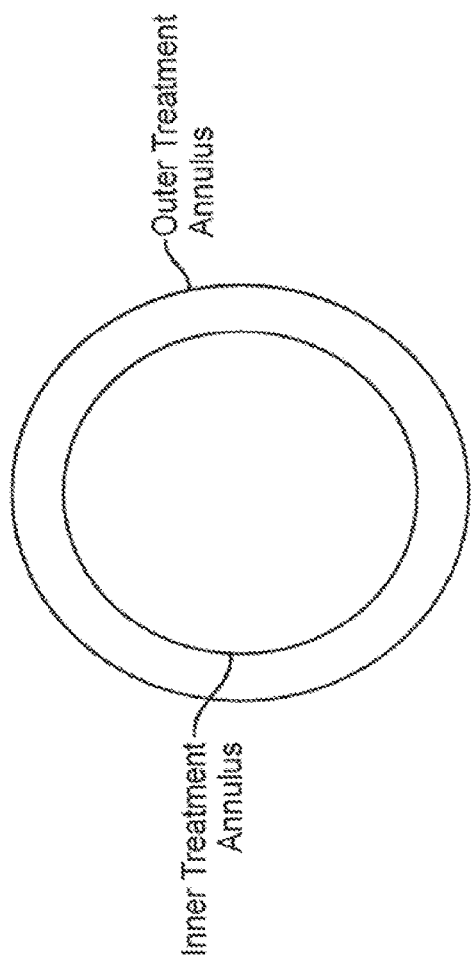
FIGS. 15-16 show possible treatment patterning which may be used to treat glaucoma and dilate Schlemm's canal, or increase the iridocorneal angle, in accordance with embodiments in which multiple treatment annuli are used.
Figure 16:
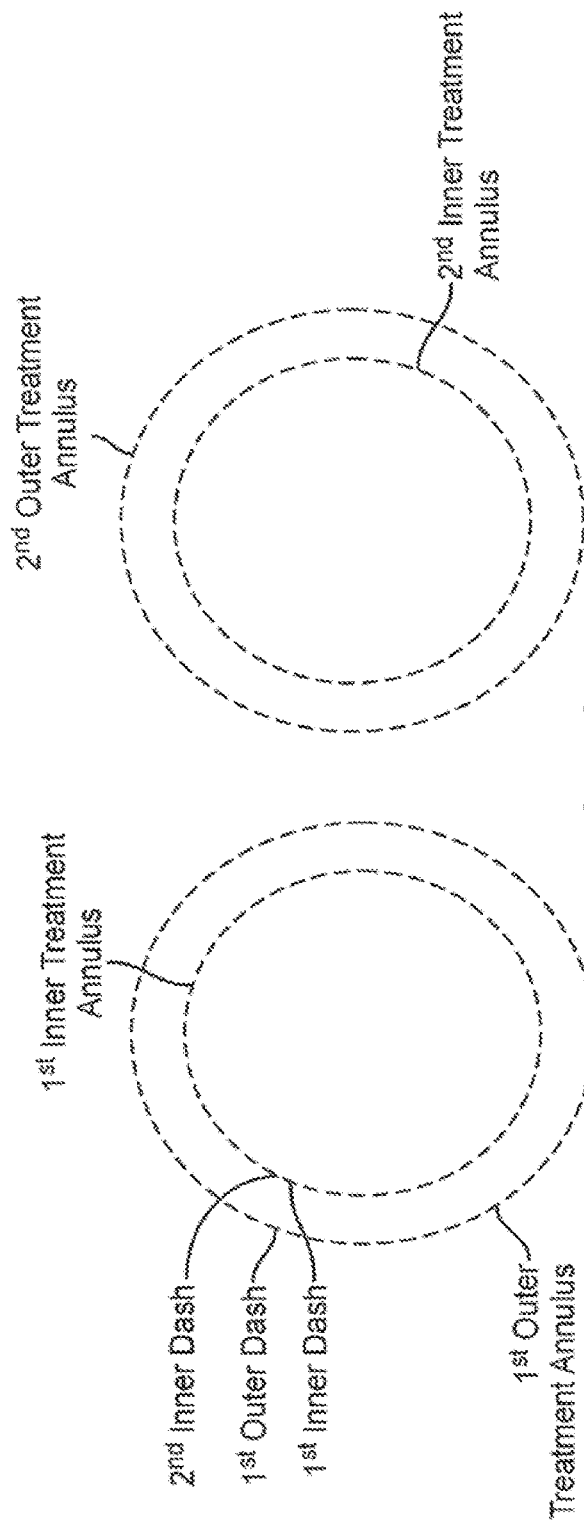

FIGS. 15-16 show possible juxtacanalicular or parlimbal treatment patterning which may be used to treat glaucoma and dilate Schlemm's canal when more than one annular treatment pattern is applied to the eye. FIG. 15 shows two circular annuli, an outer annulus and an inner annulus, which may be patterned onto the eye to straddle Schlemm's canal of be positioned more than 2 mm radially outward from Schlemm's Canal. While circular annuli are shown, it will be understood that any of the treatment patterns described herein may be used as desired.

In some instances, a juxtacanalicular or paralimbal annulus may be created by scanning the energy onto the eye in a continuous annulus. Alternatively, or in combination, the annulus may be created by scanning the energy onto the eye using overlapping pulses from a pulsed laser with a high pulse rate such that the pulses overlap. Alternatively, or in combination, the annulus may be created by scanning the energy onto the eye using non-overlapping pulses. For example, a "mark and jump" technique may be used to generate "dashes" or "marks" of treatment locations along the annulus separated by untreated tissue along the annulus (see FIG. 16 for an example of a dashed pattern). In a second repetition, the untreated tissue may be treated with "dashes" of energy while the previously treated locations may be "jumped" over and left untreated so as to interleave the two repetitions. When both repetitions have been completed, the annulus may be substantially similar to an annulus generated by continuous deposition of energy in a single repetition along the path shown in FIG. 15.

In some instances, the inner and outer annuli may be created using a modified "mark and jump" interleaving technique as shown in FIG. 16. The scanner may be configured to "jump" between a first "dash" on a first inner treatment annulus to a first "dash" on a first outer treatment annulus, then back to the first inner treatment annulus to generate a second "dash" at a predetermined distance from the first "dash" on the first inner treatment annulus. This zig-zag-like pattern of marking between the first inner annulus and the first outer annulus may continue for 360 degrees. The pattern may then be shifted so as to create a second inner treatment annulus and a second outer treatment annulus on a second 360-degree pass using the zig-zag mark and jump patterning. The "dashes" of the second inner treatment annulus may be patterned so as to interleave with and/or overlap with the "dashes" of the first inner treatment annulus. The "dashes" of the second outer treatment annulus may be patterned so as to interleave with and/or overlap with the "dashes" of the first outer treatment annulus. The final energy deposition pattern may be substantially continuous similar to the pattern shown in FIG. 15. The laser generally applies the energy to the eye in the shape of a spot.

In some instances, the plurality of juxtacanalicular or paralimbal treatment locations described herein may comprise a treatment pattern shown, or traceable on a two-dimensional anterior image of the eye. In some instances, the 2-D treatment pattern may be projected onto an eye. In some instances, the 2-D treatment pattern may be displayed on an anterior image of the eye. Optionally, the 2D treatment pattern projected onto the eye may comprise a plurality of locations on either side of a Schlemm's canal on anterior layer of the eye, the anterior layer selected from the group consisting of a cornea of the eye and a sclera of the eye.

In some instances, the plurality of juxtacanalicular or paralimbal treatment locations described herein may comprise a treatment pattern shown, or traceable on a three-dimensional anterior image of the eye. In some instances, a 2-D treatment pattern may be projected onto an eye. In some instances, the 2-D treatment pattern may be displayed on an anterior image of the eye. Optionally, the 2D treatment pattern projected onto the eye may comprise a plurality of locations on either side of a Schlemm's canal on anterior layer of the eye, the anterior layer selected from the group consisting of a cornea of the eye and a sclera of the eye. In some instances, a 3-D treatment pattern may be projected onto an eye. In some instances, the 3-D treatment pattern may be displayed on an anterior image of the eye. Optionally, the 3-D treatment pattern projected onto the eye may comprise a plurality of locations on either side of a Schlemm's canal on anterior layer of the eye, the anterior layer selected from the group consisting of a cornea of the eye and a sclera of the eye.

Figure 17:
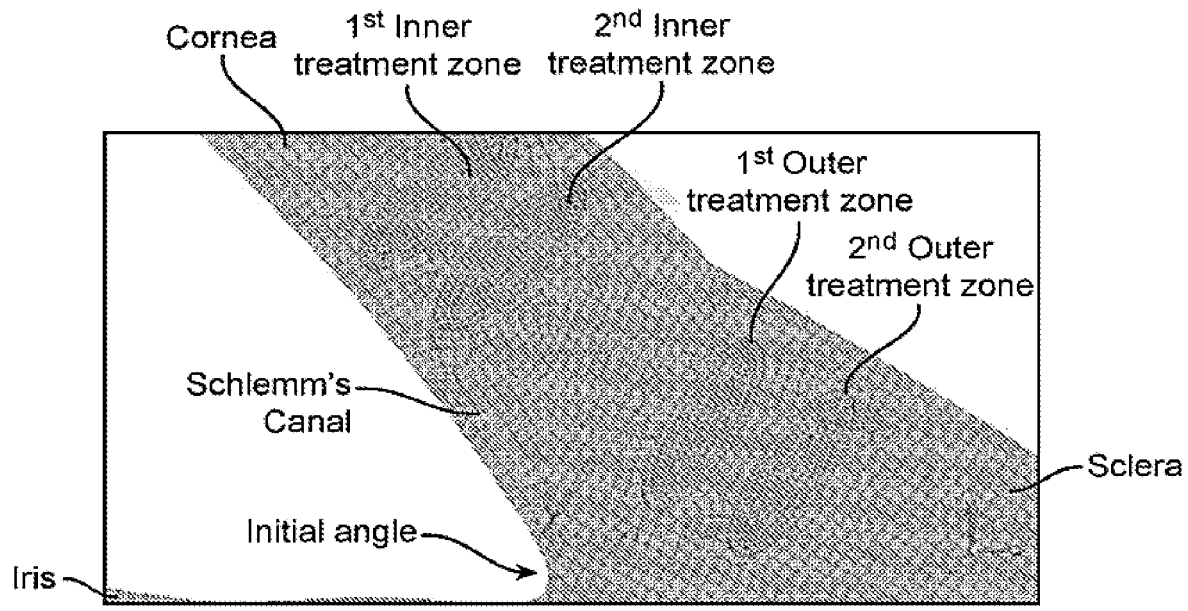
FIGS. 17-18 show the results of a finite element analysis simulation of juxtacanalicular shrinkage treatment of Schlemm's canal, which can be used in combination with the angle-opening method.
Figure 18:
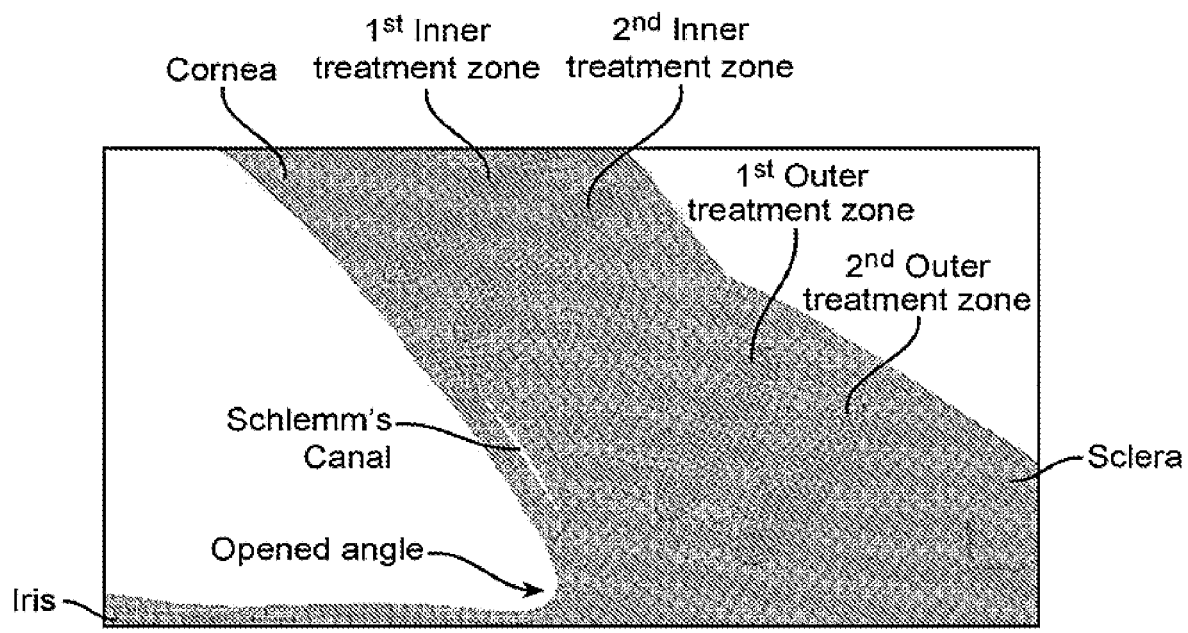

FIGS. 17-18 show the results of a finite element analysis simulation of a juxtacanalicular shrinkage treatment of Schlemm's canal in a simulated axis-symmetric eye with an IOP of 15 mmHg. The ANSYS 17.1 FEM simulation package was used to run the simulation. The cornea, sclera, ciliary body and iris, and laser spots were modeled as varying mesh distributions to mimic the biochemical properties of the tissue within those tissues. The cornea was modeled as hyperelastic, non-linear, and incompressible (with $\mu=1.2$ MPa and D1-0 MPa$^{-1}$). The sclera was modeled as hyperelastic, non-linear, and incompressible (with $\mu=2.4$ MPa and D1-0 MPa$^{-1}$). The ciliary body/iris was modeled as hyperelastic, non-linear, and incompressible (with $\mu=1.2$ MPa and D1-0 MPa$^{-1}$). The laser treatment spots were modeled as hyperelastic, non-linear, and compressible (with $\mu=1.2$ MPa and D1-0.001 MPa$^{-1}$). The cornea limbus was modeled as hyperelastic, non-linear, and compressible (with $\mu=3.8$ MPa and D1-0 MPa$^{-1}$). The cornea under Schlemm's canal was modeled as hyperelastic, non-linear, and compressible (with $\mu=24$ MPa and D1-0 MPa$^{-1}$). The outer edges of the sclera were fixed.

The effects of treating the eye with two annuli radially inward of Schlemm's canal and two annuli radially outward of Schlemm's canal were modeled. Non-overlapping annuli are shown but it will be understood by one of ordinary skill in the art that similar results may be obtained with overlapping annuli (generating a single inner annulus and a single outer annulus of treatment after energy deposition has been completed as described herein, for example as shown in FIGS. 4A and 5A). The first outer treatment zone and second inner treatment zone were positioned 500 μm posterior and anterior to Schlemm's canal, respectively. The second outer treatment zone was positioned 200 μm radially outward from the first outer treatment zone. The first inner treatment zone was positioned 200 μm radially inward of the second inner treatment zone. The effects of the laser were simulated by volume reduction (i.e. shrinking) within the tissue at the indicated elliptical treatment locations. Schlemm's canal was modeled as an approximately 350 μm wide closed channel prior to treatment.

FIG. 17 shows a simulated portion of the eye prior to treatment with an initial angle and a thin Schlemm's canal. FIG. 18 shows the simulation portion of the eye after treatment with Schlemm's canal expanded and angle opened. Localized effects were observed due to tissue shrinkage in the treatment zones. The spots shrunk by about 20% with respect their initial volume (as shown in FIG. 17). Schlemm's canal opened to a width of about 16 um, more than five times its initial width of about 3 um. The initial length of the canal was elongated by about 10 um. The second inner treatment zone and the first outer treatment zone had a larger impact on the opening of Schlemm's canal than the more removed first inner treatment zone and second outer treatment zones. The first inner treatment zone and the second outer treatment zone contributed more to the about 3° opening of the chamber angle. The inventors believe that, by adjusting the treatment parameters, the juxtacanalicular treatments within about 1.5 mm of the Schlemm's canal of the eye can open the angle by an amount within a range from about 1 to 6 degrees. These results also suggest that the size, shape, and portion of the energy spots such as laser spots may be sensitive parameters for the opening of Schlemm's canal. The elliptical shape of the treated zones yielded tissue stretching and contraction tangential to the corneal surface. The simulation showed opening of Schlemm's canal as a result of the elliptical treatments. These results suggest that tissue shrinkage can used to expand Schlemm's canal as described herein.

Juxtacanalicular treatment locations in FIGS. 17 and 18 were modeled such that the inner-most treatment zone and the outer-most treatment zone are generally within about 2 mm of the limbus, for example within about 1 mm of the limbus. These juxtacanalicular treatment locations can provide opening of the angle of the eye with a direct coupling between the sclera and the iris, for example without tensioning zonules of the eye. In the specific example shown in FIG. 18A, the inner-most treatment zone was modeled to be 700 μm from Schlemm's canal (500 μm plus 200 μm for the first inner treatment zone), and the outermost treatment zone was modeled to be 700 μm from Schlemm's canal (500 μm plus 200 μm for the second outer treatment zone). Paralimbal treatment locations, such as those shown in FIGS. 3-4, were more than 2 mm radially outward from Schlemm's Canal and are located to open the angle by tensioning the zonules, flattening the lens, and opening the iridocorneal angle.

Without being bound by any particular theory, the inventors believe that the opening of the angle by about 3 degrees with juxtacanalicular treatment is related to shrinkage of scleral tissue with relatively little opening being related to shrinkage at the corneal treatment locations. The shrinkage of the scleral tissue can induce movement of tissue coupled to the iris to induce tilting of the iris in order to open the angle. The iris can be mechanically coupled to other tissues of the eye, such as the ciliary body of the eye, to induce tilting of the iris so as to open the angle. Because of the penetration depths and locations shown in FIGS. 17 and 18, the angle of the eye can be opened without changing tensioning on the zonules of the eye, that may otherwise induce a change in refraction of the eye as described in PCT application PCT/US2017/023092, filed on 17 Mar. 2017, entitled "EFFECTIVE OCULAR LENS POSITIONING METHODS AND APPARATUS," although combination treatments can be used in accordance with the present disclosure. The scleral treatment locations within about 2.0 mm of Schlemm's can be used to open the angle without substantially changing properties of the lens of the eye, for example. The scleral treatment locations can be configured such that a majority of the treatment energy is located within about 1.5 mm of Schlemm's canal of the eye. The treatment locations can be configured in many ways, for example with instructions to the processor as described herein, with a hand piece having appropriately dimensioned light transmitting structures, or with geometric optics such as masks imaged onto the eye.

The amount of tissue shrinkage and corresponding opening of the angle or Schlemm's Canal can be related to the treatment parameters as described herein, and repeated exposures with energy fractionation can be provided in order to increase or decrease the amount of angle-opening. The processor can be configured with instructions to fractionate delivery of the energy to each of the plurality of treatment locations with repeated delivery of energy to said each of the plurality of treatment locations in order to open the iridocorneal angle to a targeted amount within a range from about 1 degree to about 6 degrees. For example, additional energy and fractionation as described herein can be provided to the eye to increase the amount of opening of the angle. The fractionation may comprise an amount of fractionation within a range from about 0.1% to about 10%, and may be from about 0.2% to about 5%. The fractionation may correspond to an amount of exposure time for said each location and a time delay between successive exposures to said plurality of locations, so as to provide controlled amounts of tissue shrinkage without excessive heating. The fractionation may correspond to a plurality of exposure times to a plurality of locations and a plurality of delay times between a plurality of successive exposures. Additional or fewer locations may also be treated with energy fractionation as described herein.

In some embodiments, the juxtacanalicular or paralimbal treatments correspond to a centroid of the treatment positioned radially with respect to Schlemm's canal. The centroid of treatment can be determined in radial coordinates using known center of mass calculations as is known to one of ordinary skill in the art. The centroid of the treatment can be determined with respect to radial treatment locations. With reference to the $1^{st}$ inner juxtacanalicular treatment zone (700 μm from Schlemm's canal) and the $2^{nd}$ inner juxtacanalicular treatment zone (500 μm from Schlemm's canal), the centroid of the treatment will radially be located approximately 600 μm from Schlemm's canal. With reference to the $1^{st}$ outer treatment zone (500 μm from Schlemm's canal) and the $2^{nd}$ outer treatment zone (700 μm from Schlemm's canal), the centroid of the treatment will be radially located approximately 600 μm from Schlemm's canal, which the optical axis of the eye can be used to approximately define the center of the radial coordinate system. Similarly, for paralimbal treatment zones, they would be modeled more than 2 mm from Schlemm's Canal, for example less than 6 mm from Schlemm's Canal.

While the juxtacanalicular treatments can be configured in many ways, in some embodiments the juxtacanalicular treatment pattern is configured such that the majority of treatment energy is located within about 2 mm of the Schlemm's canal of the eye, for example within about 1.5 mm of the Schlemm's canal of the eye, in order to provide stretching of the trabecular meshwork and opening of Schlemm's canal of the eye. The associated increase in the angle of the eye can be within a range from about 1 degree to about 3 degrees, depending on the juxtacanalicular treatment locations, energy delivery times, and depth profile of treatment. A person of ordinary skill in the art can vary the juxtacanalicular treatment profiles as described herein in order to provide desired amounts to stretching to Schlemm's canal and the trabecular meshwork in order to increase outflow and increase the angle of the eye.

While the paralimbal treatments can be configured in many ways, in some embodiments the juxtacanalicular treatment pattern is configured such that the majority of treatment energy is located on the sclera more than about 2 mm from Schlemm's, for example more than 3 mm, in order to deepen the anterior chamber and increase the iridocorneal angle. In some example, the majority of the treatment energy is applied more than 2.1, 2.2, 2.3, 2.4 or 2.5 mm radially outward from Schlemm's canal.

In embodiments using light energy, the wavelength and exposure time can be configured to provide shrinkage with a desired depth profile, and the cooling structure may be used to inhibit epithelial damage and to provide shrinkage zones beneath the epithelium. Also, depending on the amount of energy, cooling and treatment times used, a portion of the sclera through which energy passes (e.g. light energy) may comprise may be located above (i.e. anterior) to the treatment zone.

Figure 19:
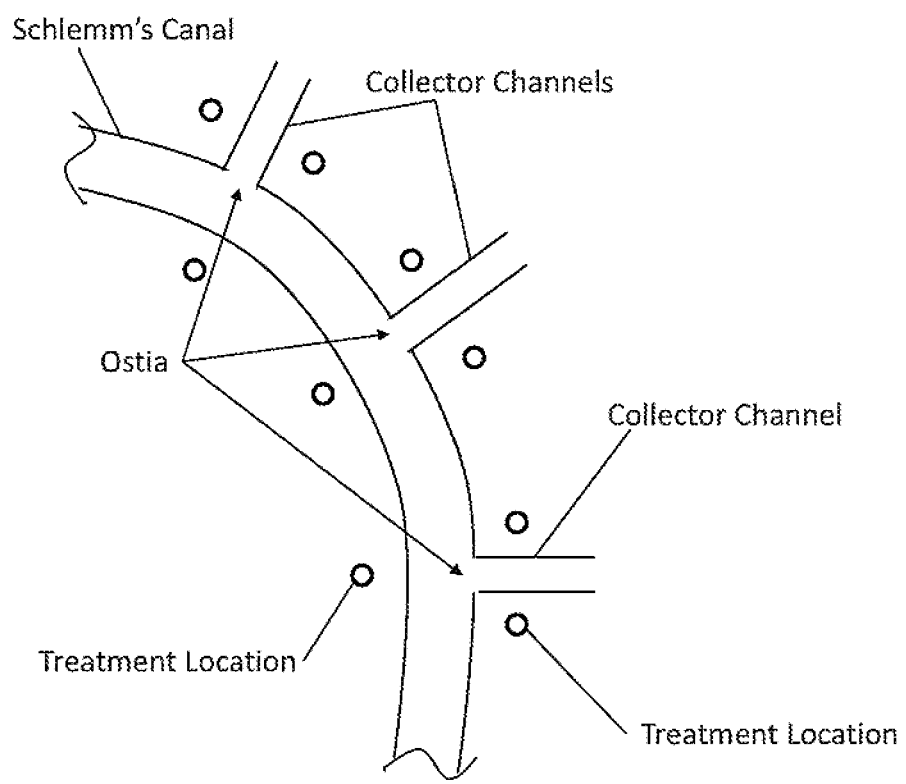
FIG. 19 schematically illustrates a treatment pattern that may be used, in combination with the other methods disclosed herein, to open the collector channels and/or their ostia.

Juxtacanalicular or paralimbal treatment locations may also be combined with treatment locations within 1 mm of the collector channels and/or their ostia to dilate the collector channels of the eye and/or or ostia of the collector channels. FIG. 19 shows a schematic of the targeted anatomy and exemplary treatment locations. The treatment locations shown, for example, are radially adjacent each of the collector channels and opposite the ostia of the collector channels. Once identified, the treatment system may be used to apply energy to the tissue at the treatment locations. Treatment may shrink tissue in these locations and dilate the collector channels and/or their ostia, improving outflow. The energy applied may be any of the therapeutic energies discloses herein such as laser energy and ultrasound. The parameters of the energy delivered may depend on the treatment selected for the treatment location and may be varied as discussed above.

Figure 20:
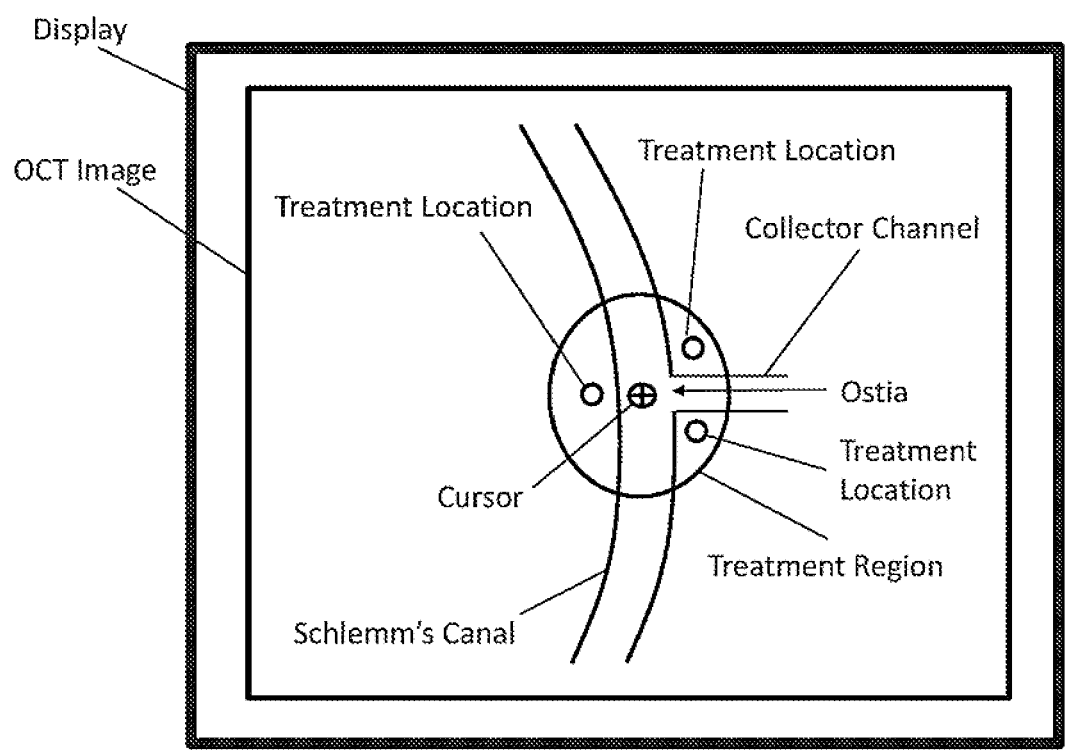
FIG. 20 illustrates the view of a graphical user interface for targeting treatment locations adjacent the collector channels.

FIG. 20 shows an exemplary user interface of a treatment system which may be used to plan a treatment of the eye, such as the treatment of locations within 1 mm of the collector channels. The user interface may include a display such as a touch screen display for the user to view images of the subject and identify treatment locations. A scanner or other image source, such as an OCT scanner, may be used to obtain a sectional image of the eye, particularly a collector channel and the adjacent trabecular meshwork and aqueous plexus. The scanner or other image source may send the sectional image to the system processor which causes the image to be provided on the display. A cursor may further be provided with instructions to identify a treatment location at the collector channel and its ostia. The processor can be configured with instructions to determine the placement of the energy beam as described herein in response to the input treatment region coordinates on the eye and register the target region with the image and physical location of the eye as described herein. A circle, oval, or other visible feature may be overlaid the section image to show the treatment region. The cursor may be centered on the treatment region and the user interface may be provided with control(s) to shrink and expand the treatment region and/or re-locate the cursor with respect to the treatment region. As shown schematically in FIG. 20, various treatment locations may be identified within the treatment region, automatically, semi-automatically, or manually with the identification of the treatment region. The user interfaces may be provided with control(s) to identify specific treatment locations and select treatment regimens for the treatment locations.

Treatment may be patterned or located to open a closed angle, open Schlemm's canal and/or the trabecular meshwork, open collector channels, change fluid bypass characteristics, stretch the trabecular meshwork, and/or improve the uveo-sclera outflow pathway. For example, angle closure may be treated with one or more scleral paralimbal annuli, for example two or more scleral paralimbal annuli. Schlemm's canal closure and/or trabecular meshwork closure may be treated with one or more juxtacanalicular annuli, for example two or more juxtacanalicular annuli, for example a first annulus radially inward from Schlemm's canal and a second annulus radially outward from Schlemm's canal. Collector channels may also be opened by applying a treatment pattern within 1 mm of the collector channels, for example within 1 mm of the collector channels but not on the collector channels.

Increased porosity of the perilimbal sclera and/or dilation or vacuoles may include treatment to relax or stretch the supra-ciliary and/or sub-conjunctival sclera alone or in combination with treatment at the pars plana and/or pars plicata. Treatment to increase porosity may provide reduced intraocular pressure as a stand-alone treatment or in combination with other treatment methods or patterns as described herein. Increased porosity in the mid-stromal near the pars plana and/or pars plicata may for example enhance hydraulic conductivity/transport of the supra-choroidal, ciliary, and/or lymphatic fluid outflow pathways. Treatment may be patterned to flatten the iris in order to open a closed angle. Treatment above the base of the iris root or the roof of the ciliary body may dilate Schlemm's canal and/or stretch the trabecular meshwork. In some cases, it may be beneficial to treat more than one region in a single patient. For example, treatment may be patterned so as to open the angle, open Schlemm's canal and/or the trabecular meshwork, and increase porosity and/or dilate vacuoles of the perilimbic sclera. Treatments directed towards multiple indications may take around 1 minute to about 3 minutes to complete. Treatments directed towards dilating Schlemm's canal may be used to anteriorly expand the roof of Schlemm's canal by about 30 µm to about 100 µm. Changes in the cross-section of the trabecular meshwork and/or Schlemm's canal may cause scleral pores to expand and increase outflow, thereby improving glaucoma.

Treatment using the systems and methods described herein may treat glaucoma improving homeostatic IOP mechanisms to reduce pressure of the eye. For example, heating of one or more of the scleral, trabecular meshwork, or the ciliary body as described herein may induce one or more endogenous biological cellular cascades which may lead to improvements in outflow function. Without being bound by any particular theory, heating of the target tissue with energy such as laser energy may stimulate heat shock protein (HSP) activation, which may lead to normalized cell functions, normalized cytokine expression, and improved auto-regulation of IOP. Such improved function may, for example, be related to opening of one or more of the collector channels, ostia of the collector channels, or the trabecular meshwork.

Treatment using the systems and methods described herein may be configured to treat glaucoma without substantial corneal thinning as measured by axial pachymetry using OCT or US imaging. Corneal thinning may be less than about 15%, for example less than about 10%, or less than about 5% after treatment. Typical day to day variability of corneal epithelial thickness (axial pachymetry) as measured by OCT may be ±15 μm 95% CI. Treatment using the systems and methods described herein may be configured to treat glaucoma with a change (increase or decrease) in corneal epithelial thickness of nor more than 50 um, for example no more than 25 um, or no more than 15 um.

Treatment using the systems and methods described herein may be used to generate or dilate vacuoles in the sclera. Low-powered ultrasound or infrared energy may be delivered to the tissue over a period of time in order to shrink the treatment locations and induce strain within the sclera which can cause stretching and translocation of other parts of the sclera which may in turn produce vacuoles. For example, treatment with 100 mW to 300 mW 2.1 μm laser with a scan speed of 25 mm/sec, spot size of 200-300 μm may be used to deposit about 4 to about 50 Joules of energy to the sclera in about 8 to about 100 seconds. 360 degree thermal treatment of the sclera may generate vacuoles and improve scleral outflow. Alternatively, or in combination, scleral vacuoles may be created by targeting collagen in the sclera using a laser with a wavelength of about 6 um. Alternatively, or in combination, scleral vacuoles may be created using a combination of low-powered light energy and electro-sprayed micro-droplets for non-thermal cavitation as described herein.

Table 8 shows possible treatment parameters which may be used with the system for the methods described herein. The methods and system described herein may be operated with any combination of the parameters listed in Table 8. Exemplary ranges are given for each treatment scheme with preferred values in parentheses next to the ranges. It will be understood by one of ordinary skill in the art that possible parameter values may be taken from within the ranges described, as well as by any two values therein.

Treatment to generate sclera vacuoles may include aggressive treatment using a 360° non-contiguous/non-overlapping annulus of treatment spots in order to generate micropockets which can act as vacuoles in the scleral tissue at and about the pars plana. Juxtacanalicular treatment of Schlemm's canal ("SC") may include one or more 360° treatment annulus radially inward of Schlemm's canal (in the cornea) and one or more 360° treatment annulus radially outward of Schlemm's canal (in or near the sclera). In some cases, both the inner and outer treatment annuli may have the same or different treatment parameters. For example, both treatment annuli may have parameters configured to generate tissue shrinkage as shown in the third column and described herein. Alternatively or in combination, one or more inner treatment annulus may have parameters configured to elasticize (or relax) the tissue as shown in the fourth column. The treatment parameters shown for treatment of the cornea radially inward of Schlemm's canal may be less aggressive than the treatment parameters used for the sclera in order to provide additional protection to the cornea. In some instances, dilation of Schlemm's canal may occur without shrinking the tissue of the cornea inward of Schlemm's canal. In some instances, dilation of Schlemm's canal may occur using decrustation/elasticizing treatment of the cornea inward of Schlemm's canal.

TABLE 8

Exemplary parameters for various treatment locations and effects

| Parameter | Sclera Vacuoles | Radially outward treatment of SC | Radially inward treatment of SC |
| --- | --- | --- | --- |
| Wavelength | 1.5-2.1 μm | 1.5-2.1 μm | 1.5-2.1 μm |
| Total Treatment Time | 0.1-3 min (2 min) | 2-5 min (3 min) | 0.1-5 min (0.5 min) |
| Laser Power | 200 mW-1 W (400 mW) | 300-500 mW (400 mW) | 150-300 mW (200 mW) |
| Scan Speed | 10-50 mm/s (20 mm/s) | 10-50 mm/s (20 mm/s) | 10-50 mm/s (20 mm/s) |
| Tissue temperature | 80 C.-100 C. or more | 60 C.-70 C. | 50 C.-60 C. |
| Beam diameter | 0.4-0.8 mm (0.6 mm) | 0.2-0.6 mm (0.6 mm) | 0.2-0.5 mm (0.6 mm) |
| Treatment Location | Pars plana | 0.2-2 mm (0.5 mm) radially outward from distal wall of SC | 0.2-1 mm (0.5 mm) radially inward from proximal wall of SC |
| Treatment Pattern | 360° non-contiguous annulus of 10 μm-2 mm spots | 180°-360° annulus (or patterned to mimic SC/limbus) | 180°-360° annulus (or patterned to mimic SC/limbus) |
| Treatment Effect | Formation of vacuoles (micropockets) | Shrinkage | Decrustation (Elasticization/Relaxation) |

Patients may be treated using the system and methods described herein to avoid applying energy (i.e. to spare or protect) or reduce the amount of energy deposited at sensitive regions and structures of the eye. The use of a cooling structure, for example a chilled contact lens, the wavelength of the treatment, the treatment dosage, the treatment patterning (for example using a "mark and jump" technique as described herein), and other features of the system and methods described herein may be configured to protect structures such as the epithelium, conjunctiva, Bowman's membrane, epi-scleral veins, Schlemm's canal, trabecular meshwork, limbal stem cells, ciliary body, nerves, collector channels, and/or vasculature of the eye.

Patterned Energy Delivery System and Processor

Figure 21:
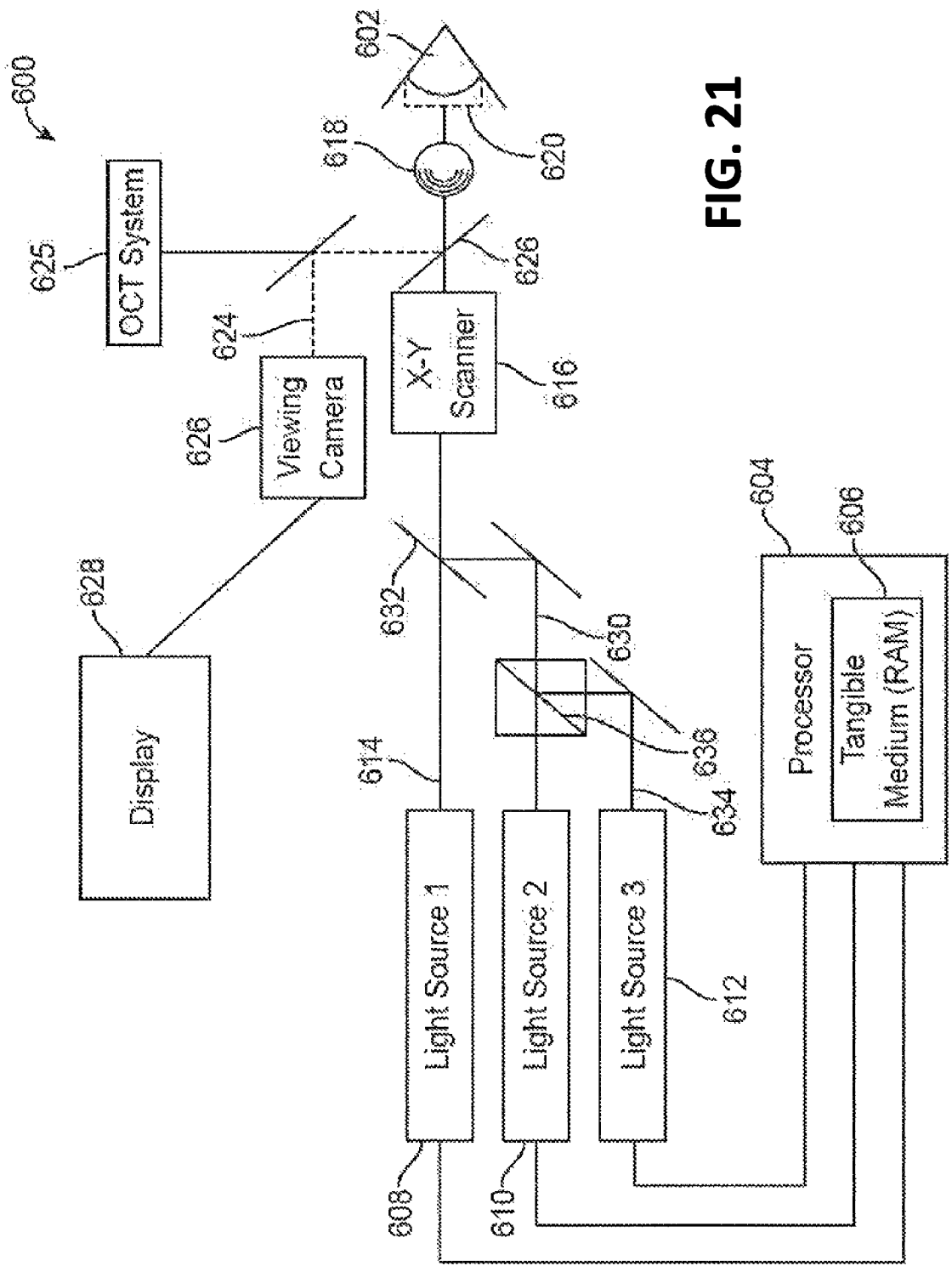
FIG. 21 is a schematic diagram of a treatment system for imaging the eye, displaying an image of a treatment area, processing the information, and controlling the activation of one or more energy source to apply treatment energy to the eye.

FIG. 21 illustrates a system 600 for treating an eye 602, in accordance with embodiments. The system 600 includes a processor 604 having a tangible medium 606 (e.g., a RAM). The processor 604 is operatively coupled to a first light source 608, an optional second light source 610, and an optional third light source 612. The first light source 608 emits a first beam of light 614 that is scanned by X-Y scanner 616 through an optional mask 618 and optional heat sink 620 onto the eye 602. The mirror 622 directs light energy from the eye 602 to a viewing camera 627 coupled to a display 628. An independent non-treatment light source for the optional viewing camera can be provided, for example. The mirror 622 may direct a portion of the light beam returning from eye 602 to the camera 627, for example. The second light source 610 emits a second beam of light 630 that is combined by a first beam combiner 632 with the first beam of light 614 prior to passing through X-Y scanner 616. The third light source 612 emits a third beam of light 634 that is combined by a second beam combiner 636 with the second beam of light 630 prior to passing through the first beam combiner 632.

The processor may be configured with one or more instructions to perform any of the methods and/or any one of the steps and sub-steps of the methods or treatments described herein. The processor may comprise memory having instructions to perform the method, and the processor may comprise a processor system configured to perform the method for example. In many embodiments, the processor comprises array logic such as programmable array logic ("PAL") configured to perform one or more steps of any of the methods or treatments described herein, for example.

The processor may comprise one or more instructions of a treatment program embodied on a tangible medium such as a computer memory or a gate array in order to execute one or more steps of a treatment method as disclosed herein. The processor may comprise instructions to treat a patient in accordance with embodiments described herein.

The processor may be configured with instructions to determine one or more locations of the limbus, and/or one or more locations of Schlemm's canal or the collector channels. In response to the determined location of limbus, for example, one or more locations of Schlemm's canal may be determined. The processor may be configured with instructions to determine a treatment pattern based on the one or more locations of the limbus and/or the one or more locations of Schlemm's canal. The treatment pattern may for example comprise a juxtacanalicular treatment pattern. The processor may be configured to deliver shrinkage energy to the sclera, cornea, or both in order to urge tissue near Schlemm's canal to move towards the treated tissue and dilate Schlemm's canal as described herein. Alternatively, the treatment pattern may be a paralimbal treatment pattern in which the processor is configured to deliver energy to the sclera at least 2 mm from Schelmm's Canal to move the treated tissue and increase the iridiocorneal angle.

The optical delivery system may comprise one or more of the first light source, second light source, third light source, X-Y scanner, optional mask, or a heat sink. The energy may be directed by the optical energy delivery system to the eye or a hand-held probe. In many embodiments, the beams of light 614, 630, and 634 can be scanned onto the eye 602 at a specified X and Y position by the X-Y scanner 616 to treat the eye 602. The X-Y scanner can be configured to scan the combined light beams onto the eye 602 in a suitable treatment scan pattern, as previously described herein. An optional mask 618 can be used to mask the light applied to the eye 602, for example, to protect masked portions of the eye 602 while treating other portions as described herein. An optional heat sink 620 can be placed on the eye 602 during treatment to avoid heating specified portions of the eye 602, as described herein.

The system 600 can be used to apply light energy to the eye 602 in accordance with any suitable treatment procedure, such as the embodiments described herein. In many embodiments, the first light beam 614 has a first wavelength, the second light beam 630 has a second wavelength, and the third light beam 634 has a third wavelength. Each wavelength can be a different wavelength of light. Alternatively, at least some of the wavelengths can be the same. For example, in accordance with the embodiments described herein, the first light beam 614 can have a wavelength suitable to: cross-link an outer portion of the eye 602 and shrink an inner portion of the eye 602; shrink the inner portion and cross-link the outer portion concurrently; shrink the inner portion after the outer portion has been cross-linked; or any suitable combinations thereof. Alternatively, the first light beam 614 can have a first wavelength suitable to cross-link the outer portion of the eye 602, as described herein, and the second light beam 630 can have a second wavelength suitable to shrink the inner portion of the eye 602, as described herein. The third light beam 634 can have a third wavelength suitable to soften a portion of the sclera of the eye 602, as described herein. Any suitable combination of wavelengths of light for applying any combination of the treatments described herein, concurrently or separately, can be used.

The processor can be coupled to each of the light sources to selectively irradiate the eye with light having wavelengths within a desired range of wavelengths. For example, the first light source can be configured to emit light energy having wavelengths in a range from about 1.9 to 2.1 um, the 1/e attenuation depth can be in a range from about 200 to 300 ums, for example about 225 to 275 um. The second light source can be configured to emit light energy having wavelength in a range from about 1.3 to 1.55 um, the 1/e attenuation depth is within a range from about 350 to 450 um. The processor can be programmed with instructions to irradiate tissue with light energy appropriate for the effect at the desired treatment location. For example, the light source emitting light energy in the range from 1.9 to 2.1 μm can be used to treat the cornea, and the second light source emitting light energy with wavelengths in the range from 1.3 to 1.55 μm can be used to irradiate the sclera. The software may comprise instructions of a treatment table so as to scan the laser beam to desired treatment locations as described herein, for example.

The laser system 600 may comprise an OCT system 625, such as a commercially available OCT system. The OCT system may for example be a CASIA2 or CASIA SS-100 OCT scanner (TOMEY). The OCT system may for example be a commercially available OCT system such as one sold by Tomey, Heidelber, Visante, or Optovue. The OCT system can be coupled to the viewing optics and laser delivery system with a beam splitter 626. The viewing optics may for example comprise an operating microscope (such as one sold by Zeiss, Haag Streit, Leica, or Moller Weildel), a slit lamp, or other custom optics. The OCT system can be used to measure the eye in situ during treatment. For example, the OCT system can be used to generate OCT images as described herein in order to generate tomography of the eye to determine the location of target tissues, movement of target tissues, and stretching of target tissues as described herein. The OCT system 625 can be coupled to processor 604 and used to control the laser system with a feedback loop, for example. The processor can be configured with instructions to scan the laser beam on the eye in accordance with the treatment patterns and parameters as described herein.

Figure 22:
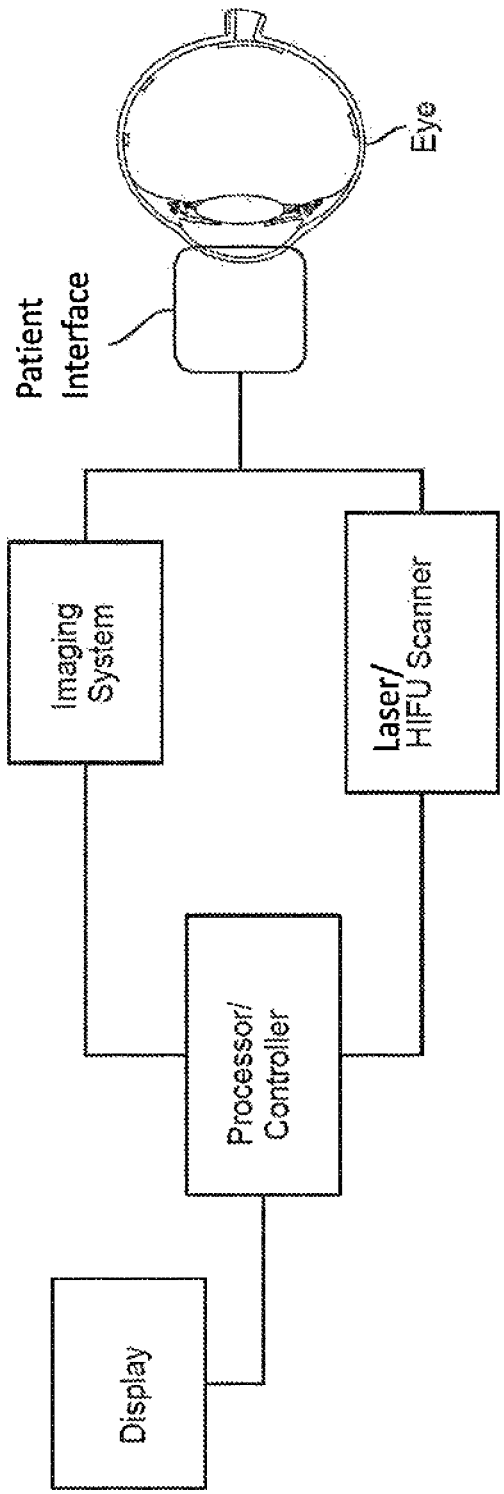
FIG. 22 is another schematic diagram of a treatment system illustrating a patient interface.

FIG. 22 shows another embodiment of a treatment system which may be used for any of the treatment methods described herein. The system may comprise a laser scanner which directs and scans laser energy from a continuous wave or pulsed laser to one or more locations on or inside the eye. The system may comprise a HIFU scanner which directs and scans HIFU energy from a HIFU transducer array to one or more locations on or inside the eye. The scanner may be coupled to a patient interface or patient coupling structure as described herein. The scanner may further be coupled to an imaging system, for example OCT or UBM, as described herein. The imaging system may be used to capture one or more images of the eye before, during, or after treatment as described herein. A processor or controller may be coupled to the energy source (such as a laser) and the imaging system and be configured with instructions to scan the energy beam to a plurality of locations or in one or more patterns and image the tissue during treatment. The system may also comprise a display coupled to the processor that allows the user to visualize the tissue prior to, before, or after treatment. The display may show images which allow the user to see the tissue treated and plan the treatment. Images shown on the display may be provided in real-time and can be used to prior to treatment to allow the user to align the tissue and/or select a treatment zone or pattern to target. Identified target treatment zones may be input by the user to program the treatment depth, location, and pattern in response to the images shown on the display. The imaging system can be used to visualize movement of ocular structures during treatment in order to detect beneficial treatment effects.

The processor can be configured with instructions to treat the eye with laser energy and to image the eye with an embedded imaging apparatus, for example an OCT probe or Ultrasound imager. The processor coupled to the array can be configured with instructions to provide both ultrasound wavelengths from the array. The imaging apparatus may provide additional tissue feedback data in real-time, for example temperature or elasticity. The system as described herein may comprise an eye tracker as known to one in the art in order to generate real-time images of the eye in order to align or register the target treatment regions of the eye. Pre-treatment images can be measured and registered with real-time images obtained during treatment in order to track the location and orientation of the eye.

The glaucoma treatment systems described herein may simultaneously provide imaging guidance, quantitative characterization of the tissue (for example measuring mechanical properties such as elasticity), and/or perform therapeutic tasks. In some embodiments, the treatment system described herein may comprise two or more lasers. The processor may be configured with instructions to treat the eye with a first wavelength of light at a first location (or plurality of locations) and a second wavelength of light at a second location (or plurality of locations). The treatment system described herein may comprise one or more lasers within a range of about 810 nm to about 6 um, for example about 810 nm, about 1.3 μm to about 2.5 μm, about 1.5 μm to about 2.4 μm, about 1.47 μm, about 1.95 μm, about 2.01 μm, about 2.1 μm, about 4 μm to about 7 μm, about 5 μm to about 7 μm, or about 6 μm. Wavelengths on the lower end of the spectrum, for example an 810 nm or 1.47 laser may be used to treat the sclera. A 1.47 μm laser may be about twice as tissue penetrating as a 2.01 μm laser when equidosed. Wavelengths on the upper end of the spectrum, for example within a range of about 4 μm to about 7 μm may be used to directly target collagen and/or protein. A 6 μm laser may be used to create scleral vacuoles for uveoscleral outflow enhancements for example.

The system may optionally comprise a first laser with a first wavelength and a second laser with a second wavelength. The system may comprise a first laser with a first wavelength within a range of about 1.4 μm to about 1.6 μm and a second laser with a second wavelength within a range from about 1.9 μm to about 2.3 μm. The system may comprise a first laser with a first wavelength of about 1.47 μm and a second laser with a second wavelength of about 2.1 μm. The 1.47 μm laser for example may be used to treat scleral tissue (or other recalcitrant, thick, dense, or opaque tissue) with deeper penetrance than the 2.1 μm laser. The 2.1 μm laser may for example be used to treat corneal tissue. The 2.1 μm laser may for example be used to treat scleral tissue. In some instances, the sclera may be treated with both the 1.47 μm laser and the 2.01 μm laser at the same or different treatment locations, as the different wavelengths of light may produce different effects within the sclera which may be complimentary in designing a treatment plan. The processor may be configured with instructions to rapidly switch between the 1.47 μm and 2.1 μm lasers during treatment. In some embodiments, the system may comprise a first laser with a first wavelength of about 1.47 μm and a second laser with a second wavelength of about 1.95 μm and the processor may be configured with instructions to switch between the 1.47 μm and 1.95 μm lasers during treatment.

In some embodiments, the transducer array and the processor may be configured to provide a plurality of pulses to a plurality of separate treatment regions separated by a distance. A duty cycle of each of the plurality of separate treatment regions may comprise a duty cycle less than a duty cycle of the transducer array. The plurality of separate regions may comprise a first treatment region receiving a first plurality of pulses and a second treatment region receiving a second plurality of pulses, wherein the treatment alternates between the first plurality of pulses to the first region and the second plurality of pulses to the second region to decrease a duty cycle of each of the plurality of treatment regions relative to the duty cycle of the transducer array in order to decrease treatment time of the first region and the second region. The first treatment region may for example be a first annulus and the second treatment region may be a second annulus.

FIGS. 23A-23C show a handheld probe for applying a juxtacanalicular treatment pattern to the eye. This probe is similar to the probe shown in FIG. 5A for applying a paralimbal treatment pattern, except the light outputs are arranged to deliver the light energy within 2 mm of the limbus of an eye.

Thermomechanical Response of the Eye

In many embodiments, heat is applied to the eye to produce a thermo-mechanical response in a tissue of the eye, such as in the cornea and/or sclera. For example, the cornea and/or sclera can be heated to a range from about 50 to about 70 degrees Centigrade, for example between 60 and 70 degrees Centigrade, to produce shrinkage of the tissue. Tissue may be heated within the range without substantially weakening the tissue. In many embodiments, a portion of the eye can be heated to a temperature within a range of up to about 55 or 60 degrees Centigrade to relax the tissue. Heating of the cornea and/or sclera to a temperature within this range can also produce softening and/or plasticizing (e.g., to approximately 10% of the native strength of the tissue). The cornea and/or sclera can be heated to greater than 80 degrees Centigrade of the eye to produce denaturation of the tissue. The tissue may be weakened by heating to a temperature within a range from about 70 to about 90 degrees Centigrade.

The heating of tissue can be controlled to provide desired amounts of shrinkage or relaxation and combinations thereof. For example, heating collagenous tissue such as scleral tissue to a temperature within a range from about 50 to 70 degrees C. can result in shrinkage of the tissue that can be effective to move tissue to open Schelmm's canal for example. For temperatures in a range from about 60 to 70 degrees C., heating of the tissue can result in shrinkage or relaxation, depending on how long the tissue is heated. For example, heating tissue within a range from 60 to 70 degrees C. for shorter amounts of time can result in tissue shrinkage, while heating tissue for longer amounts of time can result in relaxation. To relax tissue, the tissue temperature can be elevated to a temperature in a range from about 60 degrees C. to about 80 degrees C. For example, heating tissue to about 80 degrees C. for about a millisecond can result in tissue relaxation. For lower temperatures within this 60 to 80 C range, the tissue can be heated for amounts of time longer than 1 ms to provide tissue relaxation.

The treatment locations can be located in one or more of the cornea and sclera, for example slightly below the epithelium and conjunctiva. The treatment region can be located in scleral tissue and can be about 0.25 to about 0.75 mm deep, for example. The corneal treatment region can be from about 0.100 μm to about 400 μm deep, for example. When light energy is used, the depth of tissue with sufficient heating can depend on the wavelengths of light energy. For example, light energy having wavelengths in a range from about 1.9 to 2.1 μm, the 1/e attenuation depth can be in a range from about 200 to 300 μm, for example about 225 to 275 μm. For light energy having wavelength in a range from about 1.3 to 1.6 μm, the 1/e attenuation depth is within a range from about 350 to 450 μm. When combined with the cooling lens as described herein, the profile of tissue heating can result in a peak temperature that is located beneath the exterior surface of the ocular tissue, even though the amount of light energy absorbed near the surface is greater than the amount of light energy absorbed at the tissue location which undergoes the highest amount of temperature increase. The depth of tissue that shrinks or relaxes can have a profile extending to a depth in the tissue.

In some instances, electro-sprayed water droplets may be used in combination with treatment with light energy to induce cavitation in the treated tissue. For example, water and/or heavy-water droplets may be electro-sprayed or mono-dispersed over a scleral treatment region without a corona discharge in ambient air prior to or during treatment of the tissue with light energy. Deposition of the micro-droplets may be electronically controlled and steered toward locations of interest. The droplets may for example comprise highly charged gas-encased water. The droplets may self-assemble due to the high charge carried in the sub-surface scleral volume. When seeded for micro-bubbles under laser irradiation, the droplets may migrate uniformly inside the irradiated tissue in order to create ordered pathways which may have enhanced stability and which may improve fluid outflow in the treated scleral region. Alternatively or in combination, cavitation of the tissue may open tight junctions which may improve permeation and stability without requiring the use of viscosity additives of penetration enhancers as have been previously used in the art. Such droplets may further be configured to carry cavitation seeding agents such as oxygen or carbon dioxide to enhance cavitation beyond that of the droplets alone. The droplets may alternatively or in combination be configured to carry other drugs or medicaments into the scleral tissue as desired by one of ordinary skill in the art.

The combination of light energy and micro-droplets may allow for the generation of scleral vacuoles (i.e. increased scleral porosity) with lower dose irradiation that would be possible with the use of light energy alone, which may be beneficial in at least some instances. Intra-stromal delivery may for example be achieved with 10 kV at 100 nA, which may allow the system to operate as a battery-operated unit. The combination of light energy and micro-droplets may allow for non-thermal cavitation of tissue which may be substantially similar to ultrasonic cavitation in its tissue effects as described herein.

Ultrasound methods and apparatus can be used to heat tissue with similar temperatures and locations as described with reference to laser treatment, in order to provide glaucoma treatment. Other types of energy as described herein can be used similarly to treat glaucoma as will be appreciated by one of ordinary skill in the art. The ultrasonic approaches as described herein can also be used to soften tissue without substantial heating, for example.

The optional use of nanoparticles similar to nanoparticles for enhanced imaging can be used to enhance cavitation in some embodiments. Nanoparticles can be used with ultrasound treatment to reduce the cavitational dosage requirements, for example by a factor of 2×-10×. The nanoparticles may comprise one or more of perfluorocarbon, lipid, albumin, or galactose, for example. Targeted (optionally drug-free) lysis due to microstreaming and micro-fragmentation (<5 μm diameter) can improve micro-circulation and contains region of treatment demarcation with added safety. Treatments can be provided with decreased bleeding and decreased apoptosis, which can be shown with blood brain barrier and myocardial infraction studies, for example. While the nanoparticles can be used for any of the treatments disclosed herein such as glaucoma treatments, the nanoparticles can be beneficial for fractionation and apoptosis of choroidal neovascularization (CNV) and uveal melanomas, for example.

Imaging while Treating

The methods and system disclosed herein can be used in many ways and can be used to image the tissue during treatment. The treatment system may include an imaging apparatus such that the treatment can be combined with imaging with one or more of magnetic resonance (MR) imaging, ultrasound biomicroscopy (UBM), ultrasound (US) imaging, optical coherence tomography (OCT), optical coherence elastography (OCE), or US elastography transducer measurements. The imaging apparatus can be combined with the glaucoma treatment with either simultaneous oblique trans-iridional imaging or on the coaxial therapeutic probe; and diagnostic images that are useful intra-operatively, for visualization as well as for feature/landmark tracking. Rapid real time MR images can be acquired when time-synchronized to treatment energy pulses with weighting motion gradients turned ON for greater cavitational sensitivity. MR/OCT/US guidance can include one or more of pretreatment planning, image-based alignment and siting of the energy source focus, real-time monitoring of treatment energy-tissue interactions, or real-time control of exposure and damage assessment.

The treatment system may comprise an imaging apparatus capable of determining tissue elasticity before, during, or after treatment, or some combination thereof, for example OCE or US elastography transducers. The treatment system may additionally or in combination comprise a mechanism for real-time temperature sensing, for example using an OCT transducer, for real-time monitoring of laser-induced temperature changes or to provide for control of laser exposure to maintain temperature. Motorized diagnostic imaging in sync with treatment patterning can be achieved in these configurations. For example, real-time imaging of treatment tissue may allow for user input to a grid of target regions, which may be larger than the area covered by a single treatment or include multiple areas not in direct contact with each other, for motorized control of multiple treatments over a larger area, allowing the user to avoid manual repositioning which may save time and prevent mistakes.

Imaging may be configured to occur simultaneously with treatment. A processor can be coupled to the ultrasound array and configured with instructions to scan the beam to a plurality of locations and image the tissue during treatment. The system may also comprise a display coupled to the processor that allows the user to see the tissue treated on the display and to plan the treatment. The images shown on the display can be provided in real time and can allow the operator to accurately align the tissue with the treatment and may allow the operator to visualize the treatment area, and other locations away from the treatment area. The imaging of the treatment area can be used to identify the target area on the screen and to program the treatment depth and location in response to the images shown on the display. The imaging can be used to visualize movement of ocular structures during treatment to detect beneficial treatment effects. The processor can be configured with instructions to treat the eye with a first wavelength of ultrasound energy and to image the eye with a second wavelength longer than the first wavelength. The processor may alternatively or in combination be configured with instructions to treat the eye with laser energy and to image the eye with an embedded imaging apparatus, for example an optical coherence tomography (OCT) probe. The processor coupled to the array can be configured with instructions to provide both ultrasound wavelengths from the array. The imaging apparatus may provide additional tissue feedback data in real-time, for example temperature or elasticity.

The processor may be configured with instructions to determine one or more locations of the limbus, and/or one or more locations of Schlemm's canal. In response to the determined location of limbus, for example, one or more locations of Schlemm's canal may be determined. The processor may be configured with instructions to determine a treatment pattern based on the one or more locations of the limbus and/or the one or more locations of Schlemm's canal. The treatment pattern may for example comprise a juxta-canalicular treatment pattern. The processor may be configured to deliver shrinkage energy to the sclera, cornea, or both in order to urge tissue near Schlemm's canal to move towards the treated tissue and dilate Schlemm's canal as described herein. Alternatively or in addition the processor may be configured to deliver shrinkage energy to the sclera to open the iridocorneal angle and/or deepen anterior chamber depth.

Figure 24:
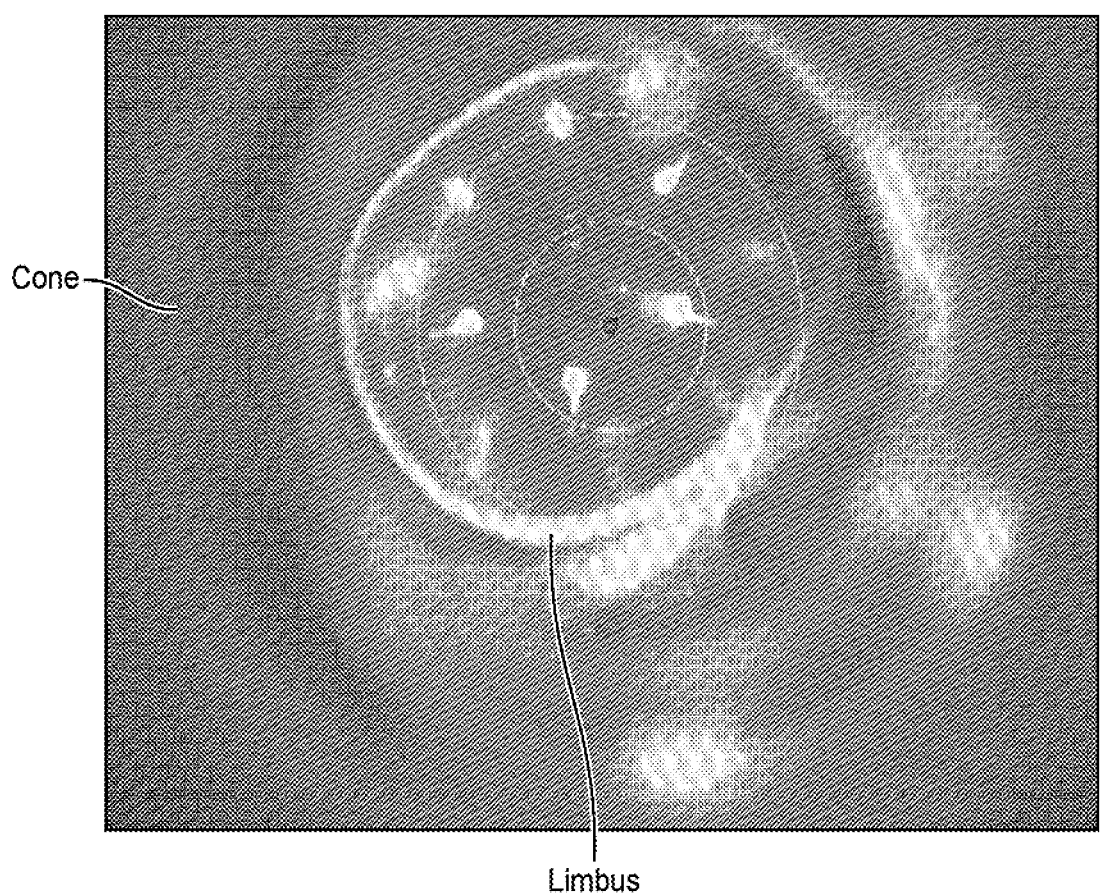
FIG. 24 shows an image of an eye taken by a camera after docking the patient interface and system to the eye, in accordance with embodiments, with an image of the limbus illustrated on the eye.

FIG. 24 shows an image of an ex vivo porcine eye taken with a camera after docking the patient interface and system to the eye. The limbus was clearly visible for use to pattern glaucoma treatment relative to the location of the limbus. Patterning may be selected manually by the user (e.g. medical professional) or the patterns may be determined automatically (or semi-automatically) by the system based on an estimated location of the limbus, Schlemm's canal, or other fiducial of interest. The location of the limbus may be estimated manually by the user. The location of the limbus may for example be "tracked" automatically by the system using a camera and/or other imaging system such as OCT as described herein. The location of the limbus may comprise a complete, annular outline of the limbus or may comprise multiple locations along the limbus which may be used as reference points for determining the shape of the limbus and/or where treatment should occur (i.e. an incomplete outline of the limbus). Treatment may be patterned to include or avoid the limbus as desired by one of ordinary skill in the art.

Glaucoma treatment may be patterned relative to the location of Schlemm's canal. Identification of one or more locations of the limbus as described herein may be used to estimate one or more locations of Schlemm's canal. The limbus may be used as a surrogate for Schlemm's canal as they can be located at measurable or known distances from one another. The location of Schlemm's canal with respect to the limbus may vary systematically with age and/or IOP. For example, Schlemm's canal may be further away from the limbus in younger eyes than in older eyes. Schlemm's canal may be further away from the limbus in patients with increased IOP compared to patients with normal IOP. Such variations may be considered when patterning treatment. For example, treatment may be patterned further out from the limbus in an older patient than in a younger patient to account for the difference in location of Schlemm's canal with reference to the limbus. In some instances, the limbus and Schlemm's canal are roughly the same position radially within the eye and the position of the limbus may be roughly the position of Schlemm's canal.

Figure 25:
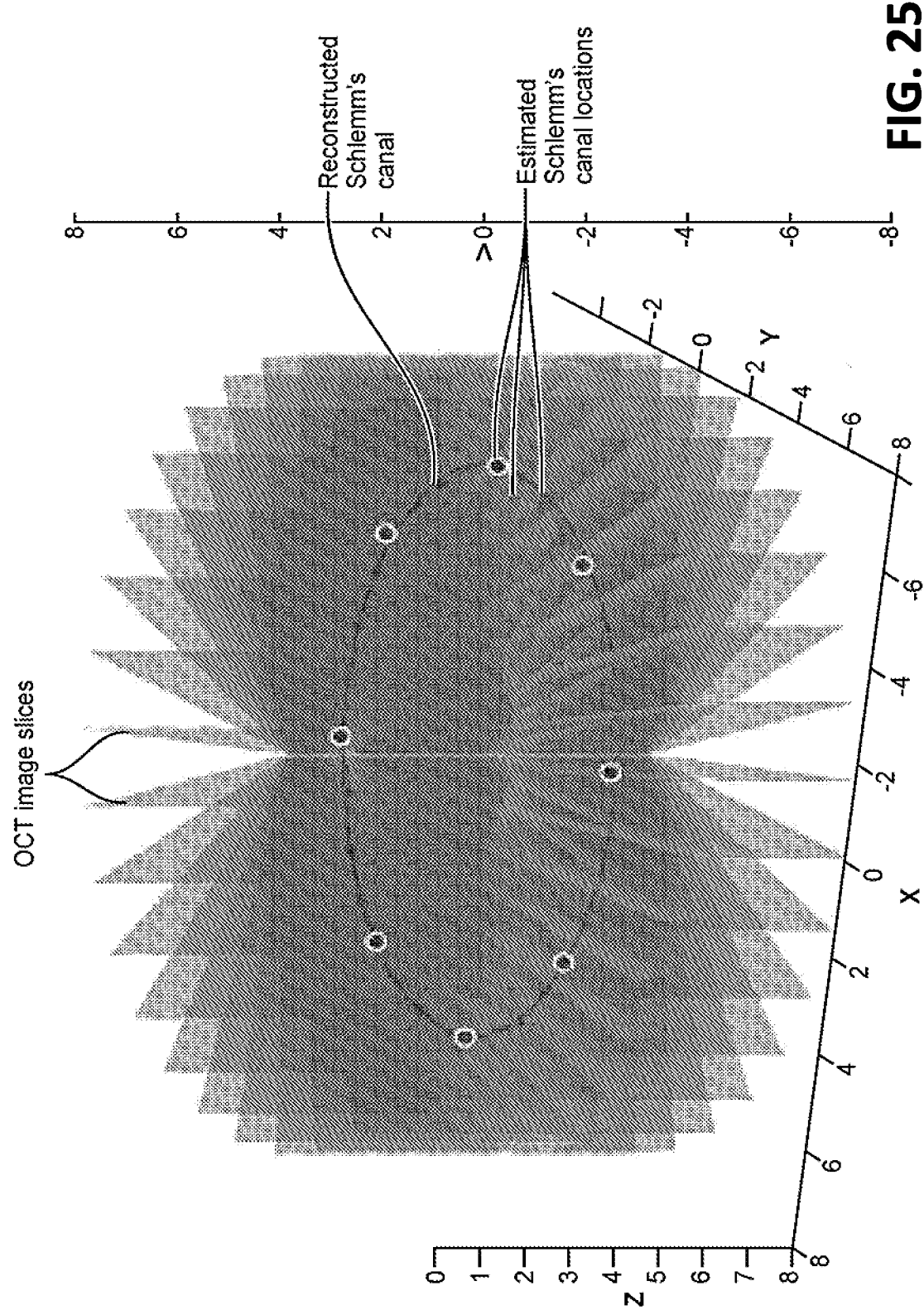
FIG. 25 shows an imaging scheme which may be used to estimate the shape of Schlemm's canal.

Alternatively, or in combination, one or more locations of Schlemm's canal may be estimated from one or more OCT slices. For example, a single OCT image taken through the center of the eye may be used to identify two locations of Schlemm's canal (one on either side of the eye) and the treatment locations/pattern may be determined in response to the two Schlemm's canal locations identified. In some instances, multiple OCT images may be taken at different angles relative to the center of the eye and a plurality of Schlemm's canal locations may be identified and used to estimate the shape of Schlemm's canal. FIG. 25 shows one such imaging scheme which may be used to estimate the shape of Schlemm's canal. Multiple OCT images may be taken across the center of the eye at varying angles and the one or more location of Schlemm's canal may be estimated from each image. The locations (and optionally the images as shown) may then be used to estimate the shape of Schlemm's canal using partial 3-D reconstruction.

Figure 26A:
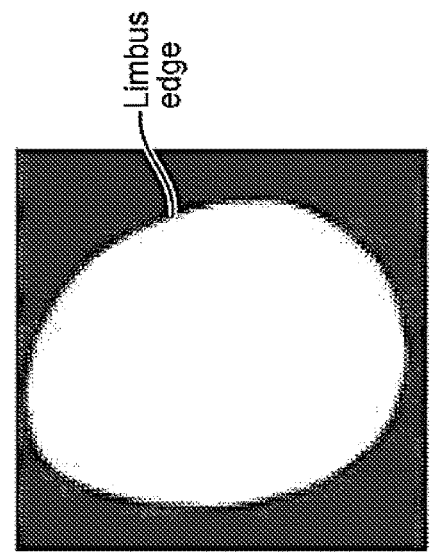
FIGS. 26A-26D show an exemplary process for generating a treatment pattern based on one or more locations of the limbus.

In some instances, the location and/or shape of the Schlemm's canal may be estimated in response to a plurality of limbus locations of the eye. As an example, an image (e.g. an anterior image of the eye) including the limbus may be acquired (e.g. as shown in FIGS. 24 and 26A). The locations of the limbus, or plurality of limbus locations may be determined, based on the image of the eye. For example, by detecting changes in intensity in the anterior image (e.g. across the image, over a series of images, etc), the location of a plurality of limbus locations may be determined. In some instances, one or more processors may be utilized to analyze the image to determine the limbus locations. Based on the plurality of limbus locations, a plurality of Schlemm's Canal locations may be estimated substantially as described throughout.

Figure 26B:
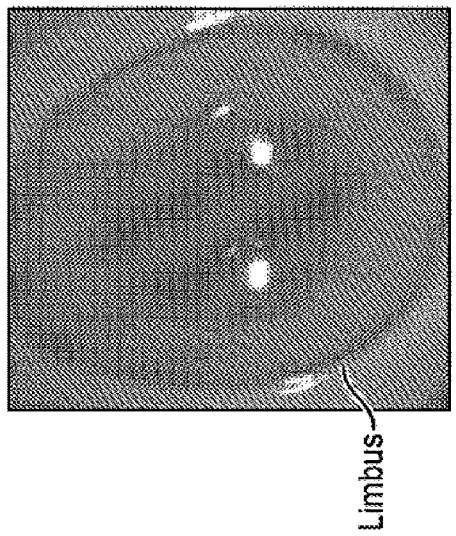
Figure 26C:
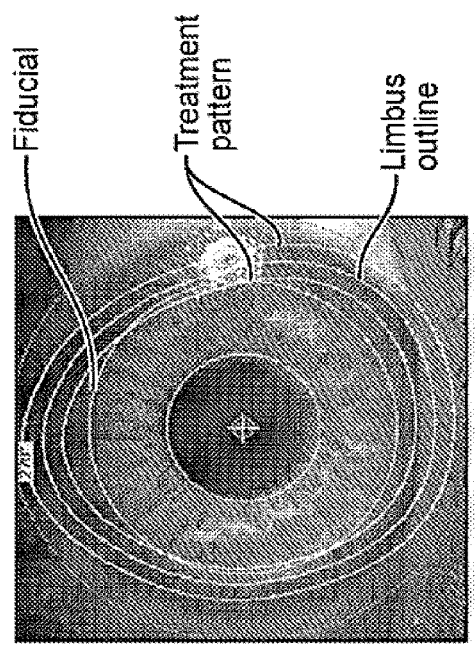

FIGS. 26A-26D show an example of a process for generating a treatment pattern based on one or more locations of the limbus. FIG. 26A shows an anterior image of an eye taken with a front camera of a CASIA2 OCT system. The anterior image of the eye may be transferred to the processor for detection of the limbus edge. FIG. 26B shows the image after processing to determine the boundaries (edges) of the limbus. The portion of the eye within the limbus has been colored white while the portion of the eye outside the limbus has been colored black. This black and white image may then be used to generate X-Y coordinates of the edge of the limbus. The processor may then use the X-Y coordinates to generate an outline of the limbus which may be overlaid onto a real-time image of the eye shown on the display as shown in FIG. 26C. The X-Y coordinates may be registered with the real-time image of the eye such that the limbus shown on the display and the X-Y coordinate generated limbus outline are co-aligned.

Figure 26D:
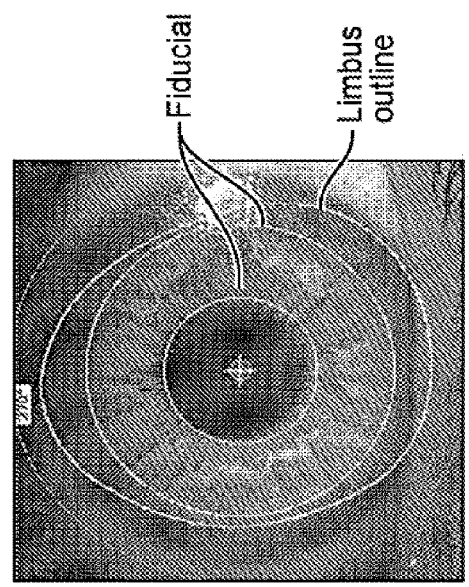

The image may also display fiducials with reference to the center of the eye to aid in centration of treatment, for example circles displayed radially outward every 5 mm from the center of the eye. The processor may further use the X-Y coordinates and/or the generated outline of the limbus to determine a treatment pattern, for example a series of juxtacanalicular treatments patterned radially inward and/or outward of and shaped like the limbus as shown in FIG. 26D. Note that the images of the eye shown in FIGS. 26C-26D, over which an outline of the limbus and/or treatment patterns is shown, are images of a representative eye for visualization purposes and not real-time images of the eye used to generate the limbus outline/treatment nomogram and therefore the outline and the limbus on the image do not co-align in these examples. It will be understood by one of ordinary skill in the art that during use the limbus outline and/or treatment patterns may be registered to one another (i.e. co-aligned) such that the outline and real-time location of the limbus overlap.

Figure 27:
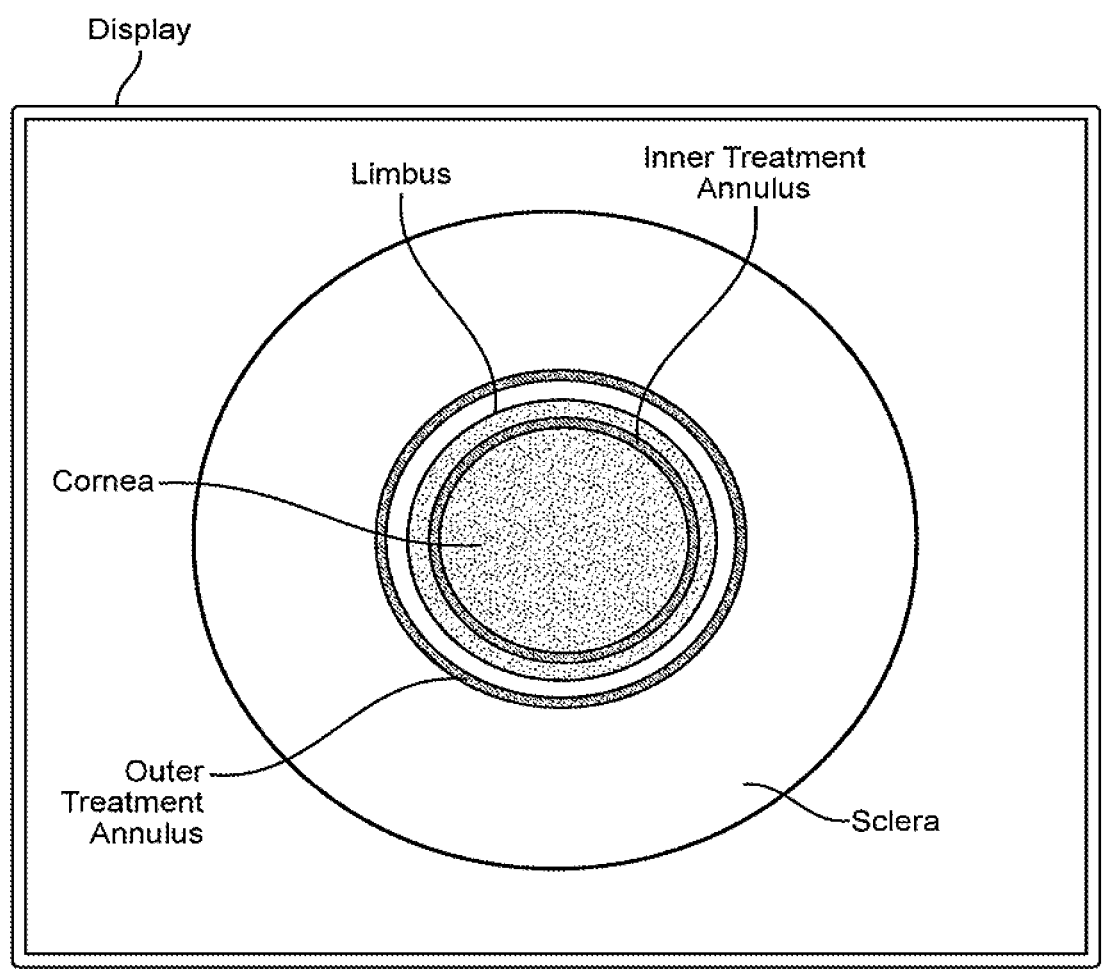
FIG. 27 shows a schematic of a display for use in directing treatment to targeted treatment zones, in accordance with embodiments.

FIG. 27 shows a schematic of a display for use in directing treatment to targeted treatment zones (also referred to herein as targeted treatment regions). The glaucoma system described herein may allow for pre-treatment planning and/or treatment of a tissue in an image-guided manner Treatment locations and patterns may for example be input by a user in response to an image shown on the display. Alternatively or in combination, the treatment locations of patterns may be determined in response to an image of the eye or a plurality of OCT images of the eye, for example in response to an estimated location of Schlemm's canal or the limbus as described herein. The image shown on the display may be obtained pre-operatively or in real-time prior to or during treatment. The image shown on the display may comprise a real-time anterior image of the eye captured by an operating microscope or camera coupled to the system. The image shown on the display may comprise one or more OCT image slices of the eye. Targeted treatment pattern(s) and/or location(s) may be selected by a user or operator in response to the image displayed. The user may input the desired treatment patterns to provide the processor with instructions to scan and/or pulse the energy beam to the targeted treatment locations. The user may for example input the desired treatment patterns using a touch-screen to select the target zones directly on the displayed image or by using a joystick or mouse to point a cursor at the target locations. Alternatively, or in combination, the processor may be configured with instructions to generate one or more treatment locations and/or one or more treatment patterns based on an image of the eye.

For example, the glaucoma treatment system may be used to target juxtacanalicular treatment to straddle Schlemm's canal (FIG. 27) or paralimbal treatment on the sclera more than 2 mm from the limbus (FIG. 3A). Real-time anterior image(s) and/or OCT image slices of the eye may be acquired and displayed for the user (for example a doctor) to view. In some instances, the treatment may be located at a predetermined radial distance relative to the center of the eye or the center of the cornea. Alternatively, treatment may be located with respect to one or more fiducial markers such as the limbus, the anterior chamber width, Schlemm's canal, the iris, the trabecular meshwork, or any combination thereof. For example, a fiducial such as the limbus or Schlemm's canal may be identified by the user and the treatment may be patterned by the user directly onto the image of the eye using a touch screen in response to the location of the limbus. Alternatively, the limbus or Schlemm's canal may be selected using a touch screen and the treatment may pattern may be generated by the processor in response to the location of the limbus. The processor may then direct the energy source to deliver treatment energy to the treatment locations, for example an inner treatment annulus and an outer treatment annulus straddling the limbus/Schlemm's canal. In some instances, the processor may be configured with instructions to direct energy into the eye with an annular pattern. The annular pattern may in some instances comprise an inner dimension located radially inward from the Schlemm's canal and an outer dimension radially outward from the Schlemm's canal. In other instances, the annular pattern is only radially outward from Schlemm's Canal (for example in the paralimbal treatment to open the iridocorneal angle).

The processor may be configured with instructions to receive user inputs to define the plurality of targeted tissue locations on the image of the eye prior to treatment with the treatment energy. The processor may be configured with instructions to register the plurality of target tissue locations defined prior to treatment with a real time image of the eye acquired during the treatment and to show the target tissue locations of the eye in registration with the real time image of the eye. The imaging system (e.g. OCT, UBM, US, etc.) may be aligned with the energy source, for example a laser array. The processor may comprise instructions to direct the treatment energy to the plurality of treatment locations in response to registration of the real time image of the eye with the image of the eye in response to movement of the eye.

The processor may be configured to scan the energy beam to a plurality of locations. A laser energy source may be coupled to a scanner and configured to scan a laser beam to the plurality of locations. The system may optionally further comprise an actuator coupled to the laser to scan the laser beam to the plurality of locations. The processor may be configured with instructions to generate a laser beam comprising a plurality of pulses. Each pulse of the plurality of pulses may be separated from a subsequent pulse of the plurality of pulses by a time within a range from about 1 microsecond to about 1000 microseconds to provide a duty cycle of no more than about 5 percent (%) to a target tissue region.

The system may for example comprise a translation stage, an X-Y translation stage, an actuator, a galvanometer and a gimbal. Alternatively or in combination, the system may comprise a handheld probe.

The treated pattern may not produce an optically visible artifact to a patient viewing with the eye for a period of time post-treatment within a range from about one week post-treatment to about one month post treatment. In some instances, the processor may be configured with instructions to estimate a plurality of locations of Schlemm's canal of the eye. Optionally, the processor may be configured to generate a plurality of treatment locations for the eye in response to the plurality of locations of Schlemm's canal of the eye. The plurality of treatment location may in some instances be located within 2 mm radially of the Schlemm's canal. In other instances the treatment locations are also or only located more than 2 mm radially outward of Schlemm's Canal. The plurality of treatment locations may be located radially inward from the Schlemm's canal toward an optical axis of the eye or radially outward from the Schlemm's away from the optical axis of the eye as measured along an exterior surface of the eye.

The processor may be further configured with instructions to deliver energy to the treatment locations. The processor may in some instances be further configured with instructions to shrink collagenous tissue in the sclera, for example near Schlemm's canal or collector channels, or more than 2 mm radially outward from Schlemm's Canal. In other instances, the processor may be configured with instructions to treat scleral tissue of the eye to provide vacuoles in the sclera and increase outflow through the sclera to lower intraocular pressure. Optionally, the processor may be configured with instructions to treat the eye to increase an angle of the eye, dilating and stretching one or more of the trabecular meshwork or Schlemm's canal, increasing porosity of the sclera and dilating the perilimibic sclera.

In some instances, the processor may be configured with instructions to treat the eye with a plurality of patterns. For example, the processor may be configured with instructions to treat the eye with a first pattern and a second pattern. In some instances, the first pattern may be utilized to treat glaucoma of the eye and a second pattern may be utilized to treat a refractive error of the eye. Alternatively, the first and second patterns are both used to treat glaucoma, but are directed to different anatomic locations (juxtacanalicular, paralimbal, or collector channels). The first and second patterns may be as have been substantially described throughout.

The processor may be configured with instructions to apply a total amount of energy substantially as described throughout. For example, the processor may be configured with instructions to apply a total energy within a range from about 4 J to about 90 J. Optionally, the energy directed to the eye may have a total energy within a range from about 5 J to about 50 J. Optionally, the energy directed to the eye may have a total energy equal to or less than about 1 J, 2 J, 5 J, 10 J, 15 J, 20 J, 25 J, 30 J, 35 J, 40 J, 45 J, 50 J, 60 J, 70 J, 80 J, 90 J, 100 J, 120 J, or 150 J.

Graphical User Interface

FIGS. 28-38 show optional, exemplary graphical user interfaces which may be displayed on the display to the user of the glaucoma treatment system described herein. The graphical user interface (GUI) may be configured to allow the user to adjust the treatment parameters and provide instructions to the processor as described herein.

The GUI may provide the user with the ability to generate treatment patterns and/or adjust pre-generated treatment patterns (such as juxtucanalicular or paralimbal treatment patterns generated based on the outline of the limbus as described herein). Pre-generated treatment patterns may be overlaid onto a real-time image of the eye as described herein. In some instances, for example, it may be desirable to open Schlemm's canal while avoiding exerting tension on the zonules, and a juxtacanalicular treatment pattern may be displayed to the user. In other instances, it may be desirable to deepen the anterior chamber and increase the iridocorneal angle by exerting tension on the zonules and a paralimbal pattern may be displayed to the user. The user may decide to keep or adjust the treatment pattern generated. In some instances, the user may combine treatment patterns for multiple indications—for example by adding a pars plana treatment pattern to generate scleral vacuoles, a collector channel pattern, or a paralimbal pattern to a juxtacanalicular treatment pattern. Any of the treatment patterns described herein may be combined as desired by one of ordinary skill in the art.

Parameters which may be adjusted by the GUI include rotation of the treatment pattern and X-Y centration of the treatment pattern. In many instances, X-Y centration of the treatment pattern occurs automatically upon registration of the real-time image and the X-Y coordinates generated from a pre-operative anterior image of the eye, such as an OCT image of the eye, based on the location of one or more fiducials. Additionally, the speed, pulse frequency, power, beam diameter, and number of repetitions performed by the laser may be adjusted by the user based on the desired treatment results. The spacing of treatment arcs, location of treatment arcs, diameter of treatment arcs, and/or the shape of the treatment arcs may be adjusted by the user in order to generate the desired treatment pattern. In some instances, a treatment arc may be a 360-degree treatment. In some instances, a treatment arc may be less than 360 degrees. The processor may be configured to compute and display to the user the amount of time of treatment, the amount of energy to be deposited, the power used by the laser, the amount of time elapsed, the amount of time left in treatment, and/or the temperature of the cooling structure (e.g. contact lens) during treatment in order to monitor the progress and/or adjust the treatment parameters in real-time.

Figure 28A:
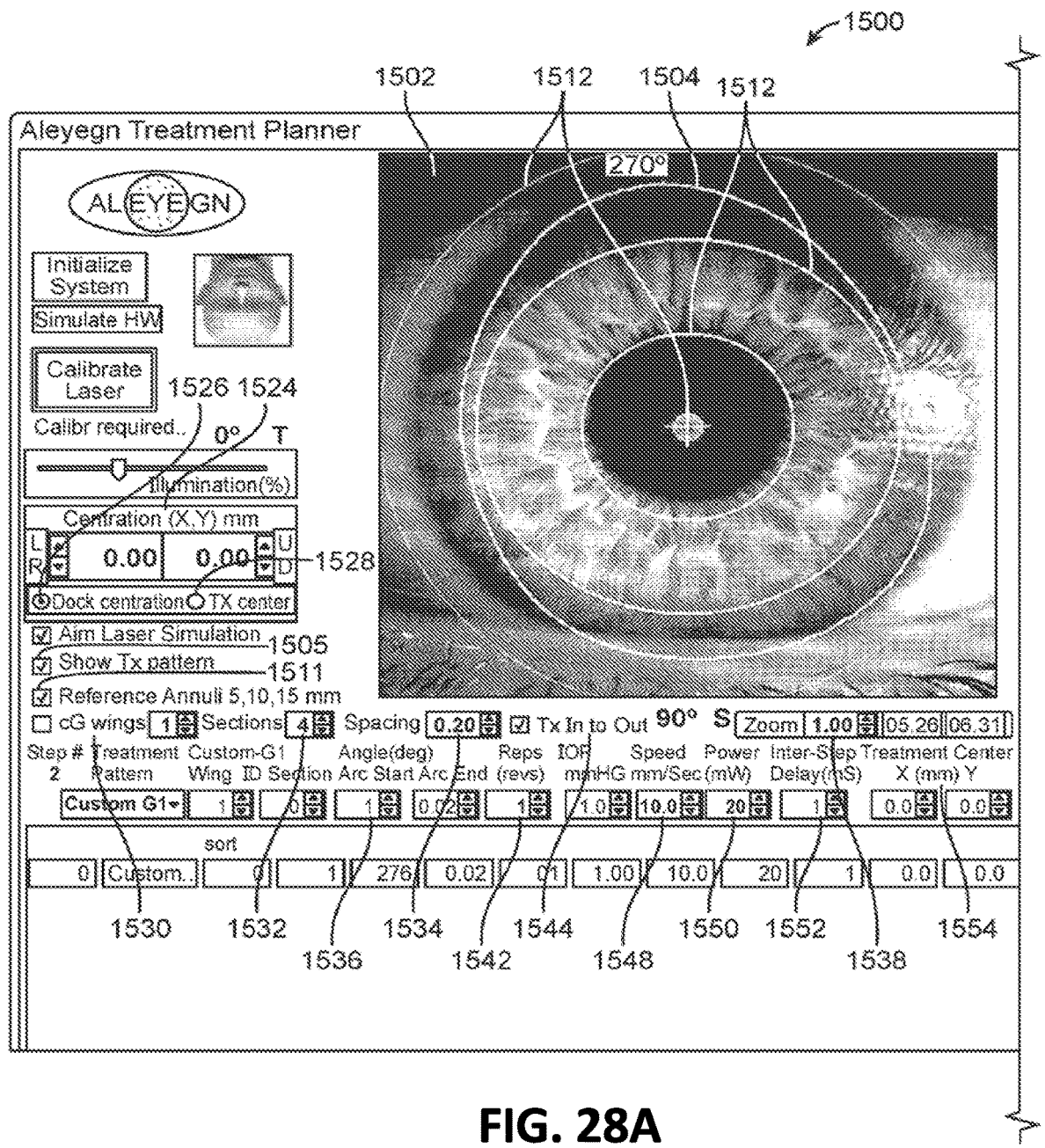
FIGS. 28-35 show graphical user interfaces of a treatment system, in accordance with embodiments.
Figure 28B:
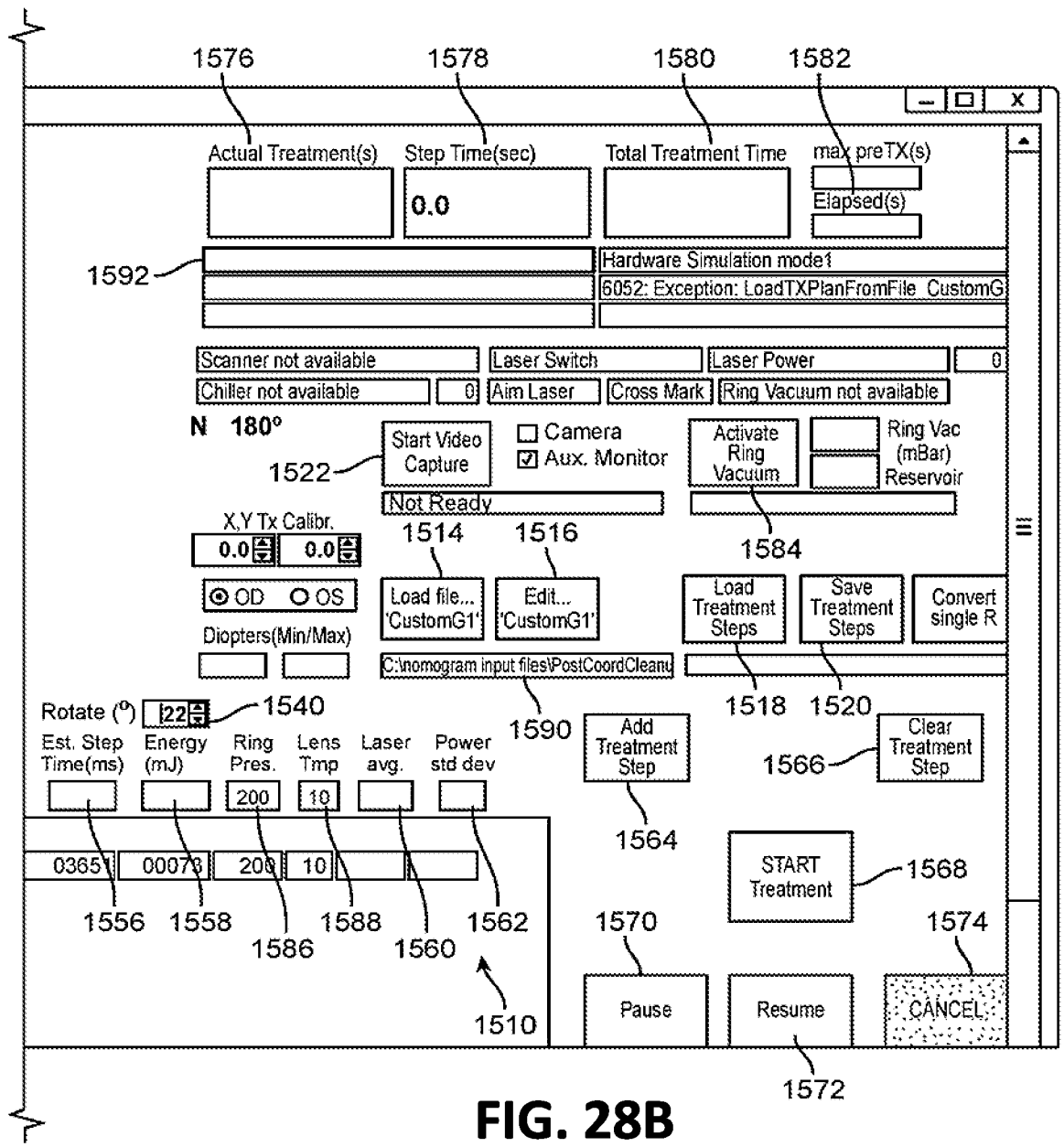
Figure 29A:
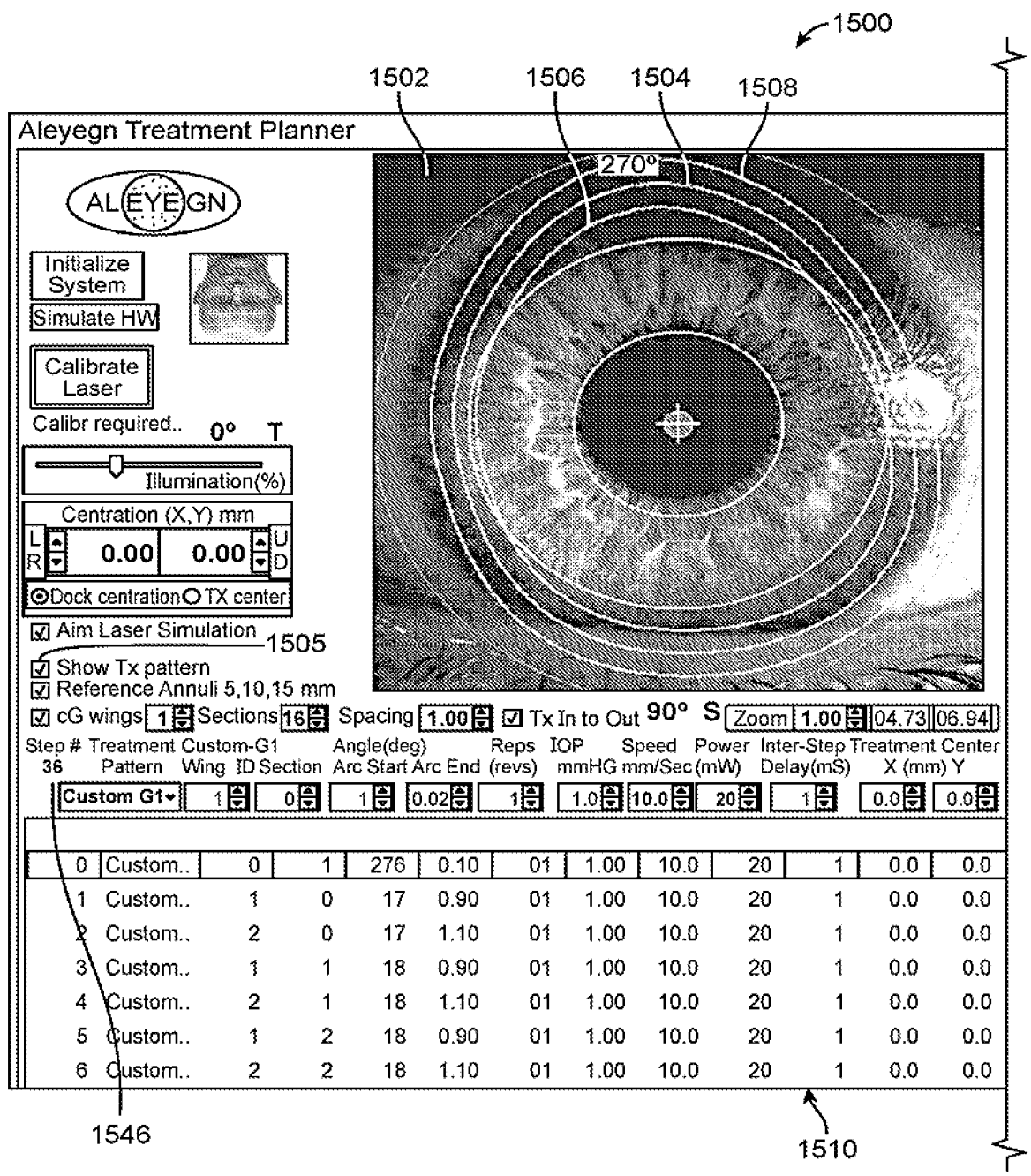
Figure 29B:
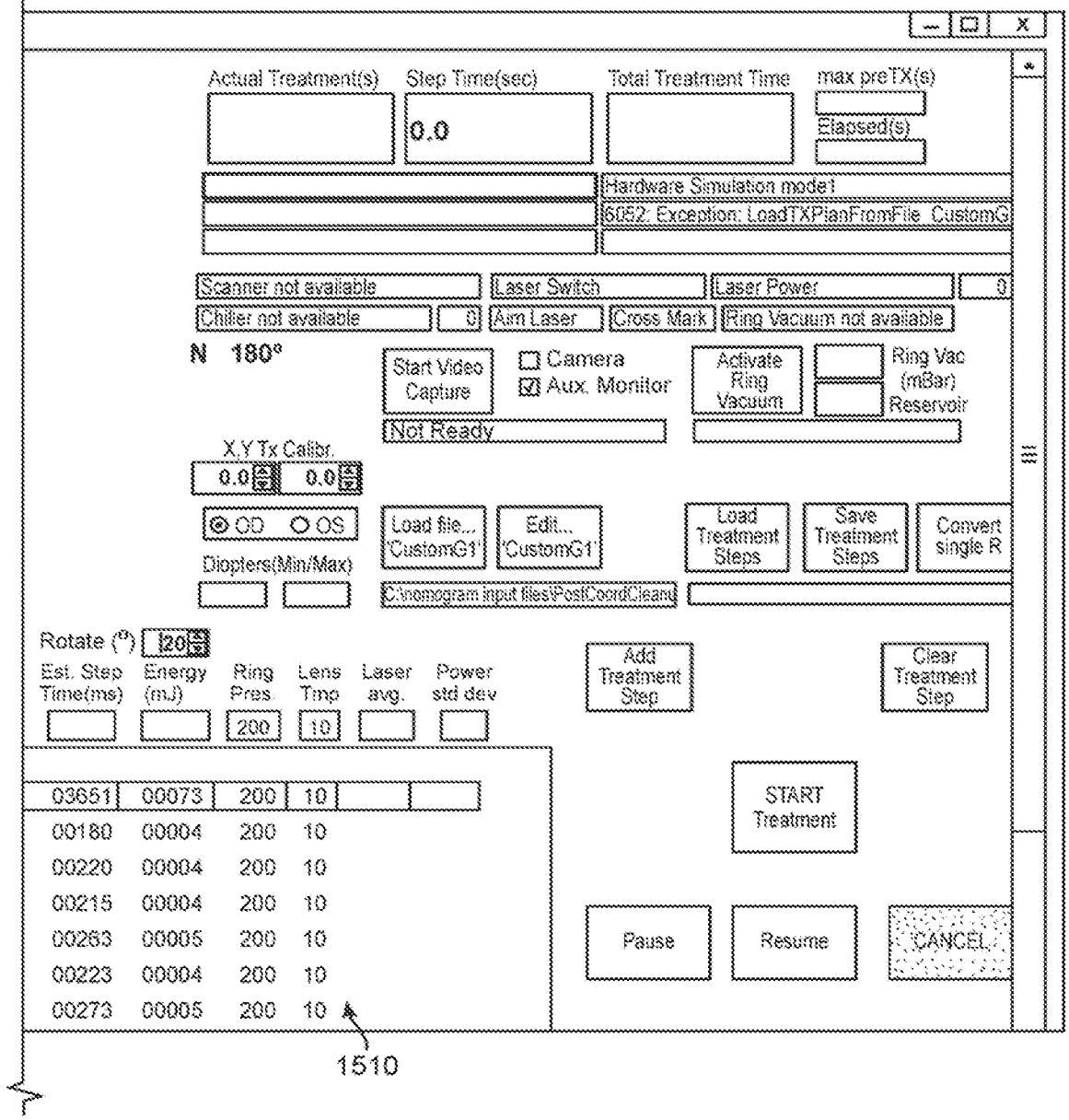
Figure 30A:
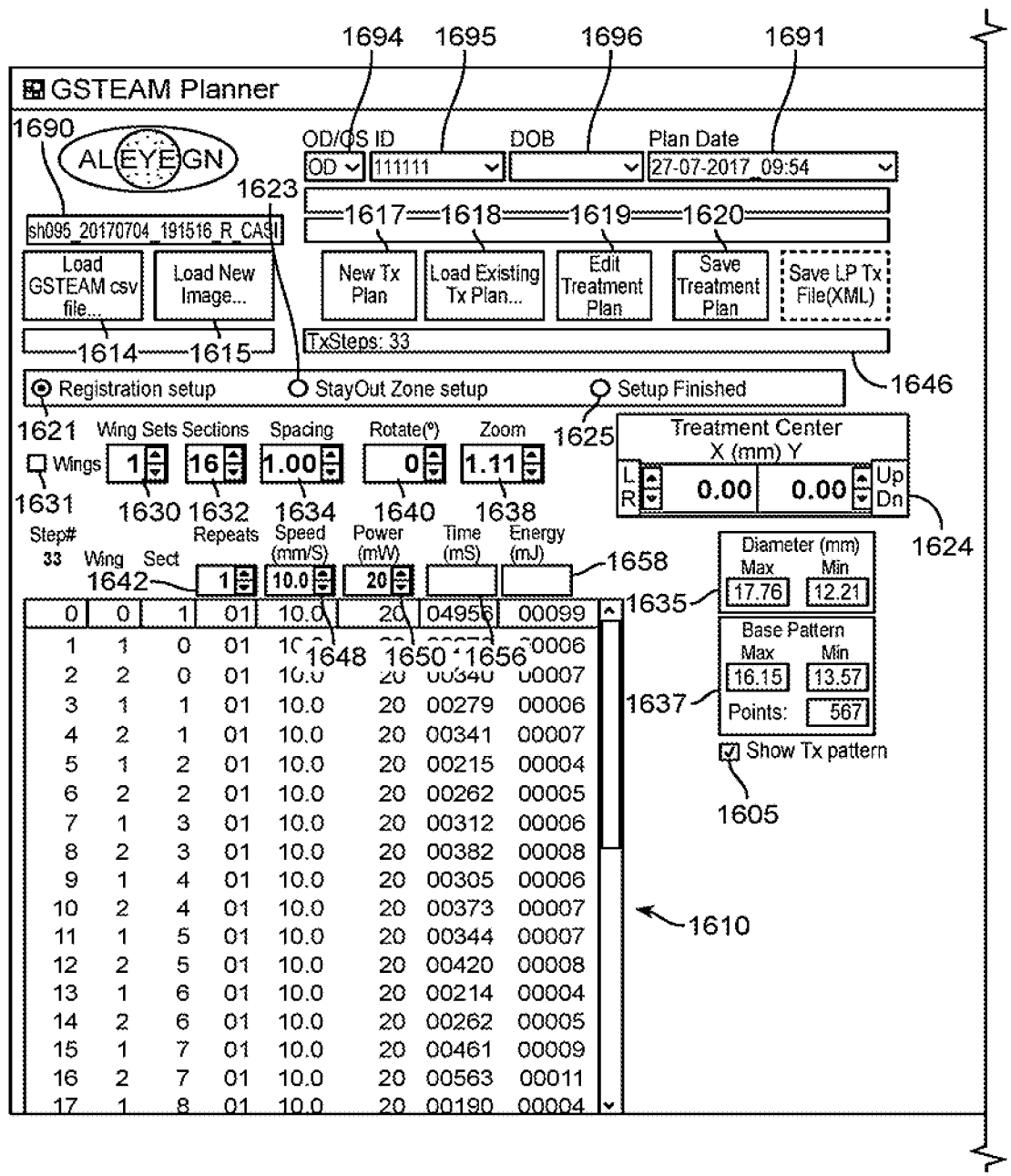
Figure 30B:
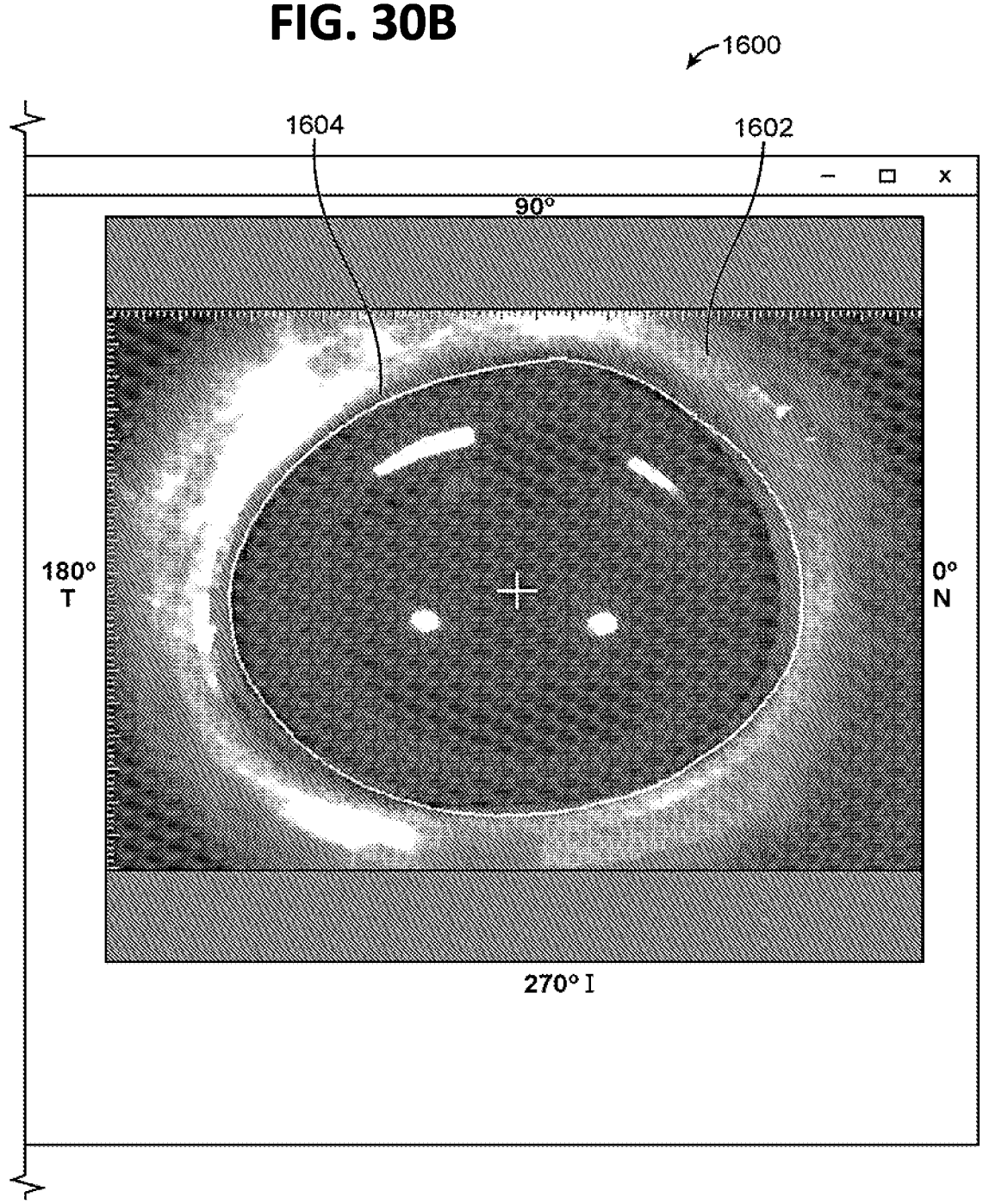

FIGS. 28 and 29 show a graphical user interface 1500 which may be displayed on the display to the user of the treatment system described herein. The graphical user interface may (GUI) 1500 be configured to allow the user to adjust the treatment parameters and provide instructions to the processor. The GUI 1500 may be configured to allow the user to plan the treatment (e.g. set up the treatment pattern, parameters, etc.) prior to treatment. The GUI 1500 may display an anterior image of the eye 1502 to the user prior to, during, or after treatment as described herein. For example, as shown in FIG. 28A, the anterior image of the eye 1502 may be displayed with an overlaid outline of the limbus 1504 generated as described herein. In some instances, it may also be desirable to display the treatment location 1506, 1508 on the anterior image of the eye 1504 as shown in FIG. 29A. In some instances, it may be desirable to display reference 1512 annuli to the user, for example concentric circles at 1 mm, 5 mm, 10 mm, and 15 mm from the center. Such overlays 1504, 1506, 1508, 1512 may be configured to remain on the real-time anterior image of the eye 1502 displayed during treatment so that the user may monitor treatment progress and accuracy.

In some instances, it may be desirable to remove the one or more of the overlays 1504, 1506, 1508, 1512 when treatment begins such that treatment may be monitored without being obscured by the overlay. One or more of the overlays may be removed manually prior to starting treatment. Alternatively, or in combination, one or more of the overlays may be manually chosen to be removed when the start treatment button 1568 is selected. Alternatively, or in combination, one or more of the overlays 1504, 1506, 1508, 1512 may automatically be removed when the start treatment button 1568 is pushed to begin treatment of the eye. The anterior image of the eye 1502 may for example be a static image or a video of the eye. The anterior image of the eye 1502 may for example be a three-dimensional image of the eye.

In use, as an example, a user may upload an anterior image of the eye 1502 to the GUI 1500 or start the camera to generate an anterior image of the eye 1502 (e.g. a real-time video stream or static two dimensional or three-dimensional image of the eye of a patient coupled to the system with a patient interface as described herein) using the start video capture button 1522. For example, the user may push the start video capture button 1522 to begin real-time video monitoring of the docked patient eye. The user may then use the GUI to generate a treatment pattern based on the video of the docked patient eye. Alternatively, or in combination, the user may push the start video capture button 1522 to start the video camera then push it again to stop the camera and leave a static image of the patient's eye displayed for the user to work from. The GUI may be used to activate the vacuum on the patient interface ring using the activate ring vacuum 1584 when the patient has been docked to the patient interface.

The anterior image of the eye 1502 may be loaded with a fiducial marker like the limbus outline 1504 described already drawn on it. Alternatively, or in combination, the limbus outline 1504 may be loaded separately of the anterior image of the eye 1502 using the load file button 1514. The x-y coordinates used to generate the limbus outline 1504 may be generated from the anterior image of the eye 1502 using the process described in FIG. 22 for example. In some instances, the user may want to update or adjust the limbus outline 1504 previously generated, for example to adjust centration, size, etc., and may make adjustments using the edit button 1516. Pushing the edit button 1516 may cause the parameter adjustment buttons to modify the limbus outline 1504 instead of the treatment pattern. The name 1590 of the file which contains the limbus outline 1504 may be displayed to the user by the GUI 1500. Alternatively, or in combination, the user may not upload a limbus outline 1504 and may manually pattern the treatment based on a visual inspection of the location of the limbus. In some instances, the user may choose to apply reference annuli 1512 to the anterior image of the eye 1502 using the reference annuli 5, 10, 15 mm button 1511.

After the image 1502 has been displayed with the limbus outline 1504 (if desired) and/or reference annuli 1512, the user may then begin planning the treatment. Previously generated treatment steps may be uploaded using the load treatment step button 1518. Treatment plans generated for future treatments may be saved using the save treatment steps button 1520. While a juxtacanalicular treatment pattern is shown in FIG. 29, it will be understood by one of ordinary skill in the art that any of the treatment patterns and parameters described herein may be planned for using the GUI.

In the case of juxtacanalicular treatment, a new treatment plan may include at least one limbus-shaped inner annulus 1506 positioned radially inward of the limbus outline 1504 and at least one limbus-shaped outer annulus 1508 positioned radially outward of the limbus outline 1504. The user may press the show treatment ("Tx") pattern button 1505 to display/remove the treatment annuli 1506, 1508 on the anterior image of the eye 1502 as desired. The annuli 1506, 1508 may be generated using cG wings button and input field 1530. The button 1530 may be used to apply the wings (i.e. a pair of inner and outer annuli) 1506, 1508 while the input field 1530 may be used to adjust the number of wing pairs 1506, 1508. While only a single inner annulus 1506 and a single outer annulus 1508 are shown, it will be understood by one of ordinary skill in the art that additional annuli may be added to the treatment plan as described herein by increasing the number of wing sets in the GUI. For example, an annulus more than 2 mm outward from the limbus outline may be patterned for a paralimbal treatment pattern using similar controls.

The spacing/step size between annuli (in mm) may be adjusted using the spacing input field 1534. When no reference fiducial like the limbus outline 1504 is used, or when treatment is patterned without reference to the limbus, the cG wings button 1530 (or another button not shown) may be used to pattern treatment annuli on the eye, for example at a selected distance from the center of the eye.

The rotation of the treatment annuli may be adjusted using the rotate input field 1540. The angle of rotation may be configured to be consistent with conventional reference angles used by a physician when looking at the eye through an operating microscope, as will be understood to one of ordinary skill in the art. The temporal ("T") direction may be at 0°, the nasal ("N") direction may be 180°, the superior ("S") direction may be at 90°, and the inferior ("I") direction may be at 270° (shown here oriented towards the top of the display).

The center of the treatment pattern may be adjusted by changing the X and Y coordinates in the Centration (X,Y) mm input field 1524 when the Tx center button 1528 is selected. The center of the reference annuli 1512 may be adjusted by changing the X and Y coordinates in the Centration (X,Y) mm input field 1524 when the dock centration button 1526 is selected. Centration of the reference annuli 1512 may occur automatically or may be done by the user manually as described herein.

The user may select the order of treatment of the annuli using the GUI. For example, the user may select the Tx in to out button 1544 may be selected in order to include instructions to the processor that the annuli are to be treated in order from the innermost annulus 1506 to the outermost annulus 1508. Alternatively, or in combination, the user may use the GUI to direct treatment to occur in a "mark and jump" pattern between treatment annuli, to occur with alternating rings being treated to generate a suspension effect, or to occur with another pattern as described herein or otherwise desired by one of ordinary skill in the art.

The size of the treatment annuli 1506, 1508 may be adjusted using the zoom input field 1538. The treatment annuli 1506, 1508 may be made up of one or more treatment arcs. For example, the annuli 1506, 1508 may be each comprise 4 treatment arcs such that the treatment for each annulus 1506, 1508 is broken up into 4 pieces (e.g. 4 quarters of a circle for example), each piece being a "step" in the plan. The number of sections/arcs may be selected by the user using the sections input field 1532.

The user may adjust the amount of time (i.e. the delay) between steps using the inter-step delay (ms) input field 1552. In some instances it may be beneficial to incorporate a delay between treatment steps, for example to avoid overheating of the tissue when overlapping treatment patterns are used or to account for the time necessary to switch between laser wavelengths when multiple wavelengths of light are used for treatment as described herein.

The user may select the number of times for each annulus to be treated (e.g. the number of full revolutions or repetitions along the annulus) using the reps (revs) input field 1542.

The user may adjust the speed of the laser using the speed mm/sec input field 1548. The user may adjust the power of the laser using the power (mW) input field 1550.

Once the displayed treatment pattern and treatment parameters have been planned by the user, the user may press the add treatment step button 1564 to display the calculated treatment steps in the treatment step menu 1510. The number of steps 1546 may be displayed. Additional steps may be added by generating new patterns/parameters and selecting the add treatment step button 1564 to add the next set of treatment steps to the menu 1510. The clear treatment steps button 1566 may be used to clear treatment steps from the menu 1510, for example by clearing highlighted (or otherwise indicated) treatment steps selected by a user.

The treatment step menu 1510 may display a variety of information about each step of treatment based on the treatment parameters and patterns selected by the user during treatment planning. For example, information about which wing and which are on said wing is being treated may be displayed in columns in the menu 1510. The start and end angles of the treatment arc may be displayed in columns 1536. The user-selected repetition number 1542, the selected scan speed 1548, the selected laser power 1550, the selected inter-step delay 1552, and the treatment center 1554 may also be displayed in columns Additional information may be calculated based on the treatment planned. Such information may be calculated/generated once the add treatment step button 1564 is pressed and displayed by the GUI. Calculated and displayed information may include an estimate of the time to complete each step (in ms) 1556 and/or the amount of energy (in mJ) 1558 delivered in each step. The GUI may also be configured to display the pressure of the patient interface ring 1586 and/or the temperature of the cooling structure (e.g. cooled contact lens) in contact with the patient's eye as described herein.

Treatment may begin when the user selects the START treatment button 1548. The user may also use the GUI to pause treatment with the pause button 1570, resume treatment with the resume treatment button 1572, and cancel treatment with the cancel treatment button 1574. The system may treat the eye until it finishes the final treatment step, or until the pause or cancel buttons 1570, 1574 are pressed, at which point the system may automatically stop the laser and return full control to the GUI 1500.

While treatment is underway, a progress bar 1592 may be displayed to show the user how far along treatment is. Alternatively, or in combination, the amount of time elapsed for each step 1576, the amount of time elapsed in total 1582, and/or the estimated step treatment time remaining 1578 may be displayed. Once finished, the total treatment time field 1580 may display the total amount of time it took to complete the planned treatment. After each step, or after completing the treatment, the average laser power delivered per step 1560 and the standard deviation 1562 may be displayed in the menu 1510.

Not all of the elements in FIGS. 28-29 are labeled in order to make the illustration less cluttered and easier to see. While the GUI shown is configured to be used with a laser system, it will be understood by one of ordinary skill in the art that the GUI may be modified to be used with other energy sources or treatment systems as described herein.

FIGS. 28-35 show another GUI 1600 which may be displayed on the display to the user of the system described herein.

Figure 31A:
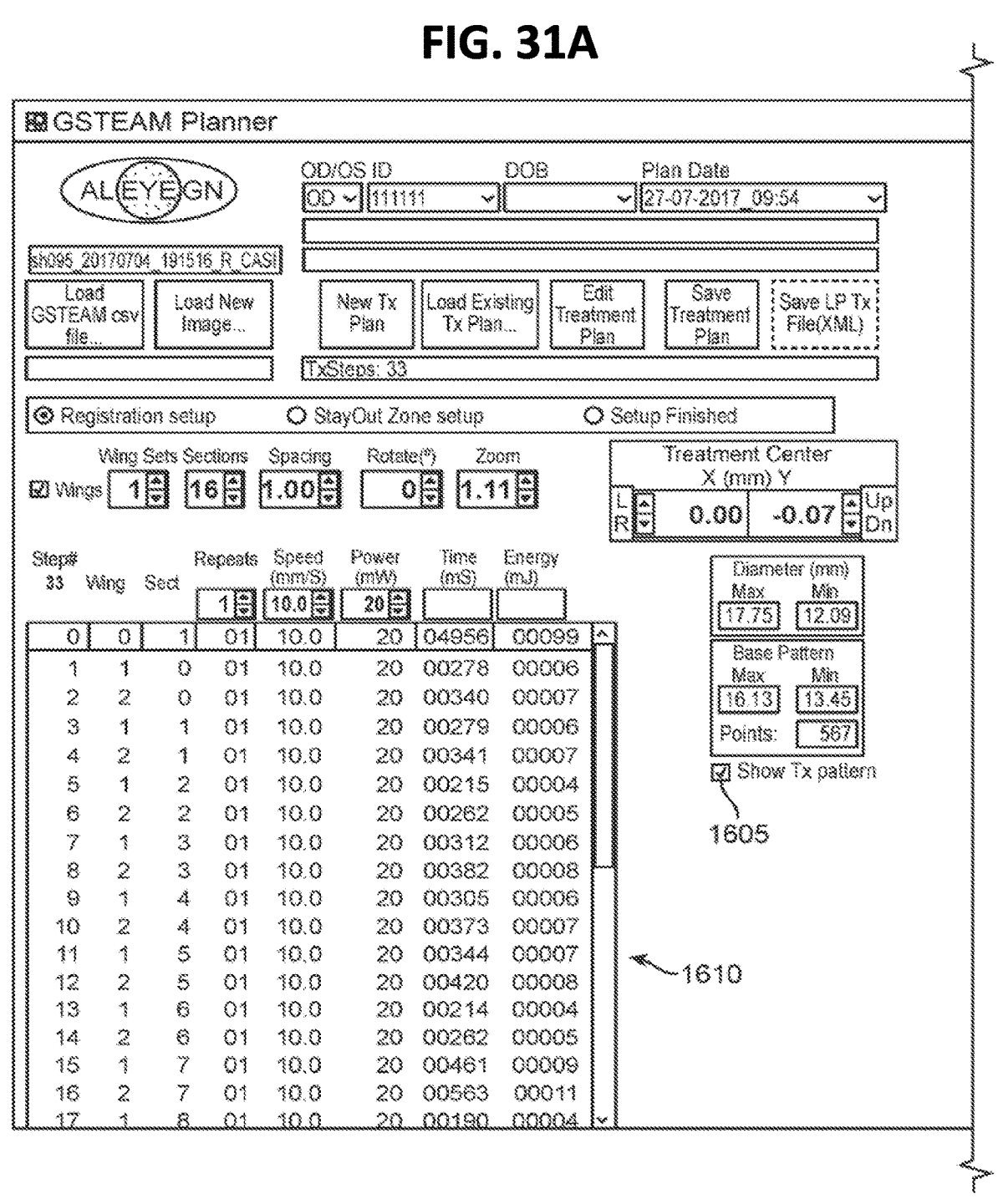
Figure 31B:
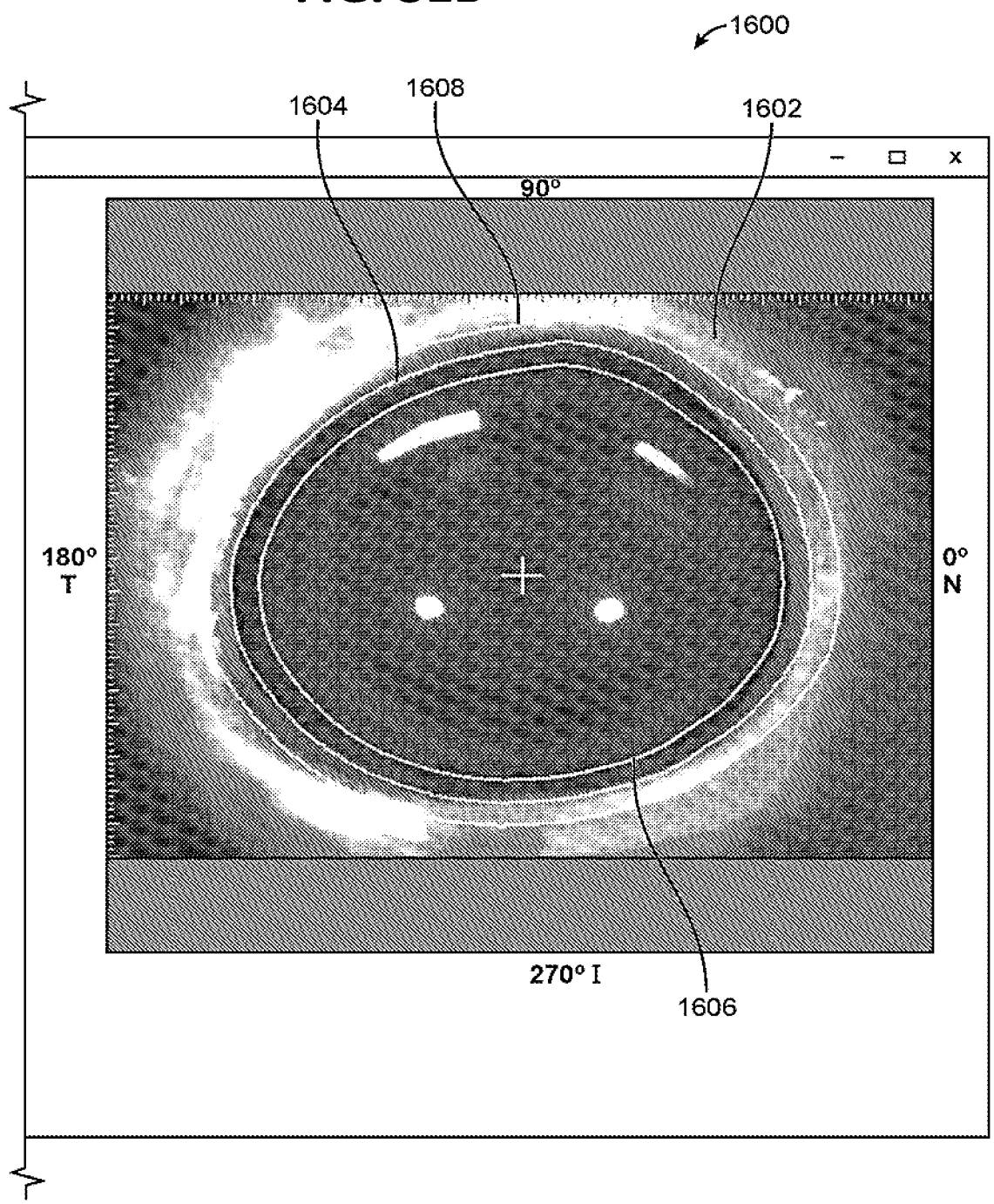

FIGS. 28A and 28B show a screen capture of the GUI 1600 on the registration setup page with an anterior image of the eye 1602 uploaded and displayed to the user with a limbus outline 1604 displayed thereon and generated as described herein FIGS. 31A and 31B show a screen capture of the GUI 1600 on the registration setup page with two treatment annuli 1606, 1608 displayed on either side of the limbus outline 1604 overlaying the anterior image of the eye 1602.

FIGS. 32A and 32B show a screen capture of the GUI 1600 on the stay-out zone setup page with a section disabled from each of the inner and outer annuli 1606, 1608. Disabled sections 1607, 1609 appear as gaps in the treatment annuli 1606, 1608.

Figure 32:
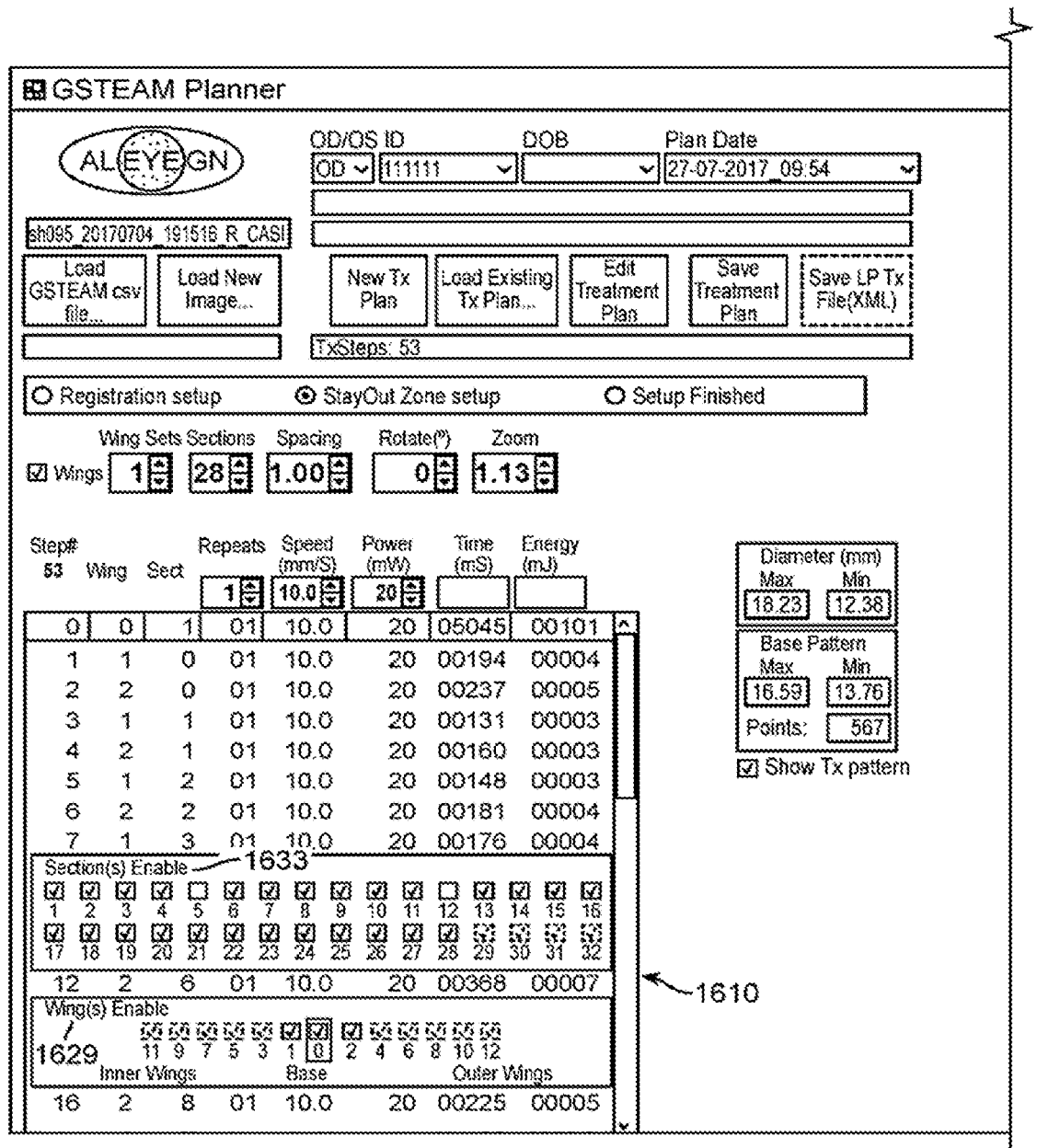
Figure 32:
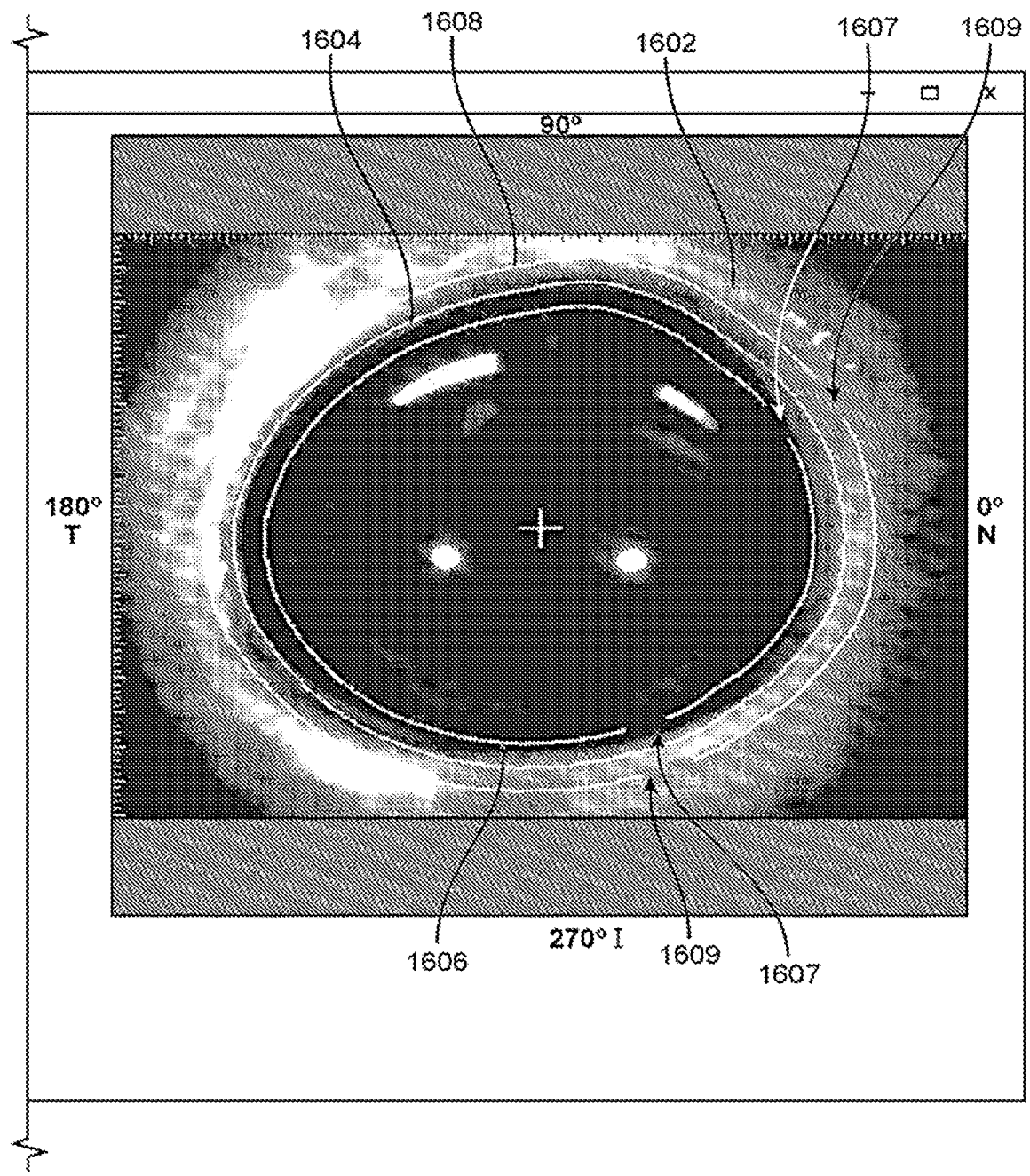
Figure 33:
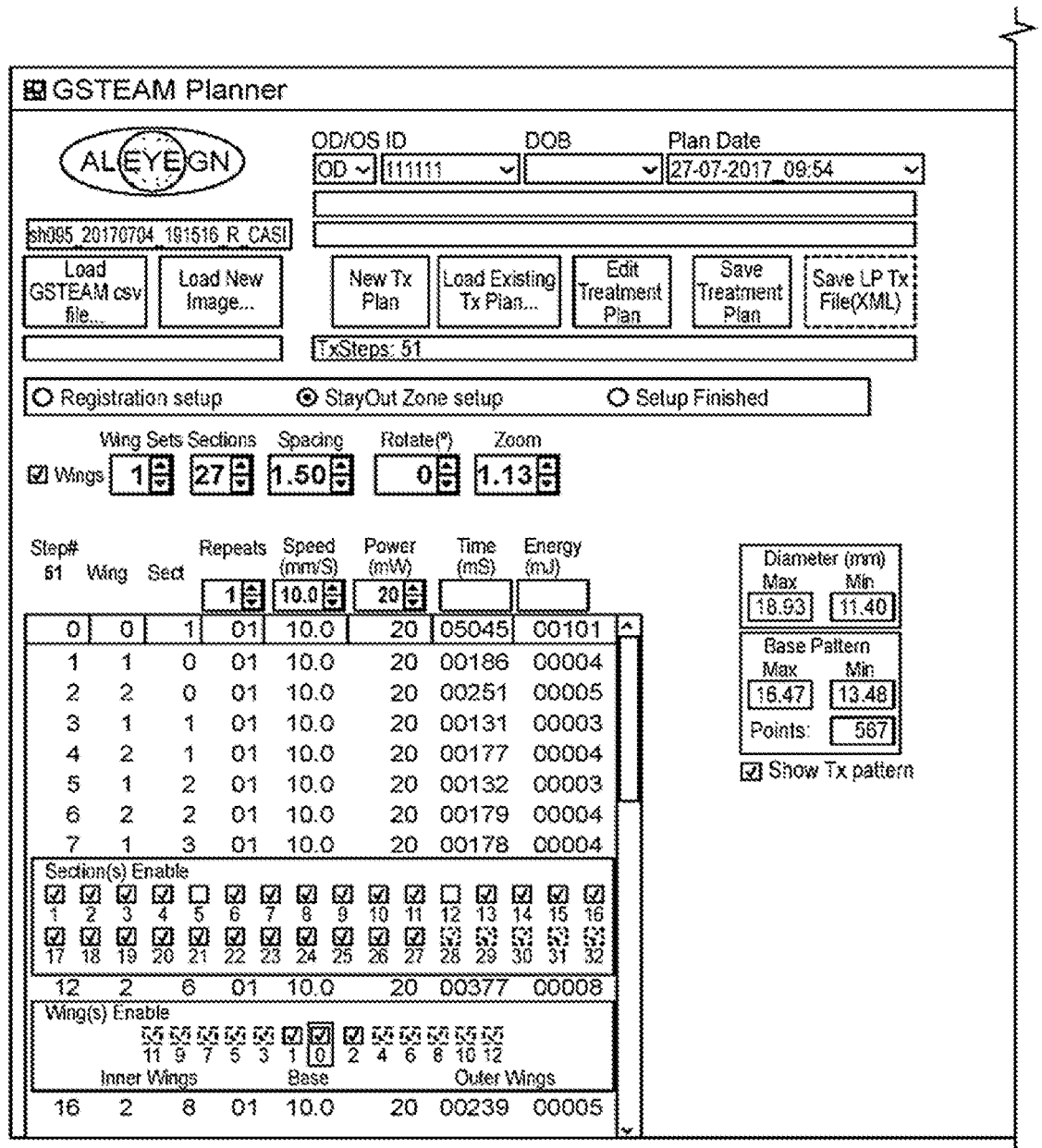
Figure 33:
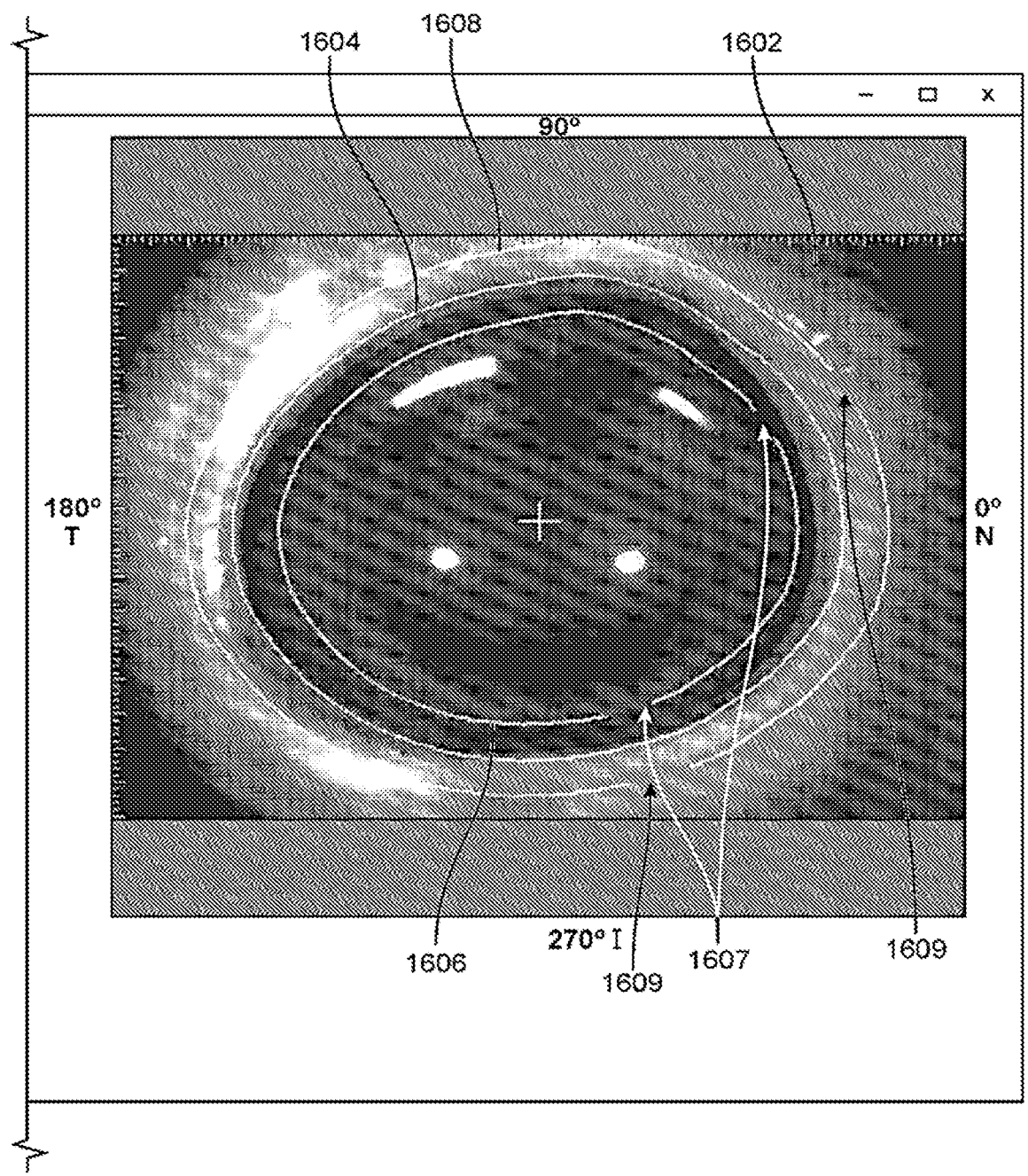
Figure 34:
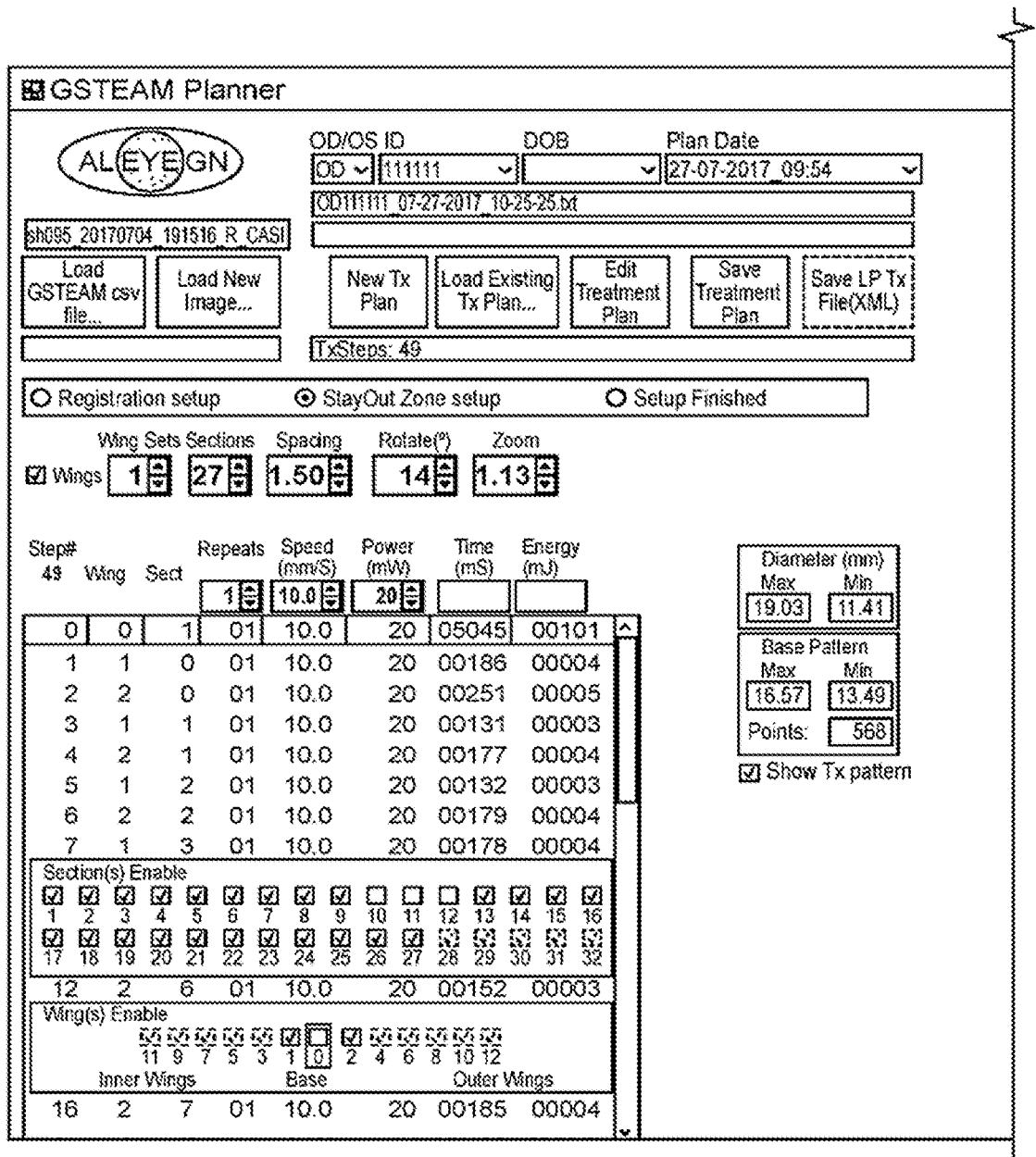
Figure 34:
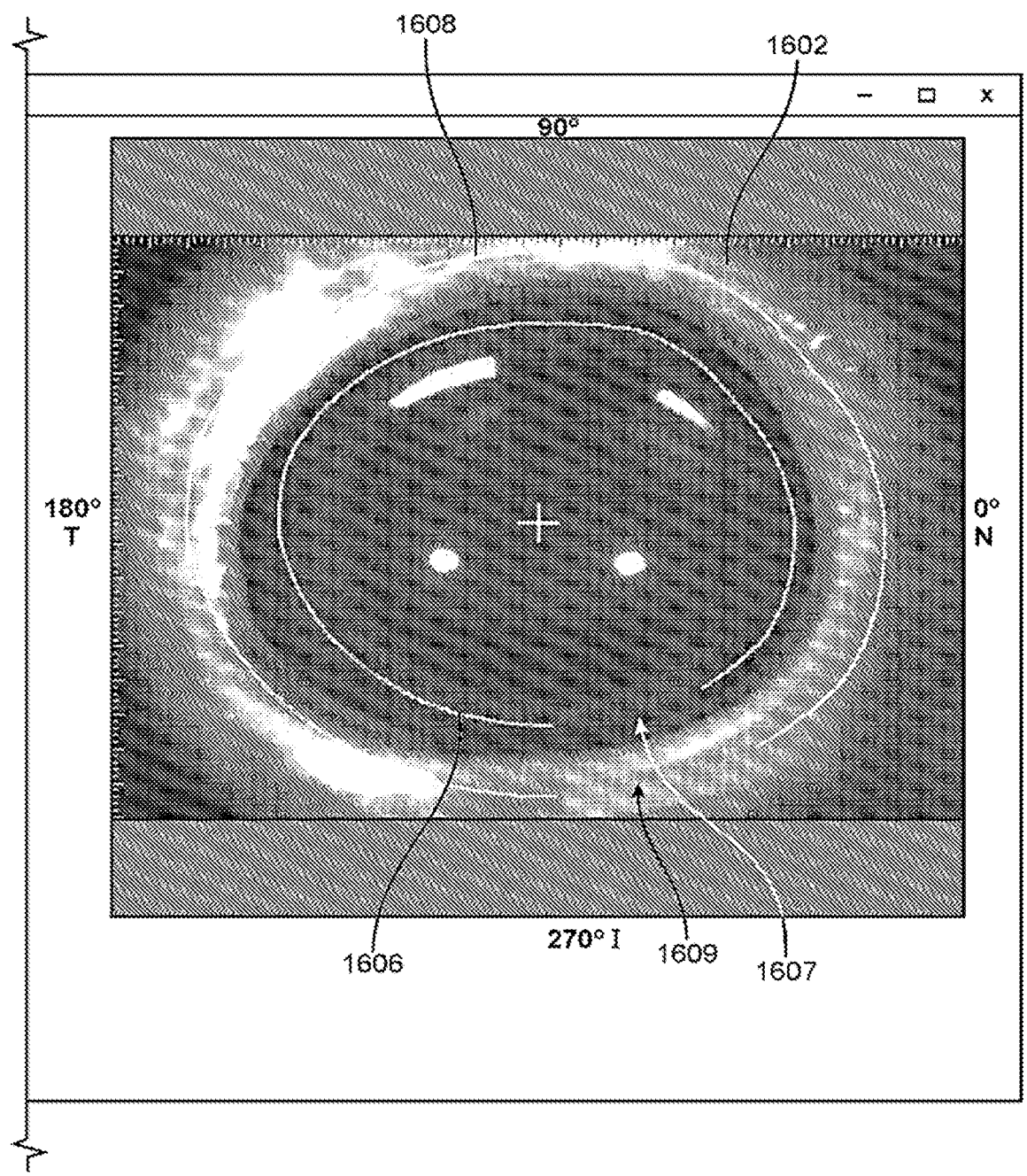

FIGS. 33A and 33B shows a screen capture of the GUI 1600 on the stay-out zone setup page with an anterior image of the eye 1602 comprising overlays of the limbus outline 1604, an inner treatment annulus 1606 with disabled section 1607, and the outer treatment annulus 1608 with disable section 1609. The spacing between the inner and outer treatment annuli 1606, 1608 was increased from 1 mm as shown in FIG. 32 to 1.5 mm by the user as described herein.

FIGS. 34A and 34B show a screen capture of the GUI 1600 on the stay-out zone setup page with an anterior image of the eye 1602 comprising overlays an inner treatment annulus 1606 with disabled section 1607 and the outer treatment annulus 1608 with disabled section 1609. The treatment annuli 1606, 1608 have been rotated as described herein. The limbus overlay 1604 has been removed from view and disabled sections 1607, 1609 have been widened by the user.

Figure 35A:
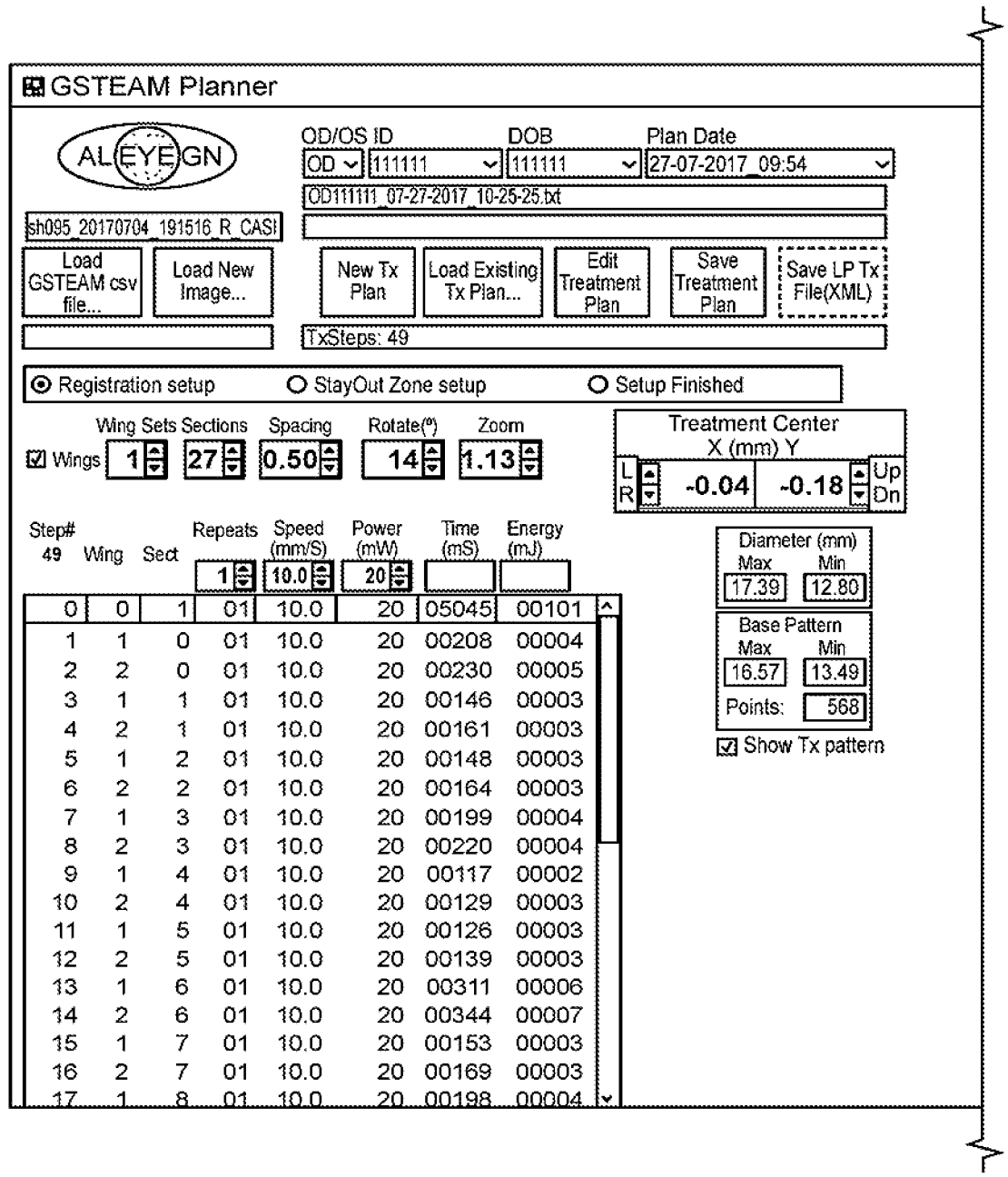
Figure 35B:
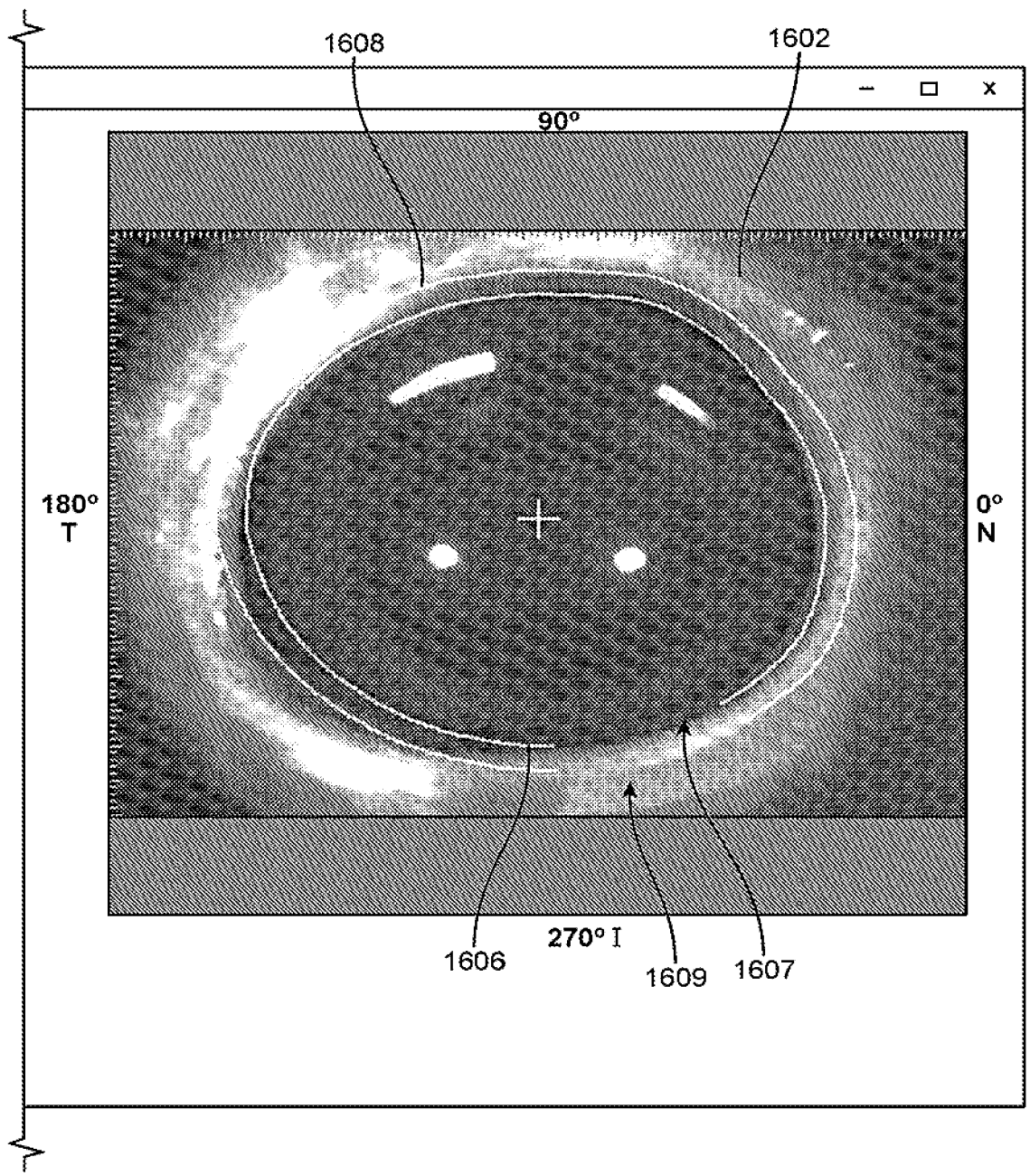

FIGS. 35A and 36B shows a screen capture of the GUI 1600 on the registration setup page with the final treatment setup displayed on the anterior image of the eye 1604. Compared to the initially generated treatment annuli 1606, 1608 shown in FIG. 31, the final annuli 1606, 1608 have disabled sections 1607, 1609, have decreased spacing, are rotated, and have been shifted off-center.

The GUI 1600 may be configured to allow the user to adjust the treatment parameters and provide instructions to the processor. The GUI 1600 may be configured to allow the user to plan the treatment (e.g. set up the treatment pattern, parameters, etc.) prior to treatment. The GUI 1600 may display an anterior image of the eye 1602 to the user prior to, during, or after treatment as described herein. For example, as shown in FIG. 16, the anterior image of the eye 1602 may be displayed with an overlaid outline of the limbus 1604 generated as described herein. In some instances, it may also be desirable to display the treatment location 1606, 1608 on the anterior image of the eye 1602 as shown in FIGS. 31-35. Such overlays 1604, 1606, 1608 may be configured to remain on the real-time anterior image of the eye 1602 displayed during treatment so that the user may monitor treatment progress and accuracy. In some instances, it may be desirable to remove the overlays 1604, 1606, 1608 when treatment begins such that treatment may be monitored without being obscured by the overlay. The anterior image of the eye 1602 may for example be a video of the eye. The anterior image of the eye 1602 may for example comprise a static image taken by a camera. The anterior image of the eye 1602 may for example be a three-dimensional image of the eye.

In use, as an example, a user may upload an anterior image of the eye 1602 to the GUI 1600 using the load new image button 1615 or start the camera to generate an anterior image of the eye 1602 (e.g. a real-time video stream or static two dimensional or three dimensional image of the eye of a patient coupled to the system with a patient interface as described herein). The GUI may be set up with three "pages" as shown to reduce the number of fields visible to the user and reduce clutter on the display, for example to improve workflow efficiency. The pages may for example include a registration setup page which may be selected using the registration setup page button 1621, a stayout zone setup page which may be selected using the stayout zone setup page button 1623, and a setup finished page which may be selected using the setup finished button 1625. The user may then use the GUI to generate a treatment pattern based on the loaded image of the docked patient eye.

The anterior image of the eye 1502 may be loaded with a fiducial marker like the limbus outline 1604 described already drawn on it. Alternatively, or in combination, the limbus outline 1604 may be loaded separately of the anterior image of the eye 1602 using the load GSTEAM csv file button 1614. The x-y coordinates used to generate the limbus outline 1604 may be generated from the anterior image of the eye 1602 using the process described in FIG. 8 for example. The name 1690 of the file which contains the limbus outline 1604 may be displayed to the user by the GUI 1600. Alternatively, or in combination, the user may not upload a limbus outline 1604 and may manually pattern the treatment based on a visual inspection of the location of the limbus. Additional information about the treatment plan may be displayed by the GUI including which eye is being treated in the OD/OS drop down menu 1694, the patient identifier ("ID") in the ID drop down menu 1695, the patient date of birth ("DOB") in the DOB drop down menu 1696, and/or the date of the uploaded image/treatment plan in the plan date drop down menu 1691.

After the image 1602 has been displayed with the limbus outline 1604 (if desired), the user may then begin planning the treatment on the registration setup page. Previously generated treatment steps may be uploaded using the load existing Tx plan button 1618 or a new treatment plan may be set up using the new Tx plan button 1617. Treatment plans generated for future treatments may be saved using the save treatment plan button 1620. A previously generated treatment plan may be edited using the edit treatment plan button. While a juxtacanalicular treatment pattern is shown in FIGS. 31-35, it will be understood by one of ordinary skill in the art that any of the treatment patterns and parameters described herein may be planned for using the GUI.

In the case of juxtacanalicular treatment, a new treatment plan may include at least one limbus-shaped inner annulus 1606 positioned radially inward of the limbus outline 1604 and at least one limbus-shaped outer annulus 1608 positioned radially outward of the limbus outline 1604. The user may press the show Tx pattern button 1605 to display/remove the treatment annuli 1606, 1608 on the anterior image of the eye 1602 as desired. The annuli 1506, 1508 may be generated using the wings button 1631 and wing sets input field 1630. The button 1630 may be used to apply the wings (i.e. a pair of inner and outer annuli) 1606, 1608 while the input field 1631 may be used to adjust the number of wing pairs/sets 1606, 1608. While only a single inner annulus 1606 and a single outer annulus 1608 are shown, it will be understood by one of ordinary skill in the art that additional annuli may be added to the treatment plan as described herein by increasing the number of wing sets in the GUI. Alternatively, the positions of the annuli can be changed to remove the corneal treatment annulus and instead use apply only a scleral annulus, such as a single annulus more than 2 mm outwardly from the limbus.

The spacing/step size between annuli (in mm) may be adjusted using the spacing input field 1634. When no reference fiducial like the limbus outline 1604 is used, or when treatment is patterned without reference to the limbus, the wings button 1531 (or another button not shown) may be used to pattern treatment annuli on the eye, for example at a selected distance from the center.

The rotation of the treatment annuli may be adjusted using the rotate input field 1640. The angle of rotation may be configured to be consistent with conventional reference angles used by a physician when looking at the eye through an operating microscope, as will be understood to one of ordinary skill in the art. The temporal ("T") direction may be at 0°, the nasal ("N") direction may be 180°, the superior ("S") direction may be at 90°, and the inferior ("I") direction may be at 270° (shown here oriented towards the bottom of the display).

The center of the treatment pattern may be adjusted by changing the X and Y coordinates in the treatment center (X,Y) mm input field 1624. The size of the treatment annuli 1506, 1508 may be adjusted using the zoom input field 1638. The diameter 1635 of the entire treatment pattern may be displayed by the GUI. The diameter 1635 may be displayed as a minimum dimension across "min" and a maximum dimension across "max" the entire treatment pattern. The diameter 1637 of the base pattern (i.e. the pattern upon which the treatment annuli are based such as the limbus outline 1604) may be displayed by the GUI. The diameter 1637 may be displayed as a minimum dimension across "min" and a maximum dimension across "max" the entire base pattern. The treatment annuli 1606, 1608 may be made up of one or more treatment sections as described herein. The number of sections/arcs may be selected by the user using the sections input field 1632. The user may select the number of times for each annulus to be treated (e.g. the number of full revolutions or repetitions along the annulus) using the repeats input field 1642. The user may adjust the speed of the laser using the speed mm/sec input field 1648. The user may adjust the power of the laser using the power (mW) input field 1650.

Once the displayed treatment pattern and treatment parameters have been planned by the user, the user may press the new treatment plan button 1617 to display the calculated treatment steps in the treatment step menu 1610. The number of steps 1646 may be displayed. Additional steps may be added by generating new patterns/parameters and adding the next set of treatment steps to the menu 1610. The treatment step menu 1610 may display a variety of information about each step of treatment based on the treatment parameters and patterns selected by the user during treatment planning. For example, information about which wing and which are on said wing is being treated may be displayed in columns in the menu 1610. The user-selected repetition number 1642, the selected scan speed 1648, and the selected laser power 1650 may also be displayed in columns. Additional information may be calculated based on the treatment planned. Such information may be calculated/generated once the treatment steps are added to the menu 1610. Calculated and displayed information may include an estimate of the time to complete each step (in ms) 1656 and/or the amount of energy (in mJ) 1658 delivered in each step.

After determining the location of the treatment annuli 1606, 1608, the user may then push the stay-out zone setup button 1623 to switch the page view to the stay-out zone setup page (shown in FIGS. 18-20). The stay-out zone setup page may include a section(s) enable selection area 1633 and a wing(s) enable selection area 1629 in the menu 1610.

The section(s) enable selection area 1633 may display a plurality of radio/option buttons, one for each section, which may enable treatment of the selected sections (shown as checked boxes) and disable treatment of the unselected sections (shown as unchecked boxes). Disabled sections 1607, 1609 may appear on the treatment pattern overlays 1606, 1608 as blank spaces along the annuli. FIGS. 18 and 19 show an exemplary treatment pattern with sections 5 (corresponding to disabled section 1607 on inner annulus 1606) and 12 (corresponding to disabled section 1609 on outer annulus 1608) unchecked and disabled. FIG. 20 shows an exemplary treatment pattern with sections 10-12 disabled. Sections may be enabled or disabled by the user depending on the desired treatment pattern, for example to avoid critical features of the eye, as will be understood by one of ordinary skill in the art.

The wing(s) enable selection area 1629 may display a plurality of radio/option buttons, one for each annulus, which may enable treatment of the selected annuli (shown as checked boxes) and disable treatment of the unselected annuli (shown as unchecked boxes). Disabled annuli may appear on the treatment pattern overlays as blank spaces between enabled annuli. FIG. 20 shows an exemplary treatment pattern with wing 0 (corresponding to limbus outline 1604) unchecked and disabled. Wings may be enabled or disabled by the user depending on the desired treatment pattern as will be understood by one of ordinary skill in the art. Once the treatment pattern has been planned, the user may select the setup finished button 1625 to begin treatment.

Not all of the elements in FIGS. 30-35 are labeled in order to make the illustrations less cluttered and easier to see. While the GUI shown is configured to be used with a laser system, it will be understood by one of ordinary skill in the art that the GUI may be modified to be used with other energy sources or treatment systems as described herein. Examples of ranges of parameters that may be made available via the GUI include pattern diameters (0.1 mm to 19 mm), number of annuli (1-50), repetitions per annuli (1-100), laser scan speed (0.1-50 mm/s), laser power (1.5 Watts), segmented arcs per annuli (36), centration (camera field of view), limbus derived-shape of patterns (edge detected—100 um accuracy), avoidance of extra-ocular muscles (stay out zones), surface chilling temperature (44 C to 4 C—settable), suction of the ring on the patient interface (50 mbar to 1000 mbar), sequence of annuli (in to out or out to in), sequence of segments (ipsilateral or sequential), and pattern diameters (0.1 mm to 19 mm). Examples of parameters that would be used in the angle-opening method are: pattern diameters within a range of 12 mm-19 mm, for example 13 mm-19 mm, 14 mm-19 mm, 15 mm-10 mm; number of annuli within a range of 1-50, but typically 1-5; repetitions per annuli within a range of 1-100 repetitions, but may for example be 1-20, for example 1, 5, 10, 15, or 20 repetitions; laser scan speed within a range of 0.1-50 mm/s, but may for example be 1-20 mm/s, such as 5, 10, 15, or 20 mm/s; laser power: within a range up to 15 W, for example -0.8 W, 1 W, 1.2 W, or 1.5 W; segmented arcs per annuli generally up to 36, for example 1, 5, 10, 15, 20, 25, 30, 36; surface chilling temperature settable from 44 C to 4 C, but generally with a range of 4-35 C, such as 4, 8, 12, 15, 20, 25, 30, or 35 C; suction of the ring generally within a range of 50 mbar to 1000 mbar, for example 100-500 mbar.

In some instances, the treatment may be planned using the GUI(s) described herein during the therapeutic appointment, for example immediately prior to treatment. In some instances, the treatment may be planned prior to the therapeutic appointment. For example, an image taken during a consultation prior to the therapeutic appointment may be used to plan the treatment any time before the patient returns for the therapeutic appointment. In some instances, the treatment may be planned prior to the therapeutic appointment and then adjusted during the therapeutic appointment prior to (or during) treatment. The GUIs described herein may for example be used to plan treatment using a static anterior image of the eye taken during a consultation appointment. During the therapeutic appointment, a video camera may be used to allow the physician user to align the pre-planned treatment pattern onto the eye docked into the patient interface of the system and make any adjustments necessary to set up the treatment as desired.

The anterior image of the eye may be calibrated or registered to the laser delivery system (e.g. the laser scanner) and/or to the imaging system (e.g. the OCT system) such that the treatment planned based on the anterior image of the eye fairly represents the treatment delivered to the eye during the glaucoma treatment procedure.

Figure 36:
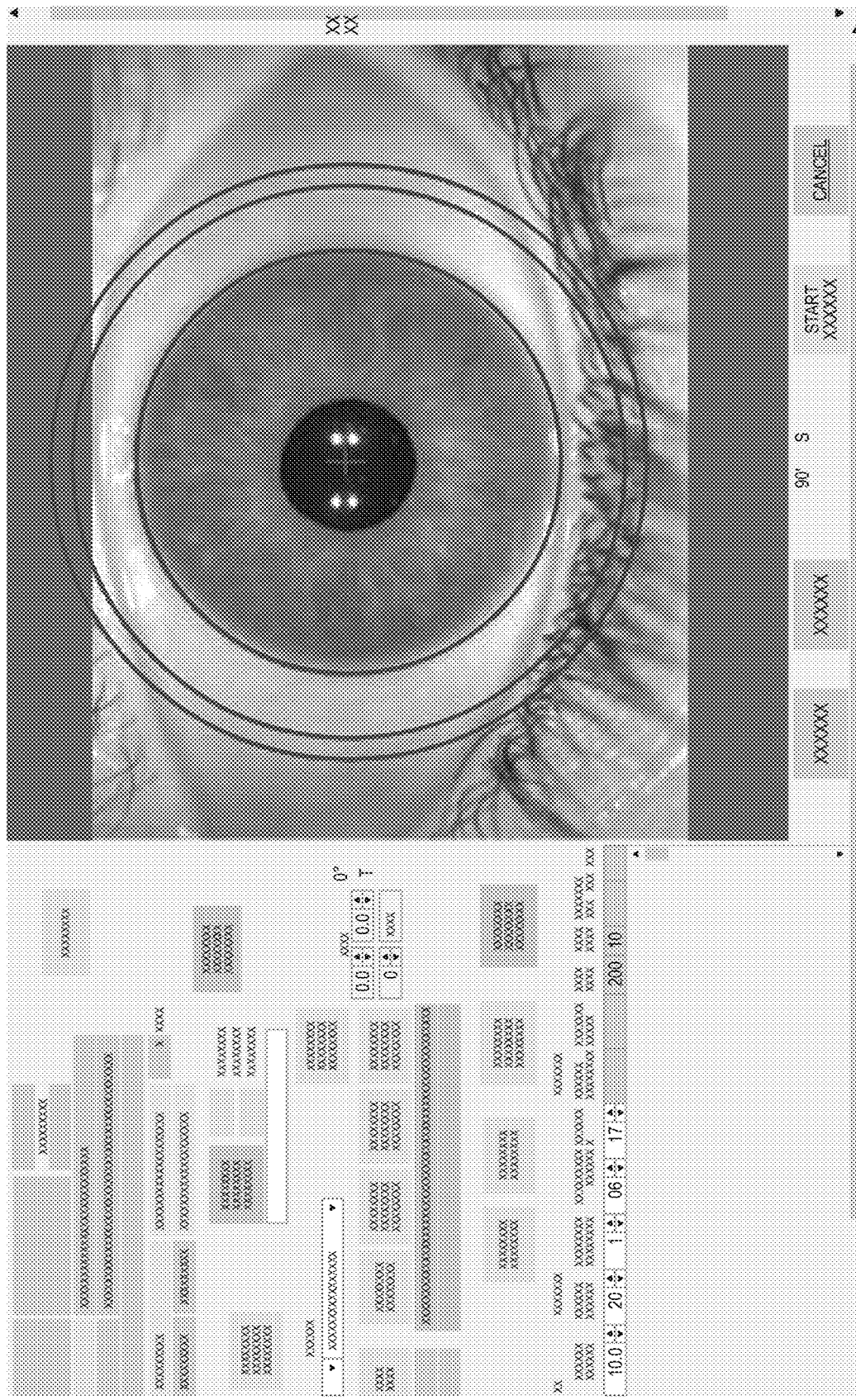
FIGS. 36-38 show graphical user interfaces of the treatment system for patterning treatment locations outwardly from (posterior to) the limbus.
Figure 37:
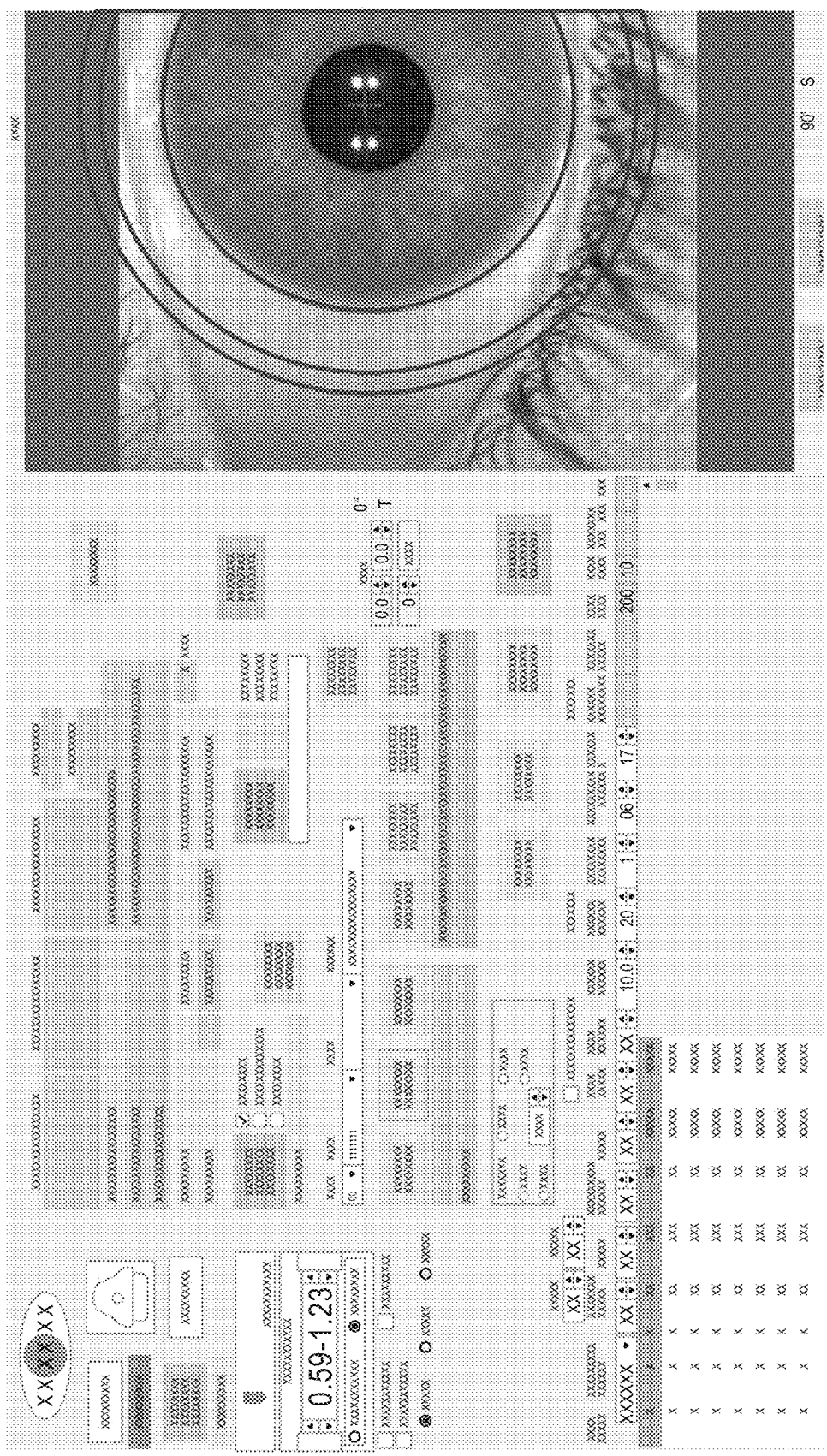
Figure 38:
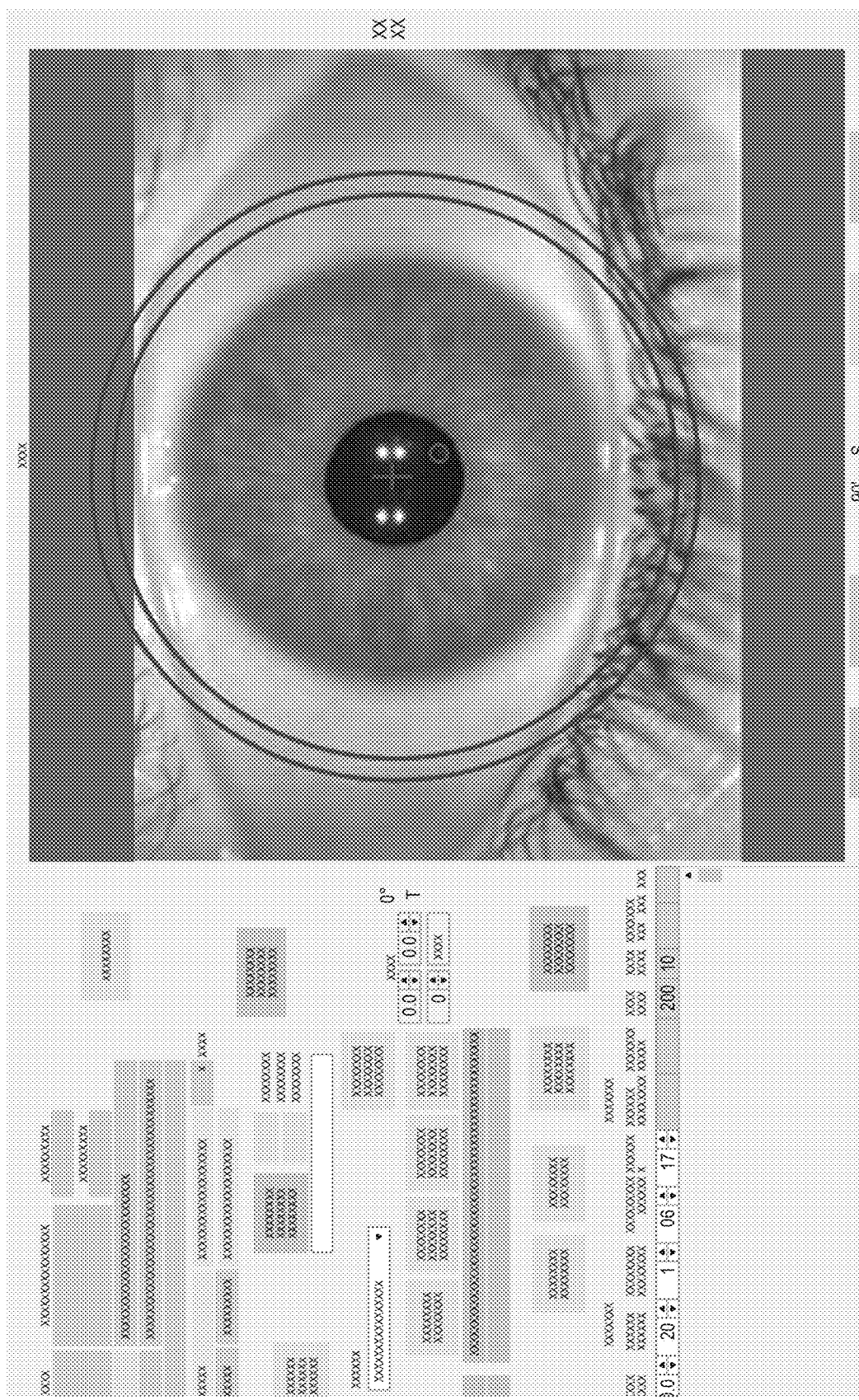

FIGS. 36-37 show an innermost annulus marker that overlays the limbus, and the position of two outer annuli that are spaced more than 2 mm outwardly from the limbus and anterior to the scleral equator. FIG. 38 shows the two outer treatment annuli, with the limbus annulus marker removed.

Figure 39:
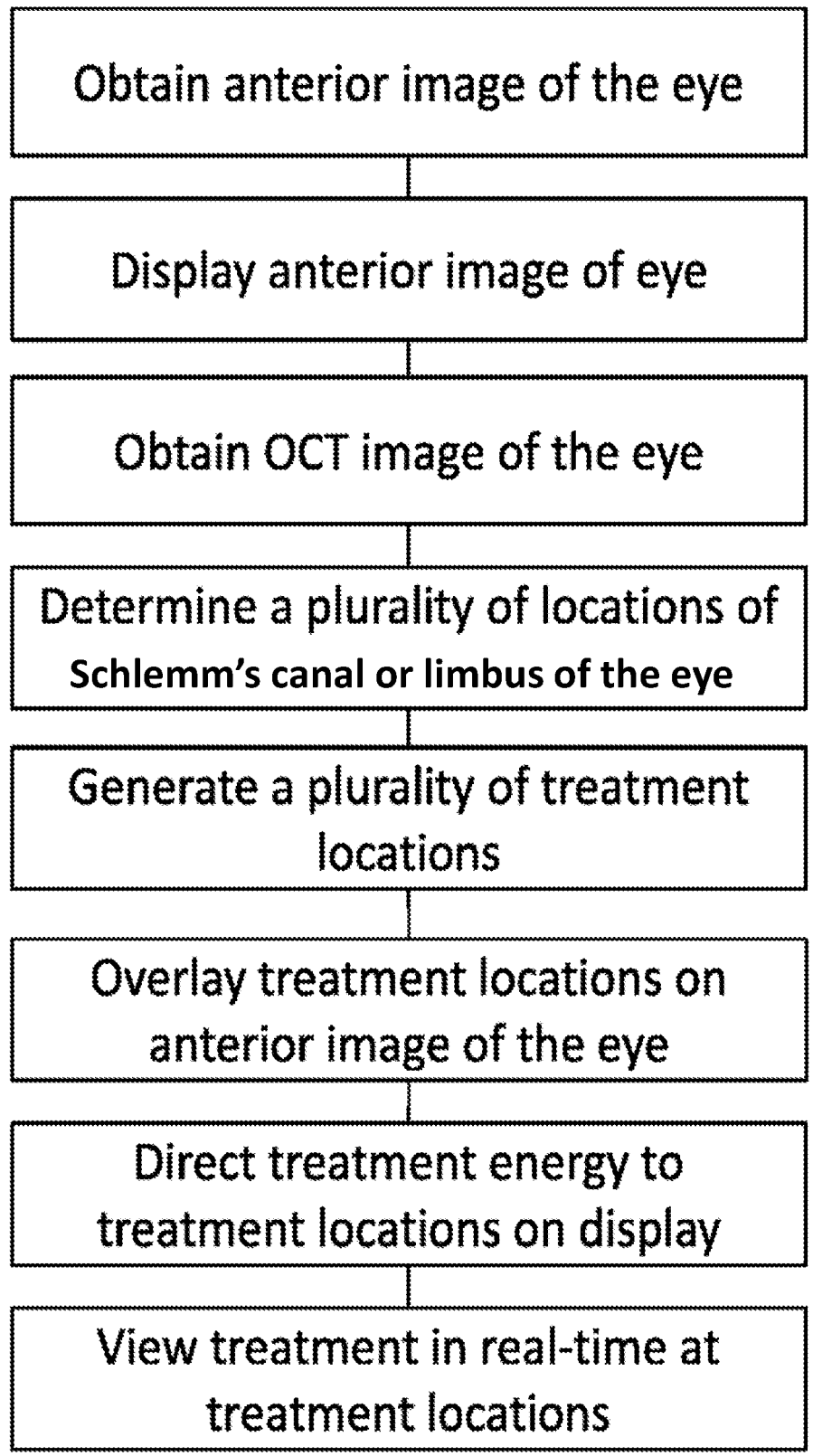
FIG. 39 shows a flowchart of a method for determining a target treatment location, in accordance with embodiments.

FIG. 39 shows a method for determining a target treatment location. The method may use one or more of the systems described herein. In a first step, an anterior image of the eye may be obtained by a camera or video recorder. In a second step, the image of the eye may be displayed to a user as described herein. In a third step, one or more OCT images of the eye may optionally be obtained. In a fourth step, a plurality of locations of Schlemm's canal (or the limbus or other fiducial described herein) may be determined from the anterior image of the eye, the one or more OCT images of the eye, or any combination thereof. The plurality of locations of Schlemm's canal may be estimated manually by the user or automatically by the processor. The plurality of Schlemm's canal locations may optionally be registered with a corresponding plurality of anterior image locations. In a fifth step, a plurality of treatment locations for the eye may be determined in response to the plurality of locations of Schlemm's canal. The plurality of treatment locations may be determined manually by the user or automatically by the processor. In a sixth step, the treatment locations may be overlaid onto the anterior image shown on the display. The treatment locations may optionally be adjusted or approved by the user. In a seventh step, treatment energy may be directed to the treatment locations displayed on the image by an energy source and scanner as described herein. In an eighth step, the treatment may be viewed in real-time at the treatment locations to adjust or halt treatment if movement of the eye occurs.

In some instances, a processor may be provided. The processor may be configured with instructions for perform a series of steps illustrated in FIG. 39. In some instances, the processor may provide instructions to obtain an anterior image of the eye. For example, the anterior image of the eye may be obtained with a camera with aid of the processor. In some instances, the processor may be configured with instructions for receiving an anterior image of the eye.

In some instances, the processor may provide instructions to display the anterior image of the eye. In some instances, the processor may provide instructions to obtain OCT image(s) of the eye. In some instances, the processor may provide instructions to determine a plurality of locations of Schlemm's canal of the eye. The processor may estimate in some instances the plurality of Schlemm's canal locations in response to the anterior image of the eye. Alternatively, or in addition, the processor may estimate the plurality of Schlemm's canal locations in response to the plurality of OCT images of the eye.

In some instances, the processor may be configured with instructions to generate a plurality of treatment locations. Optionally, the processor may be configured with instructions to generate the plurality of treatment locations for the eye in response to the plurality of Schlemm's canal locations.

In some instances, the processor may provide instructions to overlay treatment locations on the anterior image of the eye. The processor may be configured with instructions to overlay the plurality of treatment locations and the plurality of Schlemm's canal locations on the anterior image of the eye. Optionally, the processor may be further configured to register the plurality of locations of Schlemm's canal with a corresponding plurality of anterior image locations.

In some instances, the processor may provide instructions to direct treatment energy to treatment locations on the display. In some instances, the processor may be configured with instructions to alternate treatment at a first plurality of treatment locations with treatment at a second plurality of treatment locations as described herein. Optionally, the processor may be configured with instructions to generate a third plurality of treatment locations located radially outward from the second plurality of treatment locations to generate vacuoles or increase a size of vacuoles in a sclera of the eye.

Optionally, the processor may be configured with instructions to generate a treatment table. The treatment table may comprise a plurality of coordinate reference locations corresponding to the plurality of treatment locations overlaid on the anterior image. Optionally, the energy source directed to the eye may comprise a pulsed energy source wherein each of the plurality of coordinate references corresponds to a pulse from an energy source.

In some instances, the processor may provide instructions to display treatment in real-time at the treatment locations.

Although the steps described above show a method of acquiring an image of an eye and treating the tissue at a treatment region selected by a user, one of ordinary skill in the art will recognize many variations based on the teachings described herein. The steps may be completed in a different order. Steps may be added or deleted. Some of the steps may comprise sub-steps. Many of the steps may be repeated as often as necessary to treat the tissue as desired.

For experiments that were conducted on ex vivo porcine eyes, a person of ordinary skill in the art can conduct in vivo experiments on living human eyes in order to develop nomograms to position the lens of the eye to correct vision with treatment energies as described herein. For example, the laser system can be coupled to an OCT measurement system as described herein, and OCT measurements on living human eyes during surgery can be used to measure movement of the lens in response to treatment as described herein, to determine amounts and locations of energy treatment that produce desired amounts of movement of the lens. The OCT system can be coupled to the laser system with a beam splitter, such that the laser beam path and OCT measurement beam path are aligned, and the patient can be measured in situ. Also, although treatment dimensions are provided with reference to porcine eyes, which typically have dimensions 10 to 20% greater (or more) than human eyes, a person of ordinary skill in the art can target similar structures with human eyes by decreasing the dimensions of porcine eyes by approximately 10 to 20% to target similar tissue structures on human eyes. Additionally, porcine eyes typically comprise different types and amounts (or ratios of collagen types) than human eyes and a person of ordinary skill in the art can adjust the treatment parameters to account for such differences.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for treating glaucoma of an eye, the system comprising:
    an energy source configured to generate energy to treat the eye; and
    a processor configured with instructions to:
    direct energy to a plurality of treatment locations of the eye, the plurality of treatment locations located at least 2 mm radially outward from a limbus and corresponding to an angle within a range from 30 degrees to 360 degrees around a sclera of the eye;
    an energy delivery system coupled to the energy source and the processor, the energy delivery system configured to deliver the energy to the plurality of treatment locations in order to open an angle of the eye, corresponding to an iridocorneal angle of the eye extending between an iris and a cornea of the eye, by an amount within a range from 0.5 degrees to 10 degrees;
    wherein the eye comprises a human eye and the plurality of locations correspond to a surface area on the sclera, and wherein the surface area is within a range from 1 $mm^2$ to 100 $mm^2$ and wherein the surface area is located radially outward from the limbus on a sclera of the eye by at least 2.5 mm and anterior to a lens equator on the sclera of the human eye and wherein the angle opens in response to the plurality of treatment locations and wherein the plurality of treatment locations is located anterior to the lens equator by no more than 3 mm.

2. The system of claim 1, wherein the processor is configured to fractionate energy delivered to the plurality of treatment locations and wherein an amount of energy delivered to each of the plurality of treatment locations with an energy exposure comprises no more than 50% of a total amount of energy delivered to said each of the plurality of treatment locations and wherein said exposure comprises an amount within a range from 2% to 50% for said each of the plurality of treatment locations and wherein said amount is within a range from 10% to 34% of the total amount of energy delivered for said each of the plurality of treatment locations.

3. The system of claim 2, wherein said energy exposure comprises a time within a range from 1 millisecond (ms) to 200 ms for said each of the plurality of treatment locations and wherein said each of the plurality of treatment locations receives a plurality of exposures, wherein a time between said plurality of energy exposures for said each of the plurality of treatment locations is within a range from three times (3×) the exposure time to 200 times (200×) the exposure time, wherein a total amount of energy delivered to the eye with the plurality of treatment locations to open the angle is within a range from 25 J to 150 J.

4. The system of claim 1, wherein the plurality of treatment locations is arranged to tension zonules coupled to a lens of the eye to urge an equator of the eye radially outward in order to allow an iris of the eye to move posteriorly to increase the angle and wherein a spherical refraction of the eye changes by no more than 1 Diopters in response to the tensioning of the zonules, wherein the plurality of treatment locations is arranged to increase an anterior chamber depth extending between the cornea of the eye and the lens of the eye by an amount within a range from 0.5 mm to 2 mm in response to tensioning of the plurality of zonules, wherein the plurality of treatment locations comprise locations on the sclera of the eye anterior to the equator of the eye and wherein the energy is configured to shrink tissue at the plurality of locations on the sclera in order to tension the plurality of zonules.

5. The system of claim 1, wherein the processor is configured with instructions to receive an input corresponding to a location of a lens equator on the sclera and wherein the processor is configured to determine the plurality of locations in response to the input and wherein the plurality of locations is offset radially inward from the input location corresponding to the lens equator on the sclera.

6. The system of claim 1, wherein the plurality of treatment locations correspond to an annular treatment pattern located at least 2.5 mm radially outward from the limbus of the eye and anterior to the lens equator.

7. The system of claim 1, wherein the processor is configured with instructions to shrink tissue with at least a portion of a first annular treatment pattern prior to shrinking tissue with at least a portion of a second annular treatment pattern.

8. The system of claim 7, wherein the first annular treatment pattern comprises a first plurality of spaced apart annular treatment patterns and the second annular treatment pattern comprises a second plurality of spaced apart annular treatment patterns, wherein the first plurality of spaced apart annular treatment patterns comprises angularly, radially, or both angularly and radially, separated spaced apart treatment patterns, and the second plurality of annular treatment pattern comprises angularly, radially, or both angularly and radially, separated spaced apart treatment patterns.

9. The system of claim 1, wherein the processor is configured with instructions to repeatedly deliver the energy to each of the plurality of treatment locations with a time delay in order to fractionate delivery of energy to said each of the plurality of treatment locations, wherein the time delay is within a range from 10 millisecond (ms) to 60 seconds.

10. The system of claim 7, wherein the processor coupled to the energy source and the energy delivery system is configured with instructions to heat tissue at the plurality of treatment locations to a temperature within a range from 60 to 70 degrees Centigrade at a depth within a range from 50 to 400 μm at each of the plurality of treatment locations along the first annular treatment pattern and the second annular treatment pattern, wherein a majority of a treatment energy of the first annular treatment pattern is located within 1.5 mm of the Schlemm's canal and a majority of treatment energy of the second annular treatment pattern is located within 1.5 mm of Schlemm's canal, wherein the first annular treatment pattern extends at least 30 degrees around the optical axis of the eye and the second annular treatment pattern extends at least 30 degrees around the optical axis of the eye.

11. The system of claim 7, wherein the first annular treatment pattern and the second annular treatment pattern are arranged to avoid heating tissue overlaying the Schlemm's canal, wherein the first annular treatment pattern and the second annular treatment pattern comprise circular, oval, elliptical, egg-like, non-circular, non-elliptical, or asymmetrical, shapes patterned so as to correspond to the shape of Schlemm's canal or the limbus.

12. The system of claim 1, wherein the energy source comprises one or more of a pulsed laser or a continuous laser having a wavelength within a range from 1.4 to 2.3 μm, wherein the energy delivery system comprises a scanner, an optical imaging system, a mask, a hand held probe, or an ultrasound lens.

13. The system of claim 1, wherein the processor is configured with instructions to generate vacuoles in the sclera of the eye.

14. The system of claim 1, wherein the processor is configured with instructions to sequentially direct energy to the plurality of locations in response to a radial position of the plurality of locations and wherein the energy directed to radially outward locations of the plurality of locations is delivered to the sclera of the eye before radially inward locations in order to generate an antero centrifugal force to the lens of the eye.

15. The system of claim 1, wherein the processor is configured with instructions to receive user input corresponding to angles and radial locations, and wherein the user input corresponds to a partial annular treatment at a radial location in order to avoid insertion muscles coupled to the sclera of the eye.

16. The system of claim 1, wherein the processor is further configured with instructions to direct energy to a plurality of other treatment locations of the eye that are:
　(a) within 2 mm of Schlemm's Canal to enlarge Schlemm's Canal; and/or
　(b) within 1 mm of the collector channels or ostia of the collector channels to improve aqueous outflow through the collector channels,
　wherein the plurality of other treatment locations correspond to an angle within a range from 30 degrees to 360 degrees around the sclera of the eye.

17. A system to treat glaucoma of an eye, the system comprising:
　an energy source;
　a processor configured with instructions to direct energy to a plurality of treatment locations of the eye, the plurality of treatment locations located at least 2 mm radially outward from a limbus and corresponding to an angle within a range from 30 degrees to 360 degrees around a sclera of the eye;
　a handpiece coupled to the energy source and the processor, the handpiece comprising:
　an eye contacting surface to couple to the eye and a plurality of energy releasing elements disposed at a plurality of handpiece locations to release energy to the eye at the plurality of treatment;

wherein the handpiece is configured to deliver the energy to the plurality of treatment locations in order to open an iridocorneal angle of the eye by an amount within a range from 0.5 degrees to 10 degrees;

wherein the eye comprises a human eye and the plurality of treatment locations correspond to a surface area on the sclera, and wherein the surface area is within a range from 1 mm$^2$ to 100 mm$^2$ and wherein the surface area is located radially outward from the limbus on a sclera of the eye by at least 2.5 mm and anterior to a lens equator on the sclera of the human eye and wherein the iridocorneal angle opens in response to the plurality of treatment locations and wherein the plurality of treatment locations is located anterior to the lens equator by no more than 3 mm.

18. A method for treating glaucoma of an eye, the method comprising:

delivering energy to a plurality of treatment locations of the eye, the plurality of treatment locations located at least 2 mm radially outward from a limbus and corresponding to an angle within a range from 30 degrees to 360 degrees around a sclera of the eye, wherein the energy delivered to the plurality of treatment locations opens an iridocorneal angle of the eye by an amount within a range from 0.5 degrees to 10 degrees;

wherein the eye comprises a human eye and the plurality of locations correspond to a surface area on the sclera, and wherein the surface area is within a range from 1 mm$^2$ to 100 mm$^2$ and wherein the surface area is located radially outward from the limbus on a sclera of the eye by at least 2.5 mm and anterior to a lens equator on the sclera of the human eye and wherein the iridocorneal angle opens in response to the plurality of treatment locations and wherein the plurality of treatment locations is located anterior to the lens equator by no more than 3 mm.

19. The method of claim 18, further comprising delivering energy to another a plurality of treatment locations that are:
(a) within 2 mm of Schlemm's Canal to enlarge Schlemm's Canal; and/or
(b) within 1 mm of the collector channels or ostia of the collector channels to improve aqueous outflow through the collector channels.

\* \* \* \* \*